(12) United States Patent
Lannutti et al.

(10) Patent No.: US 10,646,470 B2
(45) Date of Patent: *May 12, 2020

(54) USES OF INDOLINONE COMPOUNDS

(71) Applicant: Oncternal Therapeutics, Inc., San Diego, CA (US)

(72) Inventors: Brian Lannutti, Solana Beach, CA (US); Katayoun Jessen, San Diego, CA (US); James Bradley Breitmeyer, San Diego, CA (US)

(73) Assignee: Oncternal Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/114,076

(22) Filed: Aug. 27, 2018

(65) Prior Publication Data

US 2019/0022062 A1 Jan. 24, 2019

Related U.S. Application Data

(63) Continuation of application No. 15/660,566, filed on Jul. 26, 2017, now Pat. No. 10,159,660.

(Continued)

(51) Int. Cl.
| | |
|---|---|
| *A61K 31/415* | (2006.01) |
| *A61K 31/445* | (2006.01) |
| *A61K 31/404* | (2006.01) |
| *A61K 39/395* | (2006.01) |
| *A61K 45/06* | (2006.01) |
| *A61K 31/4439* | (2006.01) |

(Continued)

(52) U.S. Cl.
CPC ........ *A61K 31/404* (2013.01); *A61K 31/4155* (2013.01); *A61K 31/4439* (2013.01); *A61K 31/496* (2013.01); *A61K 31/5377* (2013.01); *A61K 31/551* (2013.01); *A61K 39/39558* (2013.01); *A61K 45/06* (2013.01); *C07K 16/2887* (2013.01); *C07K 2317/24* (2013.01); *C07K 2317/73* (2013.01)

(58) Field of Classification Search
CPC .. A61K 31/404; A61K 31/551; A61K 31/497; A61K 38/00
USPC .......................... 514/418, 220, 253.04, 19.3
See application file for complete search history.

(56) References Cited

U.S. PATENT DOCUMENTS

| | | | |
|---|---|---|---|
| 6,969,729 B2 | 11/2005 | Jensen et al. | |
| 8,232,310 B2 | 7/2012 | Toretsky et al. | |

(Continued)

FOREIGN PATENT DOCUMENTS

| | | |
|---|---|---|
| CN | 1365972 A | 8/2002 |
| CN | 102516152 | 6/2012 |

(Continued)

OTHER PUBLICATIONS

Abaan et al., "PTPL1 is a direct transcriptional target of EWS-FLI1 and modulates Ewing's sarcoma tumorigenesis", Oncogene (2005) 24(16): 2715-2722.

(Continued)

*Primary Examiner* — Shengjun Wang
(74) *Attorney, Agent, or Firm* — Knobbe, Martens, Olson & Bear, LLP

(57) ABSTRACT

Methods and compositions for treating acute myeloid leukemia and diffuse large B cell lymphoma using combinations of venetoclax and indolinone derivatives are provided.

8 Claims, 21 Drawing Sheets

Related U.S. Application Data

(60) Provisional application No. 62/368,707, filed on Jul. 29, 2016, provisional application No. 62/417,572, filed on Nov. 4, 2016, provisional application No. 62/422,504, filed on Nov. 15, 2016, provisional application No. 62/426,107, filed on Nov. 23, 2016, provisional application No. 62/503,238, filed on May 8, 2017, provisional application No. 62/534,067, filed on Jul. 18, 2017.

(51) Int. Cl.
| | | |
|---|---|---|
| A61K 31/5377 | (2006.01) | |
| A61K 31/4155 | (2006.01) | |
| A61K 31/496 | (2006.01) | |
| A61K 31/551 | (2006.01) | |
| C07K 16/28 | (2006.01) | |

(56) References Cited

U.S. PATENT DOCUMENTS

| | | |
|---|---|---|
| 8,232,410 B2 | 7/2012 | Ojima et al. |
| 9,045,415 B2 | 6/2015 | Toretsky et al. |
| 9,290,449 B2 | 3/2016 | Toretsky et al. |
| 9,511,050 B2 | 12/2016 | Toretsky et al. |
| 9,604,927 B2 | 3/2017 | Vernier |
| 9,714,222 B2 | 7/2017 | Toretsky et al. |
| 9,758,481 B2 | 9/2017 | Toretsky et al. |
| 9,895,352 B2 * | 2/2018 | Vernier ............ C07D 209/38 |
| 9,987,251 B2 * | 6/2018 | Vernier ............ C07D 209/38 |
| 10,159,660 B2 * | 12/2018 | Lannutti ............ A61K 31/404 |
| 2002/0016354 A1 | 2/2002 | Jensen et al. |
| 2002/0042427 A1 | 4/2002 | Tang et al. |
| 2005/0288244 A1 | 12/2005 | Manoharan et al. |
| 2010/0004179 A1 | 1/2010 | Toretsky et al. |
| 2010/0160260 A1 | 6/2010 | Skordalakes |
| 2010/0167994 A1 | 7/2010 | Toretsky et al. |
| 2013/0259927 A1 | 10/2013 | Nemunaitis et al. |
| 2015/0051260 A1 | 2/2015 | Toretsky et al. |
| 2015/0158846 A1 | 6/2015 | Crawford et al. |
| 2015/0329488 A1 | 11/2015 | Toretsky et al. |
| 2016/0102055 A1 | 4/2016 | Vernier |
| 2016/0159741 A1 | 9/2016 | Toretsky et al. |
| 2016/0263086 A1 | 9/2016 | Toretsky et al. |
| 2017/0065559 A1 | 3/2017 | Vernier |
| 2017/0283420 A1 | 10/2017 | Webber |
| 2017/0349600 A1 | 12/2017 | Webber |
| 2018/0256546 A1 | 9/2018 | Vernier |

FOREIGN PATENT DOCUMENTS

| | | |
|---|---|---|
| CN | 103435606 | 12/2013 |
| EP | 0133244 A2 | 2/1985 |
| WO | WO 2001/027081 | 4/2001 |
| WO | WO 2003/000925 A1 | 1/2003 |
| WO | WO 2006/113864 | 10/2006 |
| WO | WO 2006/117414 A1 | 11/2006 |
| WO | WO 2008/046083 | 4/2008 |
| WO | WO 2008/083326 | 7/2008 |
| WO | WO 2010/042225 | 4/2010 |
| WO | WO 2010/083505 | 7/2010 |
| WO | WO 2012/078519 | 6/2012 |
| WO | WO 2013/155341 | 10/2013 |
| WO | WO 2015/078929 | 6/2015 |

OTHER PUBLICATIONS

Allu et al., "Enantioselective organocatalytic adol reaction of unactivated ketones with isatins," Tetrahedron Letters 52:4080-4083 (2011).
Anderson et al., "BRCA1 protein is linked to the RNA polymerase II holoenzyme complex via RNA helicase A", Nat Genet (1998) 19(3):254-256.
Ankhiwala, Studies in Spiroheterocycles. Synthesis and Antimicrobial Activities of Some New Spiro (indoline-3, 5'-pyrazonlin)-1'-phenyl-2-ones and Spiro ( . . . J Indian Chem Soc. (1990) 67: 432-434.
Babu et al., "Heteropolyacid-silica mediated [3+2] cycloaddition of ylides—a facile multicomponent one-pot synthesis of novel dispiroheterocycles", Tetrahedron Ltt. (2006) 47(52): 9221-9225.
Baer et al., "Profiling and functional annotation of mRNA gene expression in pediatric rhabdomyosarcoma and Ewing's sarcoma", Int J Cancer (2004) 110(5):687-694.
Balamuth et al., "Ewing's Sarcoma", Lancet Oncology (2010) 11(2): 184-192.
Bayoumy et al., "Studies on Spiroheterocyclic Nitrogen Compounds. Part 1: Synthesis of Some New Spiro Pyrazolines, Isoxazolines and Pyrimidinethiones Containing Benzanilide Moiety", J Indian Chem Soc. (1984) LXI(1):520-522.
Beccalli et al., "Synthesis of [a]annulated carbazoles from indol-2,3-dione." Tetrahedron (1993) 49(21): 4741-4758.
Becerra et al., "Hydrogen-bonding patterns in 3-alkyl-3-hydroxyindolin-2-ones," Acta Cryst. C66:o79-o86 (2010).
Berg et al., "Small-molecule antagonists of Myc/Max dimerization inhibit Myc-induced transformation of chicken embryo fibroblasts", Proc Natl Acad Sci U S A (2002) 99(6):3830-3835.
Bhalla et al., "Local flexibility in molecular function paradigm", Mol Cell Proteomics (2006) 5:1212-1223.
Bonetti et al, "Deregulation of ETS1 and FLI1 contributes to the pathogenesis of diffuse large B-cell lymphoma", Blood (2013) 122(13): 2233-2241.
Bowdish et al., "Immunomodulatory properties of defensins and cathelicidins", Curr Top Microbiol Immunol (2006) 306:27-66.
Braun et al., "Identification of target genes for the Ewing's sarcoma EWS/FLI fusion protein by representational difference analysis", Mol Cell Biol (1995) 15(8):4623-4630.
Byler et al, "Identification of benzoylisoquinolines as potential anti-Chagas agents," J Bioorg Med Chem. 20:2587-2594 (2012).
Carter et al., "Chemotherapy of Cancer", 2nd Edition; John Wiley & Sons, New York (1981), Appendix C—Drug-Tumor Interactions; 5 pages.
Castillero-Trejo et al., "Expression of the EWS/FLI-1 oncogene in murine primary bone-derived cells results in EWS/FLI-1-dependent, Ewing sarcoma-like tumors", Cancer Res (2005) 65(19):8698-8705.
Chemical Abstract compound, STN express; RN-340220-38-4 (Entered STN: Jun. 10, 2001); 1 Page.
Chemical Abstract compound, STN express; RN-908809-06-3 (Entered STN: Sep. 27, 2006); 1 Page.
CAS Registry No. 351329-43-6 (MicroChemistry Ltd.) entered: Aug. 14, 2001; 3-(2-cyclopropyl-2-oxoethyl)-1,3-dihydro-3-hydroxy-2H-Indol-2-one; 1 page.
CAS Registry No. 1159977-04-4 indexed in the Registry File online Jun. 25, 2009; 1 page.
Chen et al., "Specific alterations of U1-C protein or U1 small nuclear RNA can eliminate the requirement of Prp28p, an essential DEAD box splicing factor", Mol Cell (2001) 7(1):227-232.
Chen et al, "Catalyst-free aldol condensation of ketones and isatins under mild reaction conditions in DMF with molecular sieves 4 A as additive," Green Chem. 11:1465-1476 (2009).
Cheng et al., "Rational drug design via intrinsically disordered protein", Trends Biotechnol. (2006) 24(10):435-442.
Chung et al, "The small molecule YK-4-279 shows anti-lymphoma activity in pre-clinical models" Abstract No. 1654 in Proceedings of the 106th Annual Meeting of the AACR; Apr. 18-22, 2015; Philadelphia, PA; 2 pages.
Dandia et al., "Investigation of the Reactions of some New Fluorine containing 3-Aroylmethylene-indol-2-ones with Urea and Thiourea Derivatives", J Indian Chem Soc., (Nov. 1995) 72: 833-835.
Dandia et al., "Facile One Pot Microwave Induced Solvent-Free Synthesis and Antifungal, Antitubercular Screening of Spiro [1,5]-Benzothiazepin-2,3'[3'H]indol-2[1'H]-ones", Chem Pharm Bull (2003) 51(10): 1137-1141.
Database accession No. CID 359736, 3-[2-(4-Amino-phenyl)-2-oxo-ethyl]-3-hydroxy-1,3-dihydro-indol-2-one—Compound Summary; (Mar. 26, 2005) XP-002717179; Database PubChem Compound; pp. 1-5.

(56) References Cited

OTHER PUBLICATIONS

Database accession No. CID 326411; NSC297830—Compound summary; XP-002717181; (Mar. 26, 2004) Database PubChem Compound; pp. 1-5.
Database accession No. RN 362506-54-5; XP-002745329; (Oct. 16, 2001) Supplier: ChemBridge Corporation; 1 page.
Database accession No. RN 362507-29-7; XP-002745330; (Oct. 16, 2001) Supplier: Interbioscreen Ltd.; 1 page.
Database accession No. CID 366668, NSC635343—Compound summary; XP-002717180; (Mar. 26, 2005) Database PubChem Compound; pp. 1-3.
Database accession No. CID 366694, NSC635411—Compound summary; (Mar. 6, 2005) Database PubChem Compound; pp. 1-3.
Database accession No. CID 398900, NCI60_038544—Compound summary; (May 30, 2009) Database PubChem Compound; pp. 1-2.
Database accession No. CID 703160, ZINC00085926—Compound summary; (Jul. 8, 2005) Database PubChem Compound; pp. 1-2.
Database accession No. CID 772922, ZINC00257314—Compound summary; (Jul. 8, 2005) Database PubChem Compound; pp. 1-2.
Database accession No. CID 797457, ZINC00302255—Compound summary; (Jul. 9, 2005) Database PubChem Compound; pp. 1-2.
Database accession No. CID 797741, ZINC00302664—Compound summary; (Jul. 9, 2005) Database PubChem Compound; pp. 1-2.
Database accession No. CID 1149577, ZINC00894999—Compound summary; (Jul. 10, 2005) Database PubChem Compound; pp. 1-2.
Database accession No. RN 1144428-37-4; XP-002745331; (May 8, 2009) Supplier: Interbioscreen Ltd.; 1 page.
Database accession No. CID 1517002, ZINC01439946—Compound summary; (Jul. 11, 2005) Database PubChem Compound; pp. 1-2.
Database accession No. CID 51703682, ZINC35686355—Compound summary; (May 5, 2011) Database PubChem Compound; pp. 1-2.
Delattre et al., "The Ewing family of tumors—a subgroup of small-round-cell tumors defined by specific chimeric transcripts", N Engl J Med (1994) 331(5):294-299.
Demichelis et al., TMPRSS2: ERG gene fusion associated with lethal cancer in a watchful waiting cohort, Oncogene (2007) 26:4596-4599.
Derossi et al., "The third helix of the Antennapedia homeodomain translocates through biological membranes", J Biol Chem (1994) 269(14):10444-10450.
El-Gendy et al., "Synthesis and Antimicrobial Activity of some New 2-Indolinone Derived Oximes and Spiro-Isoxazolines," Arch Pharm Res 23(4):310-314 (2000).
Erkizan et al., "A small molecule blocking oncogenic protein EWS-FLI1 interaction with RNA helicase A inhibits growth of Ewing's sarcoma", Nat Med. (2009) 15(7): 750-756.
Feldmann et al., "Blockage of hedgehog signaling inhibits pancreatic cancer invasion and metastases: A new paradigm for combination therapy in solid cancers", Cancer Res. (2007) 67:2187-2196.
Frangioni et al., "Use of a general purpose mammalian expression vector for studying intracellular protein targeting: identification of critical residues in the nuclear lamin A/C nuclear localization signal", J Cell Sci (1993) 105(Pt. 2):481-488.
French et al., "Midline carcinoma of children and young adults with NUT rearrangement", J Clin Oncol (2004) 22(20):4135-4139.
Fujii et al., "An antagonist of dishevelled protein-protein interaction suppresses beta-catenin-dependent tumor cell growth", Cancer Res (2007) 67(2):573-579.
Gadek et al., "Small molecule antagonists of proteins", Biochem Pharmacol (2003) 65(1):1-8.
Gangwal et al., "Microsatellites as EWS/FLI response elements in Ewing's sarcoma", Proc Natl Acad Sci U S A (2008) 105(29):10149-10154.
Garden et al., "A versatile synthetic methodology for the synthesis of tryptophols", Tetrahedron (2002) 58(42):8399-8412.

Grier et al., "Addition of ifosfamide and etoposide to standard chemotherapy for Ewing's sarcoma and primitive neuroectodermal tumor of bone", N Engl J Med (2003) 348(8):694-701.
Grigg et al., "Siler Acetate Catalysed Cycloadditions of Isocyanoacetates," Tetrahedron 55:2025-2044 (1999).
Golub et al., "Molecular Classsification of Cancer: Class Discovery and Class Prediction by Gene Expression Monitoring", Science (1999) 286: 531-537.
Guo et al., "Quinidine Thiourea-catalyzed Aldol Reaction of Unactivated Ketones: Highly Enantioselective Synthesis of 3-Alkyl-3-hyroxy-indolin-2-ones," Angew Chem Int Ed 49:9460-9464 (2010).
Gupta et al., "Ordered short channel mesoporous silica modified with 1,3,5-triazine-piperazine as a versatile recyclable basic catalyst for cross-aldol, Knoevenagel and conjugate addition reactions with isatins", RSC advances, (2015) 5(23): 17843-17850.
Gyurkocza et al., "Antileukemic activity of shepherdin and molecular diversity of hsp90 inhibitors", J Natl Cancer Inst (2006) 98(15):1068-1077.
Hartman et al., "RNA helicase A is necessary for translation of selected messenger RNAs", Nat Struct Mol Biol. (2006) 13:509-516.
Helman et al., "Mechanisms of sarcoma development", Nat Rev Cancer (2003) 3(9):685-694.
Hu-Lieskovan et al., "Sequence-specific knockdown of EWS-FLI1 by targeted, nonviral delivery of small interfering RNA inhibits tumor growth in a murine model of metastatic Ewing's sarcoma", Cancer Res (2005) 65:8984-8992.
Ibrahim et al., "Synthesis of Spiro Heterocyclic Compounds", E-Journal of Chem. (2010) 7(1):55-58.
Iost et al., "mRNAs can be stabilized by DEAD-box proteins", Nature (1994) 372(6502):193-196.
IUPAC-IUB [Inter'l Union of Pure and Applied Chemistry—Inter'l Union of Biochemistry} Commission of Biochemical Nomenclature. Appreviated nomenclature of synthetic polypeptides (polymerized amino acids). Revised Recommentations (1971); Biochem. (1972) 11(5):942-944.
Joshi et al., "Synthesis and central nervous system activities of certain fluorine-containing 3-substituted indol-2-ones." Pharmazie (1984) 39(3): 153-155.
Joshi et al., "Studies in Spiro Hetercycles: Part 4: Investigation of the Reactions of Fluroinated 3-Aroylmethylene-indol-2-ones with Hydrazine and Phenylhydrazine and Synthesis of Spiro [indole3,3'-pyrazol]-2-ones," Pharmazle 40:21-22 (1985).
Joshi et al., "Studies in Spiroheterocycles: Part XXVIII: Investigation of the Reaction of 3-Aroylmethyleneindolin-2-Ones with Thiosemicarbazide and Synthesis of SPRIO[3H-Indole-3,4'(3'H)-Pyrimidin]-2(1H)-Ones," Heterocycles 31(3):473-477 (1990).
Joshi et al., "Investigation of the reaction of 1,3-dihydro-3-(20phenyl-2-oxoethylidene)-indol-2(H)-ones with 3-amino-1-phenyl-2-pyrazolin-5-one," Indian J Chem 29B:933-936 (1990).
Joshi et al., "Synthesis and Antibacterial Activity of some Novel Fluorine containing Sipro[3H-indole-3,3'-'3H]-pyrazol]-2(IH)-one Derivatives," J Indian Chem Soc 67:753-756 (1990).
Kaiser, J., "First Pass at Cancer Genome Reveals Complex Landscape", Sciene (2006) 313:1370.
Khan et al., "Classification and diagnostic prediction of cancers using gene expression profiling and artificial neural networks", Nat Med (2001) 7(6):673-679.
Kidwai et al., "Microwave-induced "solvent-free" novel technique for the synthesis of spiro [indole-pyrazole/isoxazole/pyrimidine] derivatives", Oxidation Communications (2001) 24(2): 287-290.
Kinsey et al., "NR0B1 is required for the oncogenic phenotype mediated by EWS/FLI in Ewing's sarcoma", Mol Cancer Res (2006) 4(11):851-859.
Klöck et al., "Acylideneoxoindoles: A new class of reversible inhibitors of human transglutaminase 2," J Bioorg Med Chem Lett. 21:2692-2696 (2011).
Knoop et al., "The splicing factor U1C represses EWS/FLI-mediated transactivation", J Biol Chem (2000) 275(32):24865-24871.
Knoop et al., "EWS/FLI alters 5'-splice site selection", J Biol Chem (2001) 276(25):22317-22322.

(56) References Cited

OTHER PUBLICATIONS

Kobayashi et al., "Studies on Indole Derivatives—Synthesis of 3-Phenyl-9H-pyridazino[3,4-b]indole Derivatives", Chem Pharm Bull. (1964) 12(10):1129-1135.
Kovar et al., "EWS/FLI-1 antagonists induce growth inhibition of Ewing tumor cells in vitro", Cell Growth Differ (1996) 7(4):429-437.
Kovar et al., "Potentials for RNAi in sarcoma research and therapy: Ewing's sarcoma as a model", Semin Cancer Biol. (2003) 13:275-281.
Krontiris et al., "Internal Medicine", 4th Edition, Elsevier Science (1994) Chapters 71-72, pp. 699-729.
Lala et al., "Role of nitric oxide in tumor progression: Lessons from experimental tumors", Cancer Metastasis Rev. (1998) 17(1): 91-106.
Lambert et al., EWS FLI-1 antisense nanocapsules inhibits Ewing sarcoma-related tumor in mice, Biochem Biophys Res Commun. (2000) 279(2):401-406.
Lang et al., "Identification of peptide mimetics of xenoreactive alpha-Gal antigenic epitope4 by phage display", Biochem Biophys Res Commun (2006) 306:27-66.
Lee et al., "RNA helicase A is essential for normal gastrulation", Proc Natl Acad Sci U S A (1998) 95(23):13709-13713.
Leeson et al., "The influence of drug-like concepts on decision-making in medicinal chemistry", Nature reviews (2007) 6(11):881-890.
Lenz et al., "Molecular subtypes of diffuse large B-cell lymphoma arise by distinct genetic pathways", PNAS (2008) 105(36): 13520-13525.
Lessnick et al., "The Ewing's sarcoma oncoprotein EWS/FLI induces a p53-dependent growth arrest in primary human fibroblasts", Cancer Cell (2002) 1(4):393-401.
Li et al., "Control of apoptosis and mitotic spindle checkpoint by survivin", Nature (1998) 396(6711):580-584.
Lindgren et al., "Translocation properties of novel cell penetrating transportan and penetratin analogues", Bioconjug Chem (2000) 11(5):619-626.
Liu et al., "Organocatalytic asymmetric synthesis of 3-difluoroalkyl 3-hyrdrozyoxindoles" Chem Commun. 48:1919-1921 (2012).
López-Alvarado et al., "New Diastereoselective Synthesis of 3-Alkyidene-1-methyloxindoles" Synthesis 1:104-110 (2002).
Lu et al., "Synthesis of planar chiral [2.2] paracyclophane-based amino thioureas and their application in asymmetric aldol reactions of ketones with isatins" Tetrahetron 24:1082-1088 (2013).
Lutz et al., "Acid-Catalyzed Rearrangements of the y-(Methylanilino)lactone of cis-B(p-Bromobenzoyl)-B-methylacrylic Acid, and of trans-b-(p-Bromobenzoyl)acrykuc Methylanilide, to Oxindoles," J Organ Chem. 25(1):193-196 (1960).
Macaev et al., "Synthesis and Structure of New Oxoindoles," Chem Hetero Compounds. 43(3):298-305 (2007).
Maitra et al., "Detection of t(11;22)(q24;q12) Translation and EWS-FLI-1 Fusion Transcript in a Case of Solid Pseudopapillary Tumor of the Pancreas", Ped Develop Pathol. (2000) 3:603-605.
Maksimenko et al., "Oligonucleotides targeted against a junction oncogene are made efficient by nanotechnologies", Pharm Res (2003) 20(10):1565-1567.
Mateo-Lozano et al.; Rapamycin induces the fusion-type independent downregulation of the EWS/FLI-1 proteins and inhibits Ewing's sarcoma cell proliferation; Oncogene (2003) 22(58):9282-9287.
Maxim et al., "Action of Cyclohexyl Methyl Ketone on Isatin. Preparation of Cyclohexylcinchoninic Acid", Comptes Rendus de L'Academie des Sciences Roumanie (1946) 8:65-69; as shown in Accession No. 206828 entered Jun. 7, 1988; 9 pages.
May et al., "Ewing sarcoma 11;22 translocation produces a chimeric transcription factor that requires the DNA-binding domain encoded by FLI1 for transformation", Proc Natl Acad Sci U S A (1993) 90(12):5752-5756.
May et al., "The Ewing's sarcoma EWS/FLI-1 fusion gene encodes a more potent transcriptional activator and is a more powerful transforming gene than FLI-1", Mol Cell Biol (1993) 13(12):7393-7398.

McIntyre et al., "Design and cloning strategies for constructing shRNA expression vectors", BMC Biotechnol. (2006) 6:1.
Medlineplus; Cancer [online]; [retrieved on Jul. 6, 2007] URL— http://www.nlm.nik.gov/medlineplus/cancer.html. 10 pages.
Merchant et al., "Potential use of imatinib in Ewing's sarcoma: evidence for in vitro and in vivo activity", J Natl Cancer Inst (2002) 94(22):1673-1679.
Merchant et al., Interferon gamma enhances the effectiveness of tumor necrosis factor-related apoptosis—Inducing ligand receptor agonists in a xenograft model of Ewing's sarcoma., Cancer Res (2004) 64(22):8349-8356.
Mhawech-Fauceglia et al., "Friend leukaemia integration-1 expression in malignant and benign tumours: a multiple tumour tissue microarray analysis using polyclonal antibody", J Clin Path. (2007) 60(6):694-700.
Murray et al., "Targeting protein-protein interactions: Lessons from p53/MDM2", Biopolymers (2007) 88(5):657-686.
Myohanen et al., "Sequence-specific DNA binding activity of RNA helicase A to the p16INK4a promoter", J Biol Chem (2001) 276(2):1634-1642.
Nagle et al., "3-(2-Oxoethylidene)indolin-2-one Derivatives Activate Nrf2 and Inhibit NF-xB: Potential Candidates for Chemoprevention," ChemMedChem 9(8):1763-1774 (2014).
Nakajima et al., "RNA helicase A mediates assocation of CBP with RNA polymerase II", Cell (1997) 90(6):1107-1112.
Nakatani et al., "Identification of p21WAF1/CIP1 as a direct target of EWS-Fli1 oncogenic fusion protein", J Biol Chem (2003) 278(17):15105-15115.
National Center for Biotechnology Information. (PubChm Substance Database; SID=862348, (https://pubchem.ncbi.nlm.nih.gov/substance/862348; downloaded 1/2/207); available Jun. 29, 2005; 8 pages.
Ng et al., "Multiple aromatic side chains within a disordered structure are critical for transcription and transforming activity of EWS family oncoproteins", Proc Natl Acad Sci U S A (2007) 104(2):479-484.
Ojida et al., "Highly enantioselective reformatsky reaction of ketones: Chelation-assisted enantioface discrimination", Org Lett (2002) 4(18):3051-3054.
Ouchida et al., "Loss of tumorigenicity of Ewing's sarcoma cells expressing antisense RNA to EWS-fusion transcripts", Oncogene (1995) 11(6):1049-1054.
Pagliaro et al., "Emerging classes of protein-protein interaction inhibitors and new tools for their development", Curr Opin Chem Biol. (2004) 8(4):442-449.
Pajouhesh et al., "Potential Anticonvulsants VI: Condensation of Isatins with Cyclohexonone and Other Cyclic Ketones", J Pharma Sciences (1983) 72(3):318-321.
Palermo et al., "The AF4-mimetic peptide, PFWT, induces necrotic cell death in MV4-11 leukemia cells", Leuk Res. (2008) 32(4):633-42.
Perez et al., "Antennapedia homeobox as a signal for the cellular internalization and nuclear addressing of a small exogenous peptide", J Cell Sci (1992) 102(Pt. 4):717-722.
Petermann et al., "Oncogenic EWS-Fli1 interacts with hsRPB7, a subunit of human RNA polymerase II", Oncogene (1998) 17:603-610.
Pietra et al., "The stereochemistry of propiophenone addition to isatin," Gazzetta Chimica Italiana 92(XII): 1422-1431 (1962).
Plescia et al., "Rational design of shepherdin, a novel anticancer agent", Cancer Cell (2005) 7(5):457-468.
Popp et al., "Synthesis of 3-Hydroxy-3-phenacyloxindole Analogs", J Pharma Science (1979) 68(4):519-520.
Poppe et al., "Expression analyses identify MLL as a prominent target of 11q23 amplification and support an etiologic role for MLL gain of function in myeloid malignancies", Blood (2004) 103(1):229-235.
Pui et al., "Clinical heterogeneity in childhood acute lymphoblastic leukemia with 11q23 rearrangements", Leukemia (2003) 17(4):700-706.
Pui et al., "Acute lymphoblastic leukemia", N Engl J Med (2004) 350(15):1535-1548.

(56) References Cited

OTHER PUBLICATIONS

Rahim et al., "YK-4-279 Inhibits ERG and ETV1 Mediated Prostate Cancer Cell Invasion", PLoS One (2011) 6(4):e19343; 8 pages.
"Remington's Pharmaceutical Sciences", Mack Publishing Company 19th edition (1995).
Richter et al, "Diazepam-bound GABAA receptor models identify new benzodiazepine binding-site ligands," Nature 8:455-464 (2012).
Riggi et al., "Ewing's sarcoma-Like tumors originate from EWS-FLI-1-expressing mesenchymal progenitor cells", Cancer Res (2006) 66(19):9786.
Righetti et al., "Heterodiene Syntheses. Part 21. etc.". J Chem Soc., Perkin Transactions I, (1979) 4: 863-868.
RN 667914-27-4 (Registry, 2H-Indol-2-one, 3-[2-(4-aminophenyl)-2-oxoethyl]-5, 7-dichloro-1, 3-dihydro-3-hydroxy, Mar. 26, 2004); 1 page.
RN 667914-33-2 (Registry, 2H-Indol-2-one, 4, 7-dichloro-3-[2-(4-aminophenyl)-2-oxoethyl]-1, 3-dihydro-3-hydroxy, Mar. 26, 2004); 1 page.
RN 672338-27-1 (Registry, 2H-Indol-2-one, 4, 6-dichloro-1, 3-dihydro-3-hydroxy-3-[2-(3-nitrophenyl)-2-oxoehyl], Apr. 7, 2004); 1 page.
RN 6938523-27-7 (Registry, 2H-Indol-2-one, 7-bromo-1,3-dihydro-3-hydroxy-3-[2-(4-methoxyphenl)-2-oxoethyl]-5-methyl, Jun. 16, 2004); 1 page.
RN 848688-25-5 (Registry, 2H-Indol-2-one, 4,6-dichloro-3-[2-(2,4-dimethoxyphenyl)-2-oxoethyl]-1, 3-dihydro-3-hydroxy, Apr. 18, 2005); 1 page.
RN 900016-35-5 (Registry, 2H-Indol-2-one, 7-chloro-1, 3-dihydro-3-hydroxy-3-[2-oxo-2-(3,4,5-trimethoxphenyl) ethyl, Aug. 9, 2006); 1 page.
RN 909225-77-0 (Registry, 2H-Indol-2-one, 7-chloro-3-[2-(4-ethylphenyl)-2-oxoethyl]-1,3-hydroxy, Oct. 2, 2006); 1 page.
RN 692281-43-9 (Registry, 2H-Indol-2-one, 4-chloro-3-[2-(4-fluorophenyl)-2-oxoethyl]-1,3-dihydro-3-hydroxy-7-methyl, Jun. 13, 2004); 1 page.
RN 848755-10-2 (Registry, 2H-Indol-2-one4,6-dichloro-3-[2-(3,4-dimethoxyphenyl)-2-oxoethyl]-1,3-dihydro-3-hydroxy, Apr. 19, 2005); 1 page.
Registry File(STN), downloaded on Oct. 6, 2016; RN:1180038-32-7; 1146930-25-7; 1144428-37-4; 634174-66-6; 1144428-37-4; 634174-66-6; 442567-87-5; 421584-34-1; 421579-15-9; 421578-89-4; 385394-59-2; 383893-83-2; 370850-15-0; 370848-38-7; 369395-93-7; 362507-29-7, and 362506-54-5; 8 pages.
Registry File(STN), published Aug. 6, 2002, RN:442639-80-7; 1 page.
Saidalimu et al., "Highly Enantioselective Construction of 3-Hyrdoxy Oxindoles through a Decarboxylative Aldol Additional Trifluoromethyl a-Fluorinated gen-diols to N-Benzyl Isatins," Angew Chem Int. Ed. 52:5566-5570 (2013).
Sanchez et al., "Alteration of cyclin D1 transcript elongation by a mutated transcription factor up-regulates the oncogenic D1b splice isoform in cancer", Proc Natl Acad Sci U S A. (2008) 105(16):6004-6009.
Segura-Cabrera et al., "Structure-based prediction of *Mycobacterium tuberculosis* shikimate kinase inhibitors by high-throughput virtual screening," Bioorg Med Chem Lett. 18:3152-3157 (2008).
Selvanathan et al, "Oncogenic fusion protein EWS-FLI1 is a network hub that regulates alternative splicing", PNAS (Mar. 2015) E1307-1316.
Sillerud et al., "Design and structure of peptide and peptidomimetic antagonists of protein-protein interaction", Curr Protein Pept Sci (2005) 6(2):151-169.
Smith et al., "Expression profiling of EWS/FLI identifies NKX2.2 as a critical target gene in Ewing's sarcoma", Cancer Cell (2006) 9(5):405-416.
Snyder et al., "Treatment of terminal peritoneal carcinomatosis by a transducible p53-activating peptide", PLos Biol (2004) 2(2):0186-0193.
Srinivasan et al., "The synthetic peptide PFWT disrupts AF4-AF9 protein complexes and induces apoptosis in t(4;11) leukemia cells", Leukemia (2004) 18(8):1364-1372.

Stegmaier et al., "Signature-based small molecule screening identifies cytosine arabinoside as an EWS/FLI modulator in Ewing sarcoma", PLoS medicine (2007) 4(4):e122.
Strigacova et al., "Novel oxindole derivatives and their biological activity", Folia Microbiol (Praha). (2001) 46(3):187-192.
Subramanian et al., "Gene set enrichment analysis: a knowledge-based approach for interpreting genome-wide expression profiles", Proc Natl Acad Sci U S A. (2005) 102(43):15545-15550.
Tanaka et al., "EWS-FLI1 antisense oligodeoxynucleotide inhibits proliferation of human Ewing's sarcoma and primitive neuroectodermal tumor cells", J Clin Invest (1997) 99(2):239-247.
Terrone et al., "Penetratin and related cell-penetrating cationic peptides can translocate across lipid bilayers in the presence of a transbilayer potential", Biochem. (2003) 42(47):13787-13799.
Tetsuka et al., "RNA helicase A interacts with nuclear factor kappaB p65 and functions as a transcriptional coactivator", Eur J Biochem (2004) 271(18):3741-3751.
Thoren et al., "The antennapedia peptide penetratin translocates across lipid bilayers—the first direct observation", FEBS Lett (2000) 482(3):265-268.
Tiemann et al., "Solid pseudopapillary neoplasms of the pancreas are associated with FLI-1 expression, but not with EWS/FLI-1 translocation." Mod Pathol. (2006) 19(11):1409-1413.
Torchia et al., "EWS/FLI-1 induces rapid onset of myeloid/erythroid leukemia in mice", Mol Cell Biol (2007) 27(22):7918-7934.
Toretsky et al., "Inhibition of EWS/FLI-1 fusion protein with antisense oligodeoxynucleotides", J Neurooncol. (1997) 31(1-2):9-16.
Toretsky et al., "Phosphoinositide 3-hydroxide kinase blockade enhances apoptosis in the Ewing's sarcoma family of tumors", Cancer Res (1999) 59(22):5745-5750.
Toretsky et al., "Glypican-3 expression in Wilms tumor and hepatoblastoma", J Pediatr Hematol Oncol. (2001) 23(8):496-499.
Toretsky et al., "Oncoprotein EWS-FLI1 activity is enhanced by RNA helicase A", Cancer Res (2006) 66(11):5574-5581.
Üren et al., "Recombinant EWS-FLI1 oncoprotein activates transcription", Biochem. (2004) 43(42):13579-13589.
Üren et al., "Activation of the canonical Wnt pathway during genital keratinocyte transformation: a model for cervical cancer progression", Cancer Res (2005) 65(14):6199-6206.
Üren et al., "Ewing's Sarcoma Oncoprotein EWS-FLI1: The Perfect Target without a Therapeutic Agent", Future Onc. (2005) 1(4):521-528.
Üren et al., "Pediatric malignancies provide unique cancer therapy targets", Curr Opin Pediatr. (2005) 17:14-19.
Välineva et al., "Characterization of RNA helicase A as component of STAT6-dependent enhanceosome", Nucleic Acids Res (2006) 34(14):3938-3946.
Velikorodov et al., "Some Condensations of Methyl 4-Acetylphenylcarbamate", Russian J Org Chem (2010) 46(7):971-975.
Velikorodov et al., "Synthesis of New Spiro Compounds Containing a Carbamate Group", Russian J Org Chem. (2010) 46(12):1826-1829.
Velikorodov et al., "Synthesis of 3-Pyrrol-3'-yloxindoles with a Carbamate Function", Russian J Org Chem. (2011) 47(11):1715-1717.
Velikorodov et al., "L-Proline-Catalyzed 1,3-Dipolar Cycloaddition of Some Schiff Bases to Methyl 4-[1-Oxo-2(2-Oxo-2,3-dihydro1H-indol-3-ylidene)ethyl]phenylcarbamate", Russian J Org Chem. (2011) 47(10):1596-1597.
Velikorodov et al., "Three-Component Synthesis of Spiro Compounds with a Carbamate Functionality", Russian J Org Chem. (2011) 47(3):402-404.
Von Hippel et al., "A general model for nucleic acid helicases and their "coupling" within macromolecular machines", Cell (2001) 104(2):177-190.
Walensky et al., "Activation of apoptosis in vivo by a hydrocarbon-stapled BH3 helix", Science (2004) 305(5689):1466-1470.
Wikipedia—Cancer [online]; [retrieved on Jul. 6, 2007]. URL; http://en.wikipedia.org/wiki/Cancer; 2 pages.

(56) References Cited

OTHER PUBLICATIONS

Xie et al., "Functional anthology of intrinsic disorder. 1. Biological processes and functions of proteins with long disordered regions", J Proteome Res. (2007) 6(5):1882-1898.

Yang et al, "Exploiting Synthetic Lethality for the Therapy of ABC Diffuse Large B Cell Lymphoma", Cancer Cell (2012) 21(6): 723-737.

Yin et al., "Low molecular weight inhibitors of Myc-Max interaction and function", Oncogene (2003) 22(40):6151-6159.

Yong et al., "Synthesis of novel 3'-spirocycline-oxindole derivatives and assessment of their cytostatic activities", Tetrahedron (2007) 63(25): 5579-5586.

Yu et al., "Highly Efficient 'On Water' Catalyst-Free Neucleophilic Addition Reactions Using Difluoroenoxysilanes: Dramatic Flourine Effects," Angew Chem Int. Ed 53:9512-9516 (2014).

Zhang et al., "Multiple functions of nuclear DNA helicase II (RNA helicase A) in nucleic acid metabolism", Acta Biochim Biophys Sin (Shanghai) (2004) 36(3):177-183.

Zhong et al., "RNA helicase A in the MEF1 transcription factor complex upregulates the MDR1 gene in multidrug-resistant cancer cells", J Biol Chem (2004) 279(17):17134-17141.

Zhong et al., "Molecular sieve mediated decarboxylative Mannich and aldol reactions of B-ketoacids," Tetrahedron Lett. 54:4333-4336 (2013).

STN Registry No. RN 309928-53-8 (Entered STN: Dec. 20, 2000) 1 page.

Spriano, et al., "The ETS inhibitors YK-4-279 and TK-216 are novel anti-lymphoma agents", downloaded from clincancerres.aacrjournals.org on Jun. 12, 2019. © 2019 American Association for Cancer, Author Manuscript Published OnlineFirst on Jun. 10, 2019; DOI: 10.1158/1078-0432.CCR-18-2718.

CAS Registry No. 1243177-50-5 entered: Sep. 28, 2010; "1H-Isoindole-1,3(2H)-dione, 2-[3-[2-(2,3-dihydro-3-hydroxy-2-oxo-1H-indol-3-yl)acetyl]phenyl]hexahydro-"; 1 Page.

CAS Registry No. 10491584-23-7 entered: Sep. 14, 2008; "2H-Indol-2-one, 1-butyl-3-[2-(4-cyclohexylphenyl)-2-oxoethyl]-1,3-dihydro-3-hydroxy-"; 1 Page.

CAS Registry No. 632292-67-2 entered: Dec. 30, 2003; "2H-Indol-2-one, 3-[2-(4-cyclohexylphenyl)-2-oxoethyl]-1-ethyl-1,3-dihydro-3-hydroxy-"; 1 Page.

CAS Registry No. 496949-07-6 entered: Mar. 5, 2003; "1H-Isoindole-1,3(2H)-dione, 2-[3-[2-(2,3-dihydro-3-hydroxy-1-methyl-2-oxo-1H-indol-3-yl)acetyl]phenyl]hexahydro-"; 1 Page.

CAS Registry No. 312504-22-6 entered: Jan. 2, 2001; "2H-Indol-2-one, 3-[2-(4-cyclohexylphenyl)-2-oxoethyl]-1,3-dihydro-3-hydroxy-1-methyl-"; 1 Page.

Kulimova et al., "Growth inhibition and induction of apoptosis in acute myeloid leukemia cells by new indolinone derivatives targeting fibroblast growth factor, platelet-derived growth factor, and vascular endothelial growth factor receptors", Mol Cancer Ther. (2006) 5(12): 3105-3112.

Makaev et al., "Simple synthesis of new chiral oxindole derivative." Russian Chemical Bulletin 57.7 (2008): 1571-1574.

International Search Report and Written Opinion dated Oct. 27, 2017 from corresponding PCT/2017/043979, filed Jul. 26, 2017.

* cited by examiner

USES OF INDOLINONE COMPOUNDS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/660,566, filed Jul. 26, 2017, which claims the benefit of U.S. Provisional Application No. 62/368,707, filed Jul. 29, 2016, U.S. Provisional Application No. 62/417,572, filed Nov. 4, 2016, U.S. Provisional Application No. 62/422,504, filed Nov. 15, 2016, U.S. Provisional Application No. 62/426,107, filed Nov. 23, 2016, U.S. Provisional Application No. 62/503,238, filed May 8, 2017, and U.S. Provisional Application No. 62/534,067, filed Jul. 18, 2017. Each of the aforementioned applications is incorporated by reference herein in its entirety, and each is hereby expressly made a part of this specification.

FIELD

Methods and compositions for treating acute myeloid leukemia and diffuse large B cell lymphoma using indolinone derivatives are provided.

BACKGROUND

The EWS-FLI transcription factor present in vast variety of Ewing's sarcoma family of tumors (ESFT) was characterized over ten years ago. Progress in the treatment of Ewing's sarcoma the second most common bone tumor in children and adolescents, has improved survival for patients with localized tumors. However, patients with metastases still fare badly and the therapy carries short and long-term toxicities. The Ewing sarcoma family of tumors (ESFT) is characterized by a chromosomal translocation that generates EWS-FLI1, on oncogenic fusion transcription factor whose continued expression is believed to be critical for ESFT cell survival (Balamuth, N J, Womer, R B., Lancet Oncology 11, 184-192 (2010)). ETS transcription factors, such as FLI1 and SPIB, are recurrently deregulated in human lymphomas (Bonetti et al, Blood 2013; Lenz et al, PNAS 2008). The small molecule YK-4-279 inhibits binding of EWS1-FLI1 fusion protein to RHA resulting in growth arrest and apoptosis in Ewing sarcoma cells (Erkizan et al, Nat Med 2009) and it was previously showed that YK-4-279 has in vitro anti-lymphoma activity (Chung et al, AACR 2015).

In vitro and in vivo studies have demonstrated that the inhibition of the binding of the oncoprotein, EWS-FLI1, to RNA Helicase A (RHA) leads to a decrease in proliferation of ESFT cell lines and a decrease of tumor volume. EWS-FLI1 lacks enzymatic activity, however, the protein-protein interaction between RNA helicase A (RHA) and EWS-FLI1-modulates oncogenesis, and is therefore required for the maintenance of the tumor growth (Hyariye N Erkizan et al. Nature Medicine 15(7) 750-756 (2009)). The paradigm of disrupting key protein interactions may have utility in treatment of diseases including sarcomas with similar translocations, and leukemias with MLL translocations ((Helman L J, Meltzer P. Mechanisms of sarcoma development. Nat Rev Cancer 2003; 3(9):685-94); and Pui C H, et al., N Engl J Med 2004; 350(15):1535-48). Moreover, disordered proteins may be excellent therapeutic targets based on their intrinsic biochemical properties (Cheng Y, LeGall T, Oldfield C J, et al., Trends Biotechnol 2006; 24(10):435-42).

SUMMARY

Despite years of in vitro and xenograft studies with antisense and siRNA directed towards EWS-FLI1, none of these is heretofore practical as a human therapy based on inadequate delivery and stability. Accordingly, there is a need for improved therapies to treat disorders such as ESFTs.

FLI-1 is a member of the ETS family transcription factors which are normally active in the developing embryo, but not after birth. There are 29 members of this family of transcription factors, four of which, FLI-1, ETV1, ETV4 and ERG, have been associated with a wide range of cancers.

Therapeutic compounds targeting the inhibition of the binding of oncogenic fusion proteins of FLI1, ETV1, ETV4 or ERG or the transcription factors themselves will have utility in treatment of cancers including the Ewing's sarcoma family of tumors, pancreatic cancer, prostate cancer, glioblastoma, non-small cell lung cancer, and several other cancers. The preferred embodiments fulfill these needs, and provide other advantages as well.

Some embodiments disclosed herein relate to a compound of Formula (I) including forms such as stereoisomers, free forms, pharmaceutically acceptable salts or esters thereof, solvates, or combinations of such forms, wherein A, D, $R_1$, $R_2$, $R_3$, $R_4$, $R_5$, $R_6$, and $R_{12}$ are as defined herein.

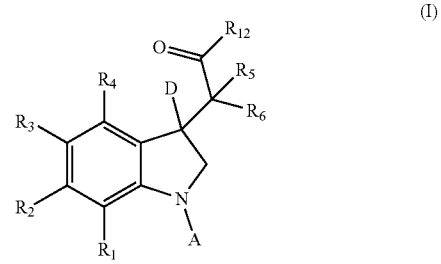

(I)

Some embodiments disclosed herein relate to methods for treating cancer in a mammal, comprising administering to the mammal an effective amount of one or more compounds of Formula (I) including forms such as stereoisomers, free forms, or a pharmaceutically acceptable salt thereof, or a pharmaceutical composition that includes one or more compounds of Formula (I) including forms such as stereoisomers, free forms, or a pharmaceutically acceptable salt thereof. Other embodiments described herein relate to using one or more compounds of Formula (I) including forms such as stereoisomers, free forms, or a pharmaceutically acceptable salt thereof, in the manufacture of a medicament for treatment of cancer.

Still other embodiments described herein relate to a compound of Formula (I) including forms such as stereoisomers, free forms, or a pharmaceutically acceptable salt thereof, for treatment of cancer wherein the cancer is selected from the group consisting of Ewing's sarcoma, glioblastoma, acute myeloid leukemia, breast cancer, head & neck cancer, melanoma, non-small cell lung cancer, ovarian cancer, prostate cancer, and uterine cancer. These and other embodiments are described in greater detail below.

DESCRIPTION OF THE DRAWINGS

FIG. 18A) Induction of apoptosis in DLBCL cell lines exposed to TK-216 (500 nM) for 24, 48 or 72 hrs. In the figures are shown four representative (two ABC and two GCB) results. FIG. 18B) Cell cycle distribution in DLBCL cell lines treated with 500 nM of TK-216 for 24, 48 or 72 hrs. In the figure, two representative (one ABC and one GCB) results are shown. DMSO treatment was used as a control.

DETAILED DESCRIPTION

Figure 1:
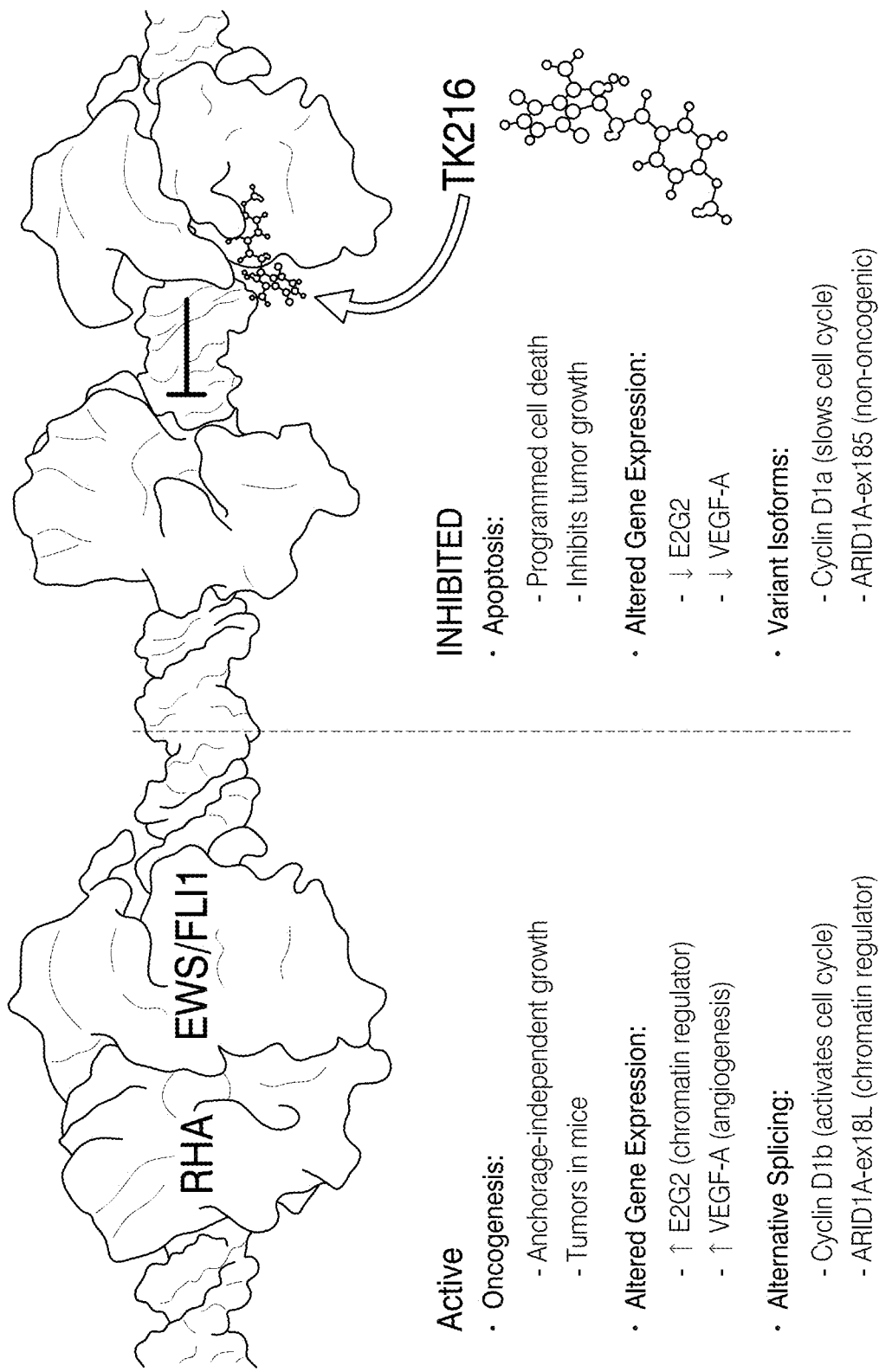
FIG. 1 is a diagram illustrating that TK216 (also referred to herein as TK-216, which is 4,7-Dichloro-3-(2-(4-cyclopropylphenyl)-2-oxoethyl)-3-hydroxyindolin-2-one) is active in oncogenesis and inhibits aptosis.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention Chromosomal translocations generating oncogenic transcription factors are the hallmark of a variety of tumors, including many sarcomas. Ewing sarcoma family of tumors (ESFTs) are characterized by the t(11;22)(q24;q12) translocation that generates the Ewing sarcoma breakpoint region 1 and Friend leukemia virus integration 1 (EWS-FLI1) fusion transcription factor responsible for the highly malignant phenotype of this tumor. Continued expression of EWS-FLI1 is believed to be critical for ESFT cell survival. EWS-FLI1 is an attractive treatment target for Ewing sarcoma because of its malignant cell specificity. Furthermore, experimental evidence indicates that EWS/FLI expression is essential for Ewing sarcoma tumor cells. In vitro targeting of EWS-FLI1 with antisense oligodeoxynucleotides and RNA interference (RNAi) inhibits Ewing sarcoma cell viability, growth, and oncogenic transformation, supporting EWS-FLI1 attenuation as a potential treatment modality. The therapeutic agents of the preferred embodiments have broad applicability to a larger group of tumors, and are useful as therapeutics for treatment for other oncogenic transcription factor related malignancies such as chemotherapy-resistant sarcomas and leukemias and difficult to treat tumors such as Ewing's sarcoma.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there is a plurality of definitions for a term herein, those in this section prevail unless stated otherwise.

As used herein, any "R" group(s) such as, without limitation, $R_1$, $R_2$, $R_3$, $R_4$, $R_5$, $R_6$, $R_7$, $R_8$, $R_9$, $R_{10}$, $R_{11}$, and $R_{12}$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

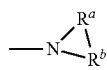

In addition, if two "R" groups are described as being "taken together" with the atom(s) to which they are attached to form a ring as an alternative, the R groups may not be limited to the variables or substituents defined previously.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_6$ alkyl" or similar designations. By way of example only, "$C_1$-$C_6$ alkyl" indicates that there are one to six carbon atoms in the alkyl chain, i.e., the alkyl chain is selected from methyl, ethyl, propyl, iso-propyl, n-butyl, iso-butyl, sec-butyl, and t-butyl, pentyl (straight and branched) and hexyl (straight and branched). Typical alkyl groups include, but are in no way limited to, methyl, ethyl, propyl, isopropyl, butyl, isobutyl, tertiary butyl, pentyl (straight and branched) and hexyl (straight and branched). The alkyl group may be substituted or unsubstituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "aryl" refers to a carbocyclic (all carbon) mono-cyclic or multi-cyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a mono-cyclic or multi-cyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2, 3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, heterocycloalkyl refers to three-, four-, five-, six-, seven-, eight-, nine-, ten-, up to 18-membered mono-cyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocycloalky may be quaternized. Heterocycloalkyl groups may be unsubstituted or substituted. Examples of such heterocycloalkyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline and 3,4-methylenedioxyphenyl).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Methods of Treatment

In a first aspect, a method for inducing aptosis in a cell comprising a myeloblast produced in acute myeloid leukemia or a lymphocyte produced in diffuse large B cell lymphoma, comprising contacting the cell with an effective amount of a combination of venetoclax and a compound having a structure of Formula (I):

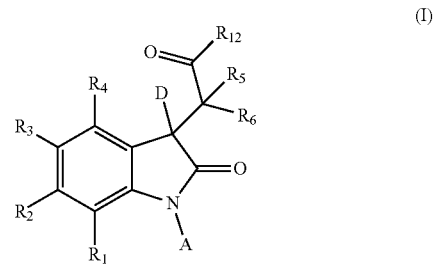

or a stereoisomer, a pharmaceutically acceptable salt, or solvate thereof, wherein $R_1$, $R_2$, $R_3$, and $R_4$ are independently selected from the group consisting of H, Cl, —CN and —CF$_3$; wherein A is selected from the group consisting of H and $C_{1-6}$ alkyl; wherein D is selected from the group consisting of —OH and —O($C_{1-6}$ alkyl); wherein $R_5$ and $R_6$ are independently selected from the group consisting of H, F, and $C_{1-6}$ alkyl, or wherein $R_5$ and $R_6$ taken together form a substituted or unsubstituted cycloalkyl ring; wherein $R_{12}$ is independently selected from the group consisting of $C_{3-8}$ cycloalkyl and

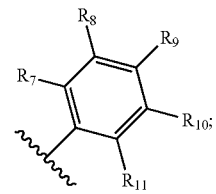

wherein $R_7$, $R_8$, $R_9$, $R_{10}$ and $R_{11}$ are independently selected from the group consisting of H, halogen, CN, CF$_3$, $C_{1-6}$ alkyl, aryl, heteroaryl, —O($C_{1-6}$ alkyl), —O(aryl), —O(heteroaryl), —CO$_2$H, —CO$_2$($C_{1-6}$ alkyl), —NHSO$_2$($C_{1-6}$ alkyl), —NHSO$_2$(aryl), —NHCONH($C_{1-6}$ alkyl), —NHCON($C_{1-6}$ alkyl)$_2$, —N($C_{1-6}$ alkyl)CONH$_2$, —N($C_{1-6}$ alkyl)CONH($C_{1-6}$ alkyl), —N($C_{1-6}$ alkyl)CON($C_{1-6}$ alkyl)$_2$, —SO$_2$($C_{1-6}$ alkyl), —SO$_2$NH$_2$, —SO$_2$NH($C_{1-6}$ alkyl), —SO$_2$N($C_{1-6}$ alkyl)$_2$, $C_{3-8}$ cycloalkyl, and $C_{3-8}$ heterocyloalkyl.

In an embodiment of the first aspect, $R_9$ is selected from the group consisting of H, halogen, CN, CF$_3$, $C_{1-6}$ alkyl, aryl, heteroaryl, —O(aryl), —O(heteroaryl), —CO$_2$H, —CO$_2$($C_{1-6}$ alkyl), —NHSO$_2$($C_{1-6}$ alkyl), —NHSO$_2$(aryl), —NHCONH($C_{1-6}$ alkyl), —NHCON($C_{14}$ alkyl)$_2$, —N($C_{1-6}$ alkyl)CONH$_2$, —N($C_{1-6}$ alkyl)CONH($C_{1-6}$ alkyl), —N($C_{1-6}$ alkyl)CON($C_{1-6}$ alkyl)$_2$, —SO$_2$($C_{1-6}$ alkyl), —SO$_2$NH$_2$, —SO$_2$NH($C_{1-6}$ alkyl), —SO$_2$N($C_{1-6}$ alkyl)$_2$, $C_{3-8}$ cycloalkyl, and $C_{3-8}$ heterocycloalkyl.

In an embodiment of the first aspect, the cell is mammalian.

In an embodiment of the first aspect, the cell is human.

In an embodiment of the first aspect, the cell is in vitro.

In an embodiment of the first aspect, the cell is in vivo.

In a second aspect, a method of treating acute myeloid leukemia or diffuse large B cell lymphoma is provided, comprising administering to a patient in need thereof an anti-proliferative amount of a combination of venetoclax and a compound having a structure of Formula (I):

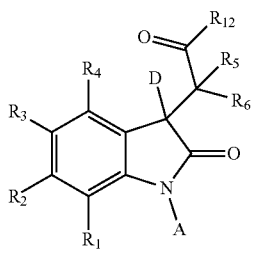

(I)

or a stereoisomer, a pharmaceutically acceptable salt, or solvate thereof, wherein $R_1$, $R_2$, $R_3$, and $R_4$ are independently selected from the group consisting of H, Cl, —CN and —CF$_3$; wherein A is selected from the group consisting of H and $C_{1-6}$ alkyl; wherein D is selected from the group consisting of —OH and —O($C_{1-6}$ alkyl); wherein $R_5$ and $R_6$ are independently selected from the group consisting of H, F, and $C_{1-6}$ alkyl, or wherein $R_5$ and $R_6$ taken together form a substituted or unsubstituted cycloalkyl ring; wherein $R_{12}$ is independently selected from the group consisting of $C_{3-8}$ cycloalkyl and

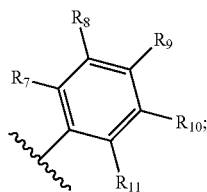

wherein $R_7$, $R_8$, $R_9$, $R_{10}$ and $R_{11}$ are independently selected from the group consisting of H, halogen, CN, CF$_3$, $C_{1-6}$ alkyl, aryl, heteroaryl, —O($C_{1-6}$ alkyl), —O(aryl), —O(heteroaryl), —CO$_2$H, —CO$_2$($C_{1-6}$ alkyl), —NHSO$_2$($C_{1-6}$ alkyl), —NHSO$_2$(aryl), —NHCONH($C_{1-6}$ alkyl), —NHCON($C_{1-6}$ alkyl)$_2$, —N($C_{1-6}$ alkyl)CONH$_2$, —N($C_{1-6}$ alkyl)CONH($C_{1-6}$ alkyl), —N($C_{1-6}$ alkyl)CON($C_{1-6}$ alkyl)$_2$, —SO$_2$(Cl$_6$ alkyl), —SO$_2$NH$_2$, —SO$_2$NH($C_4$ alkyl), —SO$_2$N($C_{1-6}$ alkyl)$_2$, $C_{3-8}$ cycloalkyl, and $C_{3-8}$ heterocycloalkyl.

In an embodiment of the second aspect, $R_9$ is selected from the group consisting of H, CN, CF$_3$, $C_{1-6}$ alkyl, aryl, heteroaryl, —O(aryl), —O(heteroaryl), —CO$_2$H, —CO$_2$($C_{1-6}$ alkyl), —NHSO$_2$($C_{1-6}$ alkyl), —NHSO$_2$(aryl), —NHCONH($C_{1-6}$ alkyl), —NHCON($C_{1-6}$ alkyl)$_2$, —N($C_{1-6}$ alkyl)CONH$_2$, —N($C_{1-6}$ alkyl)CONH($C_{1-6}$ alkyl), —N($C_{1-6}$ alkyl)CON($C_{1-6}$ alkyl)$_2$, —SO$_2$($C_{1-6}$ alkyl), —SO$_2$NH$_2$, —SO$_2$NH($C_{1-6}$ alkyl), —SO$_2$N($C_{1-6}$ alkyl)$_2$, $C_{3-8}$ cycloalkyl, and $C_{3-8}$ heterocycloalkyl.

In a third aspect, use is provided of a combination of venetoclax and a compound having a structure of Formula (I):

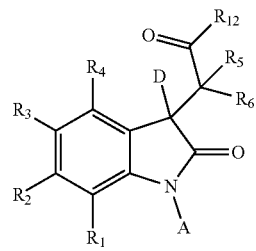

(I)

or a stereoisomer, a pharmaceutically acceptable salt, or solvate thereof, for the treatment of acute myeloid leukemia or diffuse large B cell lymphoma, wherein $R_1$, $R_2$, $R_3$, and $R_4$ are independently selected from the group consisting of H, Cl, —CN and —CF$_3$; wherein A is selected from the group consisting of H and $C_{1-6}$ alkyl; wherein D is selected from the group consisting of —OH and —O($C_{1-6}$ alkyl); wherein $R_5$ and $R_6$ are independently selected from the group consisting of H, F, and $C_{1-6}$ alkyl, or wherein $R_5$ and $R_6$ taken together form a substituted or unsubstituted cycloalkyl ring; wherein $R_{12}$ is independently selected from the group consisting of substituted or unsubstituted $C_{3-8}$ cycloalkyl, substituted or unsubstituted $C_{3-8}$ heterocycloalkyl,

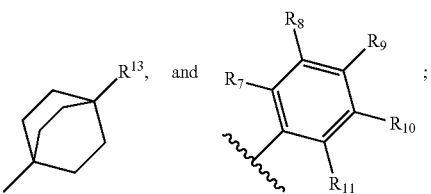

wherein $R_7$, $R_8$, $R_9$, $R_{10}$ and $R_{11}$ are independently selected from the group consisting of H, halogen, CN, CF$_3$, $C_{1-6}$ alkyl, aryl, heteroaryl, —O($C_{1-6}$ alkyl), —O(aryl), —O(heteroaryl), —CO$_2$H, —CO$_2$($C_{1-6}$ alkyl), —NHSO$_2$($C_{1-6}$ alkyl), —NHSO$_2$(aryl), —NHCONH($C_{1-6}$ alkyl), —NHCON($C_{1-6}$ alkyl)$_2$, —N($C_{1-6}$ alkyl)CONH$_2$, —N($C_{1-6}$ alkyl)CONH($C_{1-6}$ alkyl), —N($C_{1-6}$ alkyl)CON($C_{1-6}$ alkyl)$_2$, —SO$_2$($C_{1-6}$ alkyl), —SO$_2$NH$_2$, —SO$_2$NH($C_{1-6}$ alkyl), —SO$_2$N ($C_{1-6}$ alkyl)$_2$, $C_{3-8}$ cycloalkyl, and $C_{3-8}$ heterocycloalkyl; and wherein $R^{13}$ selected from the group consisting of —O($C_{1-6}$ alkyl) and —N($C_{1-6}$ alkyl)$_2$.

In an embodiment of the third aspect, $R_9$ is selected from the group consisting of H, halogen, CN, CF$_3$, $C_{1-6}$ alkyl, aryl, heteroaryl, —O(aryl), —O(heteroaryl), —CO$_2$H, —CO$_2$($C_{1-6}$ alkyl), —NHSO$_2$($C_{1-6}$ alkyl), —NHSO$_2$(aryl), —NHCONH($C_{1-6}$ alkyl), —NHCON($C_{1-6}$ alkyl)$_2$, —N($C_{1-6}$ alkyl)CONH$_2$, —N($C_{1-6}$ alkyl)CONH($C_{1-6}$ alkyl), —N($C_{1-6}$ alkyl)CON($C_{1-6}$ alkyl)$_2$, —SO$_2$($C_{1-6}$ alkyl), —SO$_2$NH$_2$, —SO$_2$NH($C_{1-6}$ alkyl), —SO$_2$N($C_{1-6}$ alkyl)$_2$, $C_{3-8}$ cycloalkyl, and $C_{3-8}$ heterocycloalkyl.

In an embodiment of the first aspect, $R_{12}$ is unsubstituted, or substituted by a halogen, e.g., Cl or F.

In an embodiment of the first aspect, the second aspect, or the third aspect, $R_9$ is selected from the group consisting of aziridinyl, azetidinyl, pyrrolidinyl, and morpholinolyl.

In an embodiment of the first aspect, the second aspect, or the third aspect, $R_9$ is selected from the group consisting of isopropyl and cyclopropyl.

In an embodiment of the first aspect, the second aspect, or the third aspect, the compound has a structure of Formula (Ia):

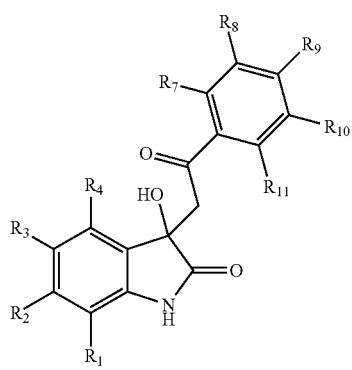

(Ia)

or a stereoisomer, a pharmaceutically acceptable salt, or solvate thereof, wherein $R_1$, $R_2$, $R_3$, and $R_4$ are independently selected from the group consisting of H and Cl; wherein $R_7$, $R_8$, $R_{10}$ and $R_{11}$ are independently selected from the group consisting of H and halogen; and wherein $R_9$ is independently selected from the group consisting $C_{3-8}$ cycloalkyl and $C_{3-8}$ heterocycloalkyl.

In an embodiment of the first aspect, the second aspect, or the third aspect, $R_1$ and $R_4$ are Cl and $R_2$ and $R_3$ are H.

In an embodiment of the first aspect, the second aspect, or the third aspect, the compound has a structure selected from the group consisting of:

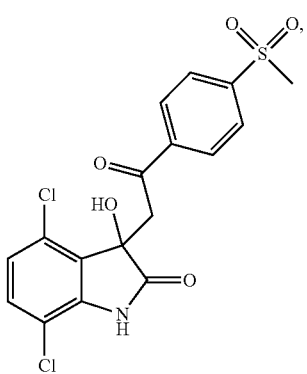

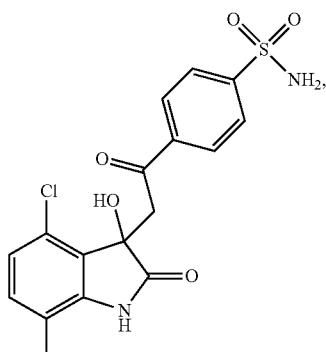

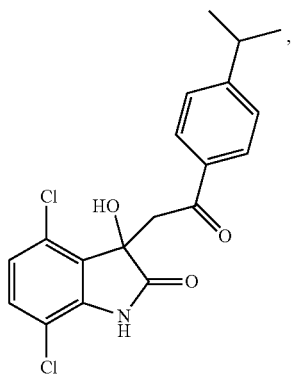

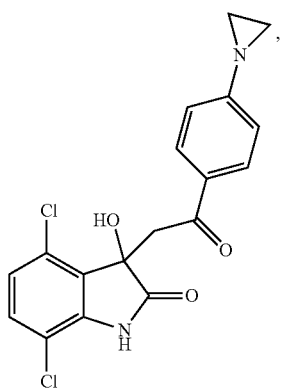

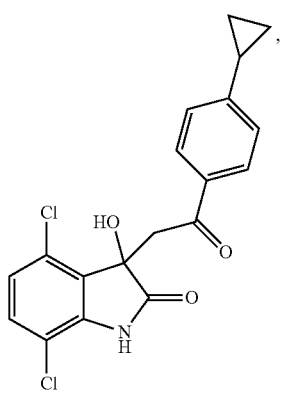

-continued
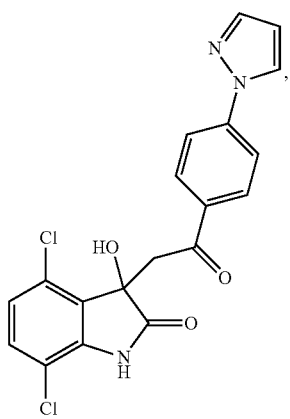
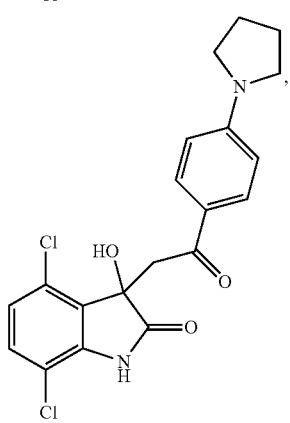
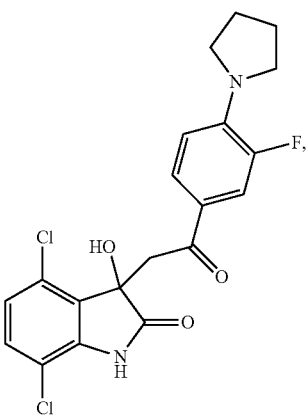
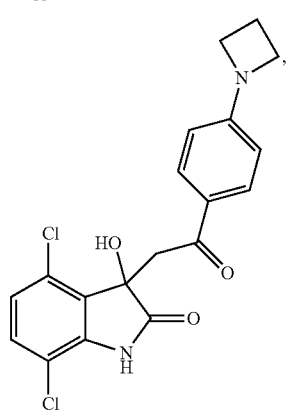
-continued
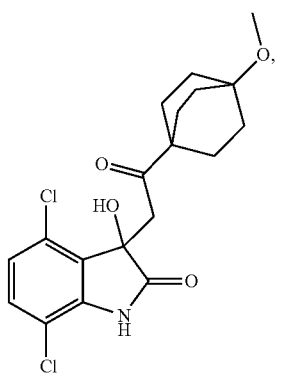
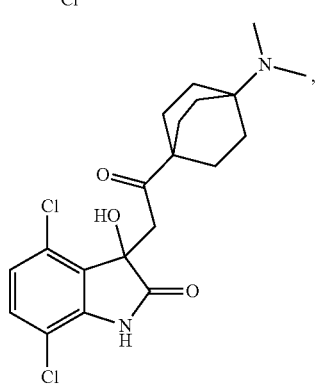
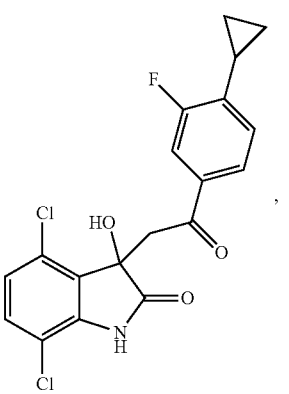
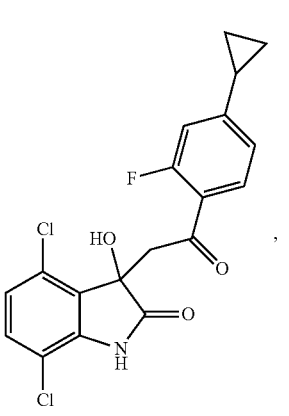

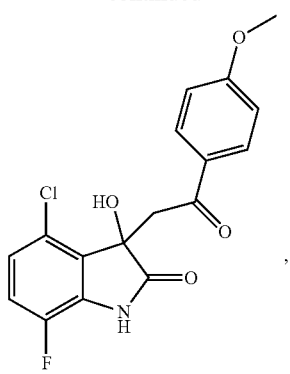
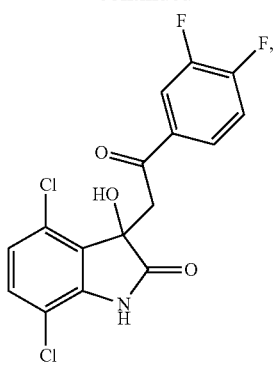
or a stereoisomer, a pharmaceutically acceptable salt, ester, or solvate thereof.
In an embodiment of the first aspect, the second aspect, or the third aspect, the compound is selected from the group consisting of:

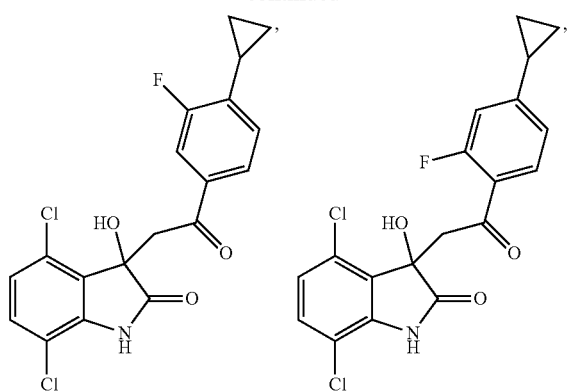

or a stereoisomer, a pharmaceutically acceptable salt, ester, or solvate thereof.

The method of any one of claims 1-6, wherein the compound has a structure selected from the group consisting of:

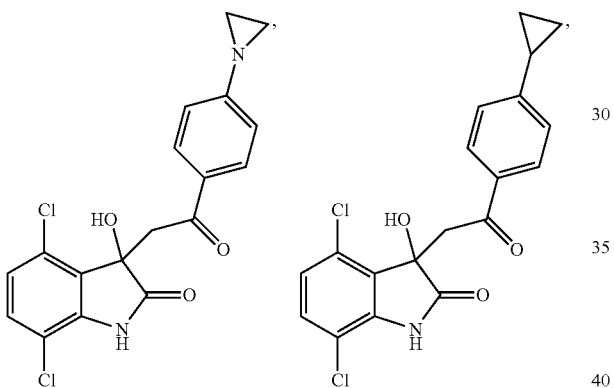

or a stereoisomer, a pharmaceutically acceptable salt, ester, or solvate thereof.

In an embodiment of the first aspect, the second aspect, or the third aspect, the compound has a structure selected from the group consisting of:

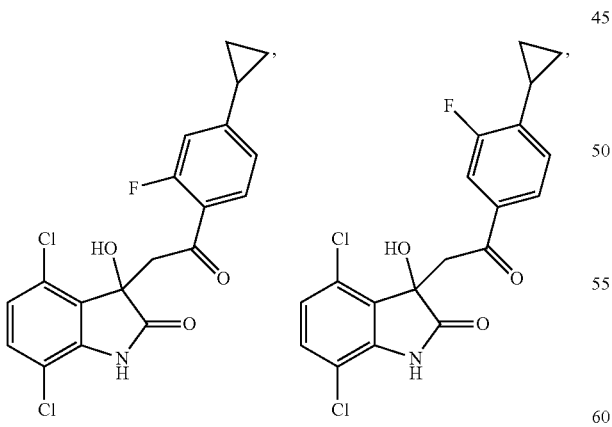

or a stereoisomer, a pharmaceutically acceptable salt, ester, or solvate thereof.

In an embodiment of the first aspect, the second aspect, or the third aspect, the compound has a structure:

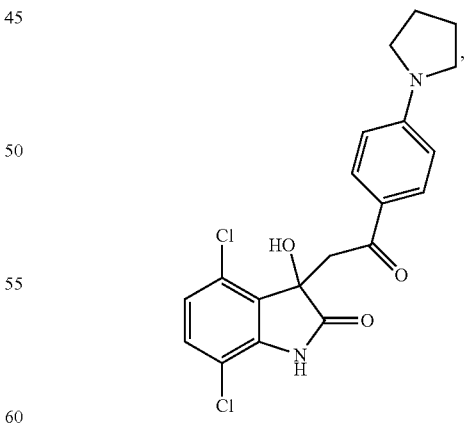

or a stereoisomer, a pharmaceutically acceptable salt, ester, or solvate thereof.

In an embodiment of the first aspect, the second aspect, or the third aspect, the compound has a structure:

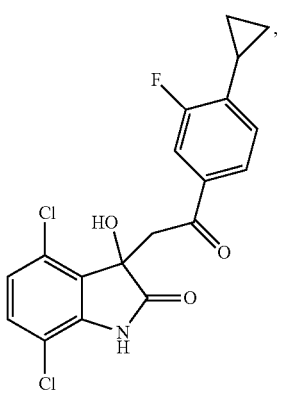 [SMILES: O=C(CC1(O)C(=O)Nc2c(Cl)ccc(Cl)c21)c1ccc(C2CC2)c(F)c1]

or a stereoisomer, a pharmaceutically acceptable salt, ester, or solvate thereof.

In an embodiment of the first aspect, the second aspect, or the third aspect, the compound has a structure:

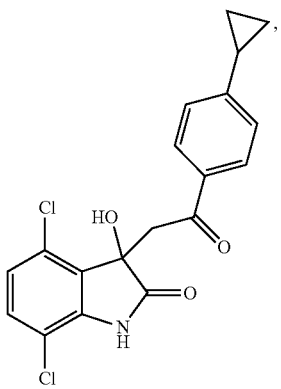 [SMILES: O=C(CC1(O)C(=O)Nc2c(Cl)ccc(Cl)c21)c1ccc(C2CC2)cc1]

or a stereoisomer, a pharmaceutically acceptable salt, ester, or solvate thereof.

Synthetic Methods

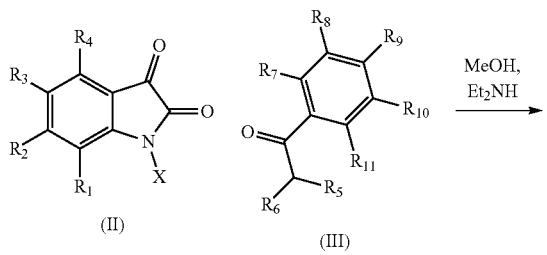

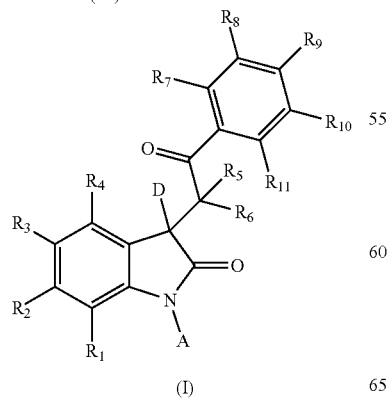

(I)

Compounds of Formula (I) described herein may be prepared in various ways. General synthetic routes to compounds of Formula (I) are shown and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Depending upon the substituents present, the small molecule inhibitors can be in a form of a pharmaceutically acceptable salt. The terms "pharmaceutically acceptable salt" as used herein are broad terms, and is to be given its ordinary and customary meaning to a person of ordinary skill in the art (and is not to be limited to a special or customized meaning), and refers without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity.

The compounds of preferred embodiments can include isomers, racemates, optical isomers, enantiomers, diastereomers, tautomers, and cis/trans conformers. All such isomeric forms are included within preferred embodiments, including mixtures thereof. As discussed above, the compounds of preferred embodiments may have chiral centers, for example, they may contain asymmetric carbon atoms and may thus exist in the form of enantiomers or diastereoisomers and mixtures thereof, e.g., racemates. Asymmetric carbon atom(s) can be present in the (R)- or (S)-configuration, or can be present as mixtures of the (R)- and (S)-forms. The following are isomeric forms of the compounds of Formula (I):

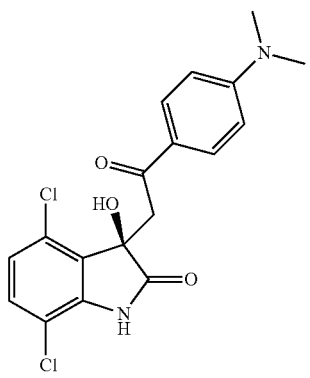

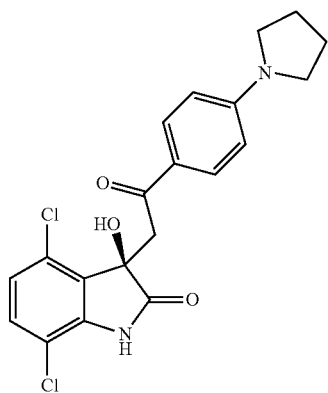
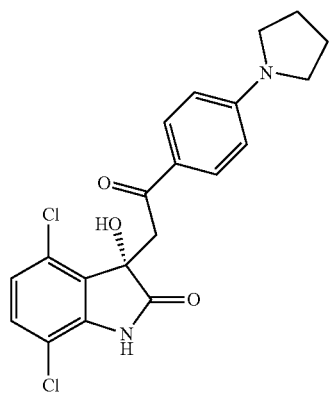
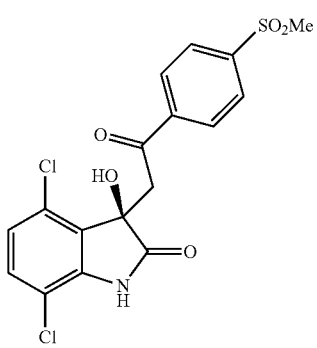
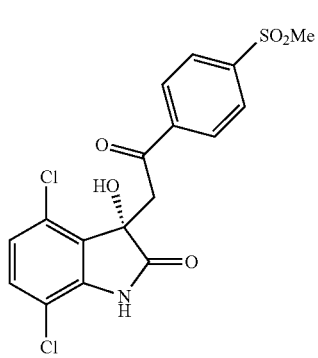
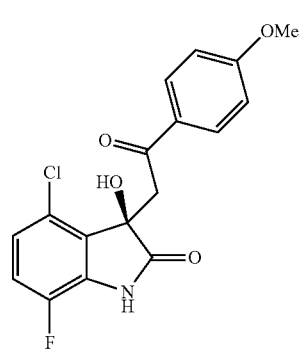
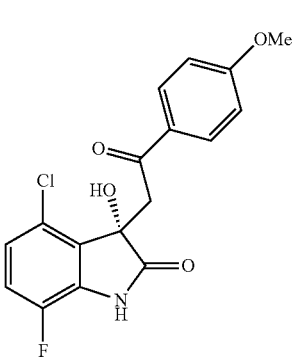
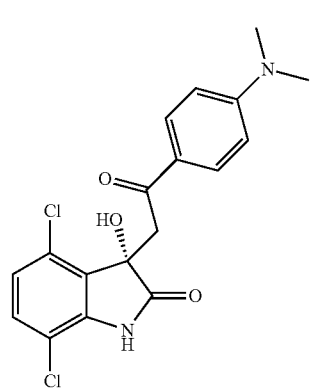
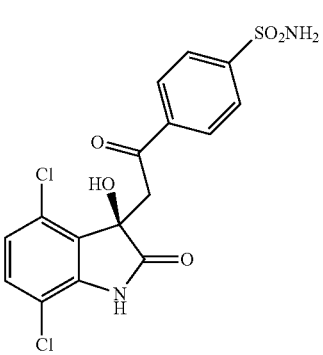

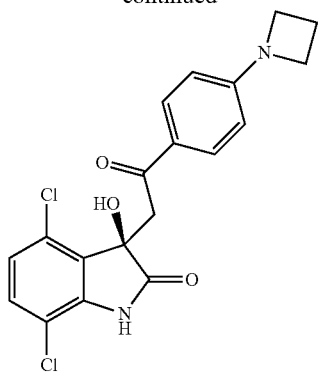
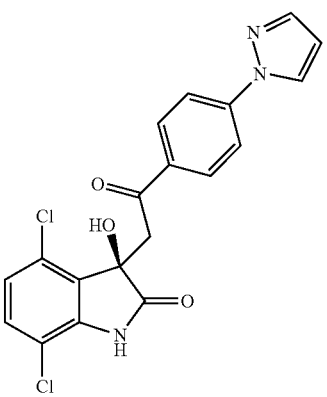
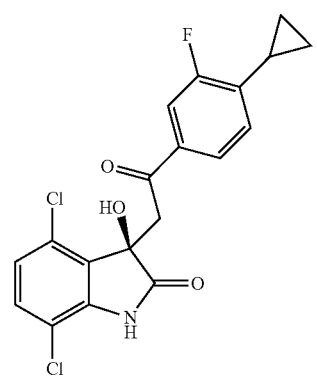
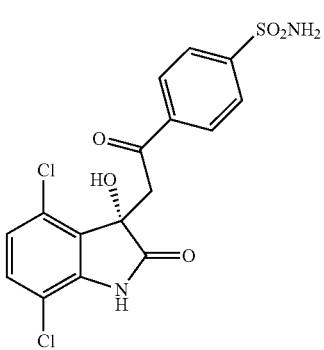
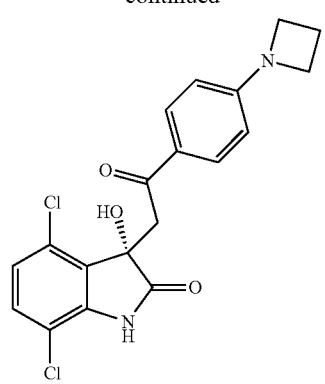
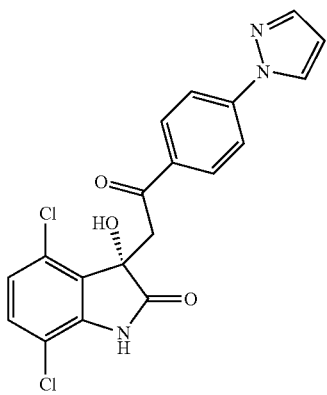
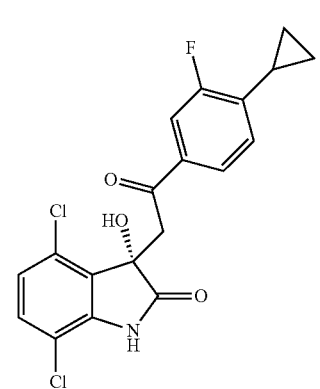
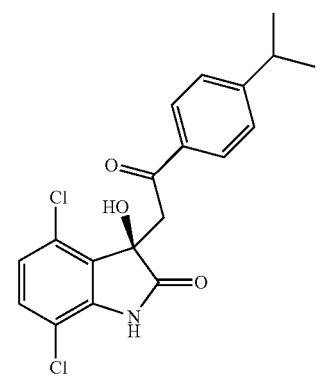

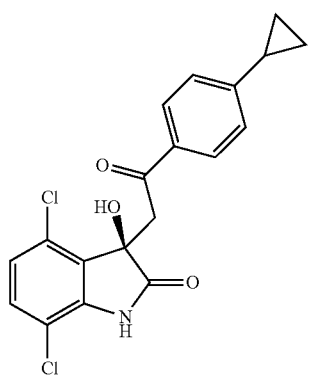
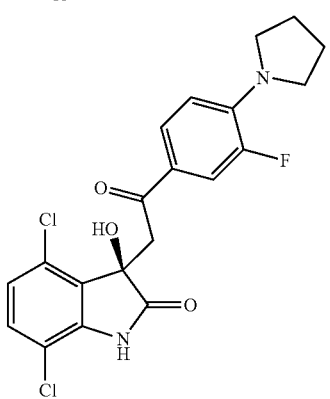
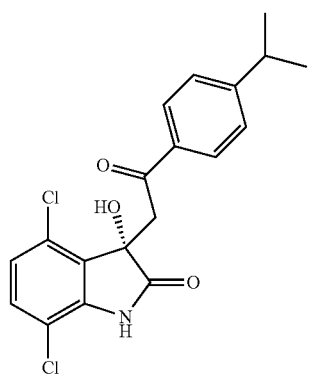
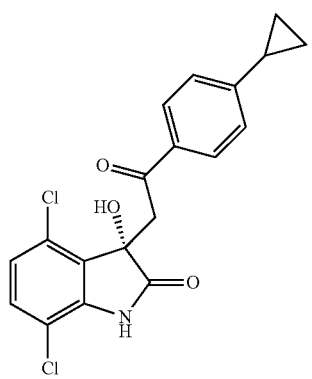
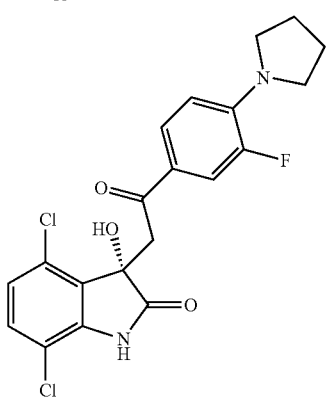
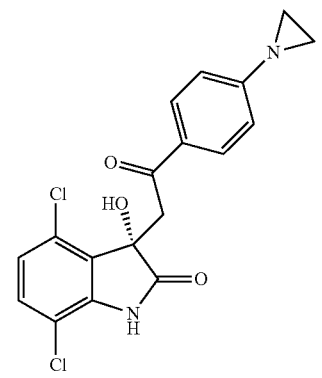
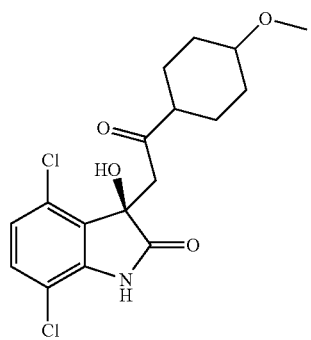

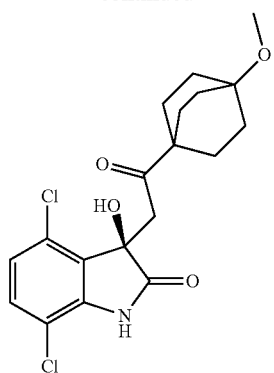
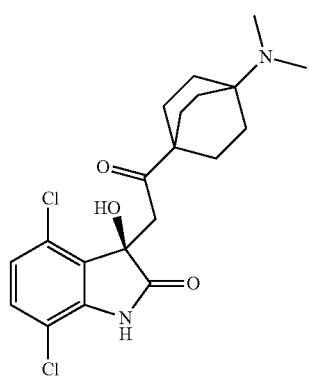
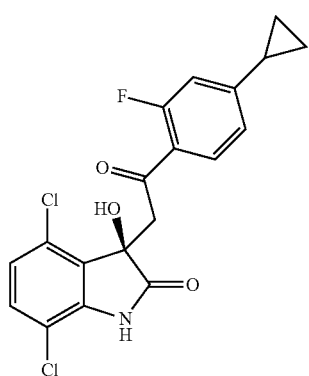
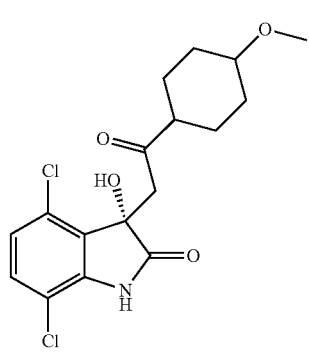
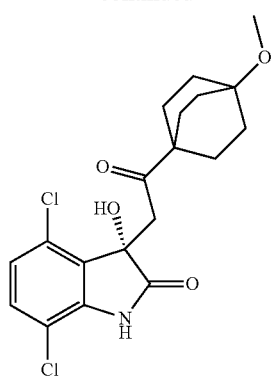
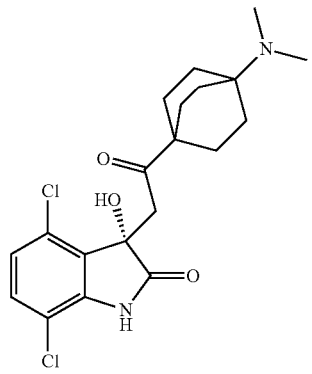
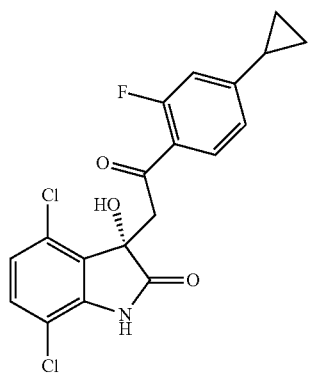
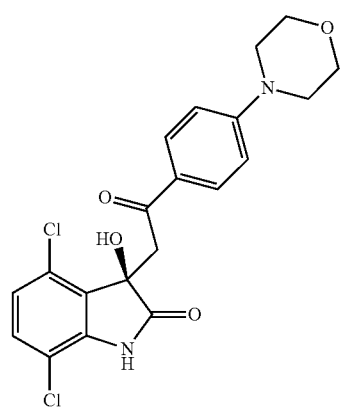

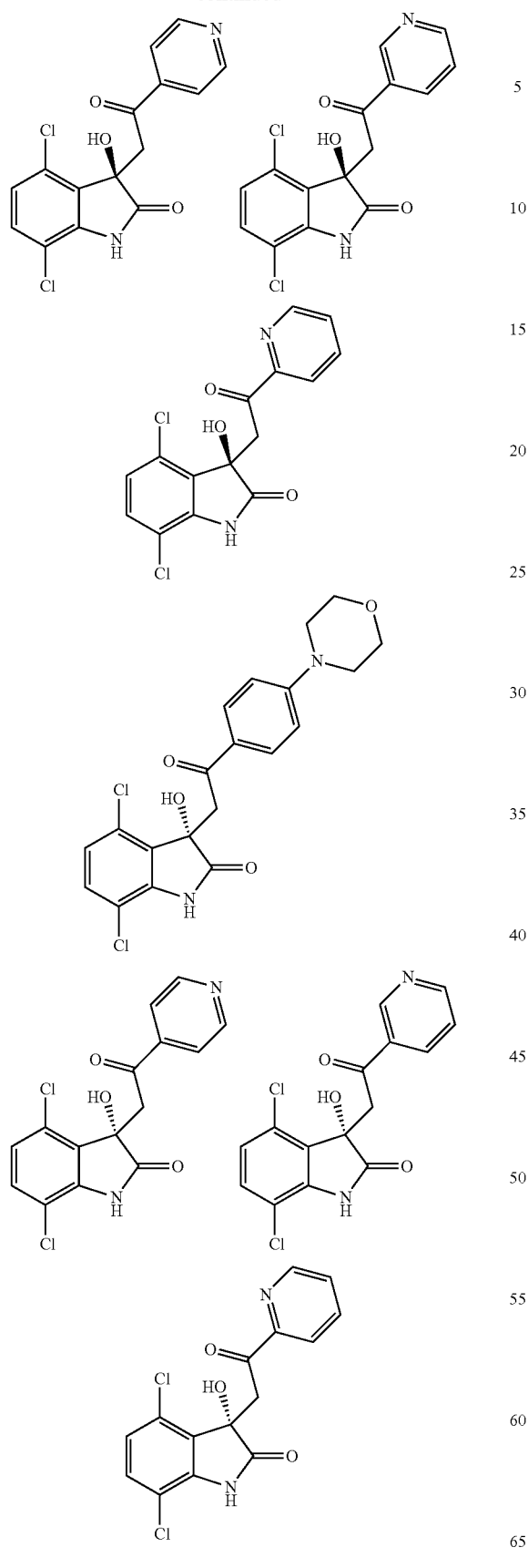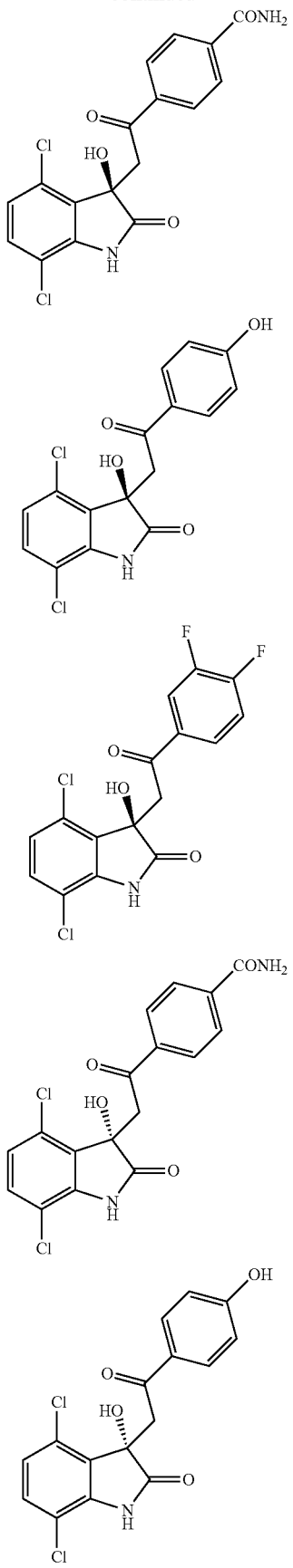

-continued

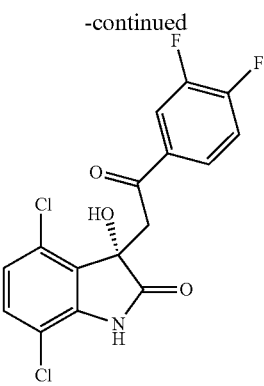

The compounds can be in amorphous form, or in crystalline forms. The crystalline forms of the compounds of preferred embodiments can exist as polymorphs, which are included in preferred embodiments. In addition, some of the compounds of preferred embodiments may also form solvates with water or other organic solvents. Such solvates are similarly included within the scope of the preferred embodiments.

Certain Pharmaceutical Compositions

It is generally preferred to administer the inhibitors of preferred embodiments in an intravenous or subcutaneous unit dosage form; however, other routes of administration are also contemplated. Contemplated routes of administration include but are not limited to oral, parenteral, intravenous, and subcutaneous. The inhibitors of preferred embodiments can be formulated into liquid preparations for, e.g., oral administration. Suitable forms include suspensions, syrups, elixirs, and the like. Particularly preferred unit dosage forms for oral administration include tablets and capsules. Unit dosage forms configured for administration once a day are particularly preferred; however, in certain embodiments it can be desirable to configure the unit dosage form for administration twice a day, or more.

The pharmaceutical compositions of preferred embodiments are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the pharmaceutical compositions can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents.

A pharmaceutically acceptable preservative can be employed to increase the shelf life of the pharmaceutical compositions. Benzyl alcohol can be suitable, although a variety of preservatives including, for example, parabens, thimerosal, chlorobutanol, or benzalkonium chloride can also be employed. A suitable concentration of the preservative is typically from about 0.02% to about 2% based on the total weight of the composition, although larger or smaller amounts can be desirable depending upon the agent selected. Reducing agents, as described above, can be advantageously used to maintain good shelf life of the formulation.

The inhibitors of preferred embodiments can be in admixture with a suitable carrier, diluent, or excipient such as sterile water, physiological saline, glucose, or the like, and can contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; $18^{th}$ and $19^{th}$ editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

For oral administration, the pharmaceutical compositions can be provided as a tablet, aqueous or oil suspension, dispersible powder or granule, emulsion, hard or soft capsule, syrup or elixir. Compositions intended for oral use can be prepared according to any method known in the art for the manufacture of pharmaceutical compositions and can include one or more of the following agents: sweeteners, flavoring agents, coloring agents and preservatives. Aqueous suspensions can contain the active ingredient in admixture with excipients suitable for the manufacture of aqueous suspensions.

Formulations for oral use can also be provided as hard gelatin capsules, wherein the active ingredient(s) are mixed with an inert solid diluent, such as calcium carbonate, calcium phosphate, or kaolin, or as soft gelatin capsules. In soft capsules, the inhibitors can be dissolved or suspended in suitable liquids, such as water or an oil medium, such as peanut oil, olive oil, fatty oils, liquid paraffin, or liquid polyethylene glycols. Stabilizers and microspheres formulated for oral administration can also be used. Capsules can include push-fit capsules made of gelatin, as well as soft, sealed capsules made of gelatin and a plasticizer, such as glycerol or sorbitol. The push-fit capsules can contain the active ingredient in admixture with fillers such as lactose, binders such as starches, and/or lubricants such as talc or magnesium stearate and, optionally, stabilizers.

Tablets can be uncoated or coated by known methods to delay disintegration and absorption in the gastrointestinal tract and thereby provide a sustained action over a longer period of time. For example, a time delay material such as glyceryl monostearate can be used. When administered in solid form, such as tablet form, the solid form typically comprises from about 0.001 wt. % or less to about 50 wt. % or more of active ingredient(s), preferably from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Tablets can contain the active ingredients in admixture with non-toxic pharmaceutically acceptable excipients including inert materials. For example, a tablet can be prepared by compression or molding, optionally, with one or more additional ingredients. Compressed tablets can be prepared by compressing in a suitable machine the active ingredients in a free-flowing form such as powder or granules, optionally mixed with a binder, lubricant, inert diluent, surface active or dispersing agent. Molded tablets can be made by molding, in a suitable machine, a mixture of the powdered inhibitor moistened with an inert liquid diluent.

Preferably, each tablet or capsule contains from about 1 mg or less to about 1,000 mg or more of an inhibitor of the preferred embodiments, more preferably from about 10, 20, 30, 40, 50, 60, 70, 80, 90, or 100 mg to about 150, 200, 250, 300, 350, 400, 450, 500, 550, 600, 650, 700, 750, 800, or 900 mg. Most preferably, tablets or capsules are provided in a range of dosages to permit divided dosages to be administered. A dosage appropriate to the patient and the number of doses to be administered daily can thus be conveniently selected. In certain embodiments it can be preferred to incorporate two or more of the therapeutic agents to be administered into a single tablet or other dosage form (e.g., in a combination therapy); however, in other embodiments it can be preferred to provide the therapeutic agents in separate dosage forms.

Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents can be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, karaya or tragacanth, or alginic acid or salts thereof.

Binders can be used to form a hard tablet. Binders include materials from natural products such as acacia, tragacanth, starch and gelatin, methyl cellulose, ethyl cellulose, carboxymethyl cellulose, polyvinyl pyrrolidone, hydroxypropylmethyl cellulose, and the like.

Lubricants, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, can be included in tablet formulations.

Surfactants can also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

Controlled release formulations can be employed wherein the amifostine or analog(s) thereof is incorporated into an inert matrix that permits release by either diffusion or leaching mechanisms. Slowly degenerating matrices can also be incorporated into the formulation. Other delivery systems can include timed release, delayed release, or sustained release delivery systems.

Coatings can be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments can be added for identification or to characterize different combinations of inhibitor doses When administered orally in liquid form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

Pulmonary delivery can also be employed. The compound is delivered to the lungs while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of compound. Typically, each formulation is specific to the type of device employed and can involve the use of an appropriate propellant material, in addition to diluents, adjuvants, and/or carriers useful in therapy.

The compound and/or other optional active ingredients are advantageously prepared for pulmonary delivery in particulate form with an average particle size of from 0.1 μm or less to 10 μm or more, more preferably from about 0.2, 0.3, 0.4, 0.5, 0.6, 0.7, 0.8, or 0.9 μm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 μm. Pharmaceutically acceptable carriers for pulmonary delivery of inhibitor include carbohydrates such as trehalose, mannitol, xylitol, sucrose, lactose, and sorbitol. Other ingredients for use in formulations can include DPPC, DOPE, DSPC, and DOPC. Natural or synthetic surfactants can be used, including polyethylene glycol and dextrans, such as cyclodextran. Bile salts and other related enhancers, as well as cellulose and cellulose derivatives, and amino acids can also be used. Liposomes, microcapsules, microspheres, inclusion complexes, and other types of carriers can also be employed.

Pharmaceutical formulations suitable for use with a nebulizer, either jet or ultrasonic, typically comprise the inhibitor dissolved or suspended in water at a concentration of about 0.01 or less to 100 mg or more of inhibitor per mL of solution, preferably from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg per mL of solution. The formulation can also include a buffer and a simple sugar (e.g., for protein stabilization and regulation of osmotic pressure). The nebulizer formulation can also contain a surfactant, to reduce or prevent surface induced aggregation of the inhibitor caused by atomization of the solution in forming the aerosol.

Formulations for use with a metered-dose inhaler device generally comprise a finely divided powder containing the active ingredients suspended in a propellant with the aid of a surfactant. The propellant can include conventional propellants, such as chlorofluorocarbons, hydrochlorofluorocarbons, hydrofluorocarbons, and hydrocarbons. Preferred propellants include trichlorofluoromethane, dichlorodifluoromethane, dichlorotetrafluoroethanol, 1,1,1, 2-tetrafluoroethane, and combinations thereof. Suitable surfactants include sorbitan trioleate, soya lecithin, and oleic acid.

Formulations for dispensing from a powder inhaler device typically comprise a finely divided dry powder containing inhibitor, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, preferably from about 5, 10, 15, 20, 25, 30, 35, 40, 45, or 50 wt. % to about 55, 60, 65, 70, 75, 80, 85, or 90 wt. % of the formulation.

When a compound of the preferred embodiments is administered by intravenous, parenteral, or other injection, it is preferably in the form of a pyrogen-free, parenterally acceptable aqueous solution or oleaginous suspension. Suspensions can be formulated according to methods well known in the art using suitable dispersing or wetting agents and suspending agents. The preparation of acceptable aqueous solutions with suitable pH, isotonicity, stability, and the like, is within the skill in the art. A preferred pharmaceutical composition for injection preferably contains an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils can be employed conventionally as a solvent or suspending medium. For this purpose, any bland fixed oil can be employed including synthetic mono or diglycerides. In addition, fatty acids such as oleic acid can likewise be used in the formation of injectable preparations. The pharmaceutical compositions can also contain stabilizers, preservatives, buffers, antioxidants, or other additives known to those of skill in the art.

The duration of the injection can be adjusted depending upon various factors, and can comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

The compounds of the preferred embodiments can additionally employ adjunct components conventionally found in pharmaceutical compositions in their art-established fashion and at their art-established levels. Thus, for example, the compositions can contain additional compatible pharmaceutically active materials for combination therapy (such as supplementary antimicrobials, antipruritics, astringents, local anesthetics, anti-inflammatory agents, reducing agents, chemotherapeutics and the like), or can contain materials useful in physically formulating various dosage forms of the preferred embodiments, such as excipients, dyes, thickening agents, stabilizers, preservatives or antioxidants. Anti-cancer agents that can be used in combination with the compounds of preferred embodiments include, but are not limited to, vinca alkaloids such as vinblastine and vincristine; anthracyclines such as doxorubicin, daunorubicin, epirubicin; anthracenes such as bisantrene and mitoxantrone; epipodophyllo-toxins such as etoposide and teniposide; and other anticancer drugs such as actinomyocin D, mithomycin C, mitramycin, methotrexate, docetaxel, etoposide (VP-16), paclitaxel, docetaxel, and adriamycin); and immunosuppressants (e.g., cyclosporine A, tacrolimus). In some embodiments, the compounds, compositions and methods provided herein may be in combination with histone deacetylase inhibitors (HDAC), aurora kinase inhibitors, demethylating agents (such as 5-AZA cytidine), immunotherapy with natural killer cells, IGF-IR antibodies, Ewing antigen antibodies, immunosuppressive drugs, and hydroxyurea. Examples of histone deacetylase inhibitors include vorinostat, romidepsin, panobinostat, valproic acid, belinostat, mocetinostat, givinostat, and trichostatin A. Examples of aurora kinase inhibitors include ZM447439, hesperadin, and VX-680. Examples of demethylating agents include 5-azacytidine, 5-azadeoxycytidine, and procaine. Examples of immunosuppressive drugs include 6-mercaptopurine, and azathioprine.

Certain Kits

The compounds of the preferred embodiments can be provided to an administering physician or other health care professional in the form of a kit. The kit is a package which houses a container which contains the compounds in a suitable pharmaceutical composition, and instructions for administering the pharmaceutical composition to a subject. The kit can optionally also contain one or more additional therapeutic agents, e.g., chemotherapeutics currently employed for treating the sarcomas described herein. For example, a kit containing one or more compositions comprising compounds of the preferred embodiments in combination with one or more additional chemotherapeutic agents can be provided, or separate pharmaceutical compositions containing an inhibitor of the preferred embodiments and additional therapeutic agents can be provided. The kit can also contain separate doses of a compound of the preferred embodiments for serial or sequential administration. The kit can optionally contain one or more diagnostic tools and instructions for use. The kit can contain suitable delivery devices, e.g., syringes, and the like, along with instructions for administering the inhibitor(s) and any other therapeutic agent. The kit can optionally contain instructions for storage, reconstitution (if applicable), and administration of any or all therapeutic agents included. The kits can include a plurality of containers reflecting the number of administrations to be given to a subject.

EXAMPLES

The ETS family of transcription factors is critical for development, differentiation, proliferation, and plays an important role in apoptosis and tissue remodeling. Transcriptional consequences of ETS protein deregulation by overexpression, gene fusion, and modulation by RAS/MAPK and PI3K signaling are linked to alterations in normal cell functions, and lead to increased proliferation, sustained angiogenesis, invasion, and metastasis. Overexpressed ETS proteins and ETS family fusion proteins have been reported in acute myeloid leukemia (AML) and diffuse large B cell lymphoma (DLBCL). In DLBCL, the 11q24.3 region has been identified as a recurrent lesion and a contributor to the pathogenesis of disease, leading to the deregulation of ETS family members, ETS 1 and FLI1. Additionally, in AML, the overexpression and translocations of ERG, an ETS family member, has been shown to be associated with poor prognosis in complex or normal karyotypes.

TK216 is a first in class, small molecule that directly binds EWS-FLI1 inhibiting the biological activity of ETS-family transcription factor oncoproteins and is currently under clinical investigation in patients with Ewing sarcoma. The EWS1-FLI1 is a fusion protein that has been shown to be the driver of Ewing Sarcoma (ES). In preclinical potency models, TK216 blocked the binding between EWS-FLI1 and RNA helicase A, showed a significant transcriptional decrease in COS7 cells transfected with a EWS-FLI1 responsive promoter ($EC_{50}$<100 nM), and inhibited the proliferation of A4573 cells (EWS-FLI1 expressing Ewing sarcoma cell line) at nanomolar concentrations ($EC_{50}$<200 nM).

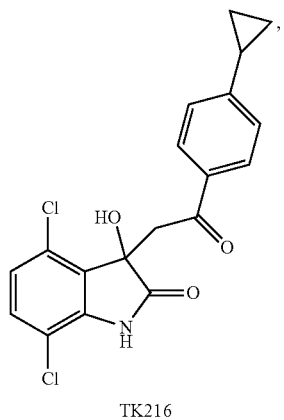 [SMILES: O=C(CC1(O)C(=O)Nc2c(Cl)ccc(Cl)c21)c1ccc(C2CC2)cc1 ; "TK216"]

TK216

4,7-Dichloro-3-(2-(4-cyclopropylphenyl)-2-oxo-ethyl)-3-hydroxyindolin-2-one

TK216 also had anti-proliferative effects, causes cell cycle arrest, and induces apoptosis in a panel of AML and DLBCL cell lines with deregulated ETS family members. Upregulation of FLI1 and/or ERG ETS family members was observed in the myeloid cell lines evaluated (HL-60, Kasumi-1, ML-2, MOLM-13, MOLM-16, and THP-1). Treatment with TK216 showed a decrease in cellular viability and induced dose-dependent apoptosis of cells at 48 hours. Similarly, in a panel of DLBCL cell lines (TMD-8, HBL-1, U2932, DOHH2, WSU-DLCL2, OCI-Ly18, and OCI-Ly19), TK216 treatment resulted in a decrease in cellular proliferation and an increase in apoptosis. In vivo efficacy studies in xenograft models of DLBCL indicated anti-tumor activity consistent with in vitro findings, confirming the utility and efficacy of TK216 in the treatment of AML and DLBCL by targeting the aberrant expression and translocations in the ETS-family of transcription factors, which contribute to the pathogenesis of the disease.

The mechanism of action of TK216 is illustrated in FIG. 1. As illustrated in FIG. 1, TK216 is active in oncogenesis (anchorage-independent growth; tumors in mice), altered gene expression (↑ E2G2 (chromatin regulator; ↑ VEGF-A (angiogenesis)), and alternative splicing (cyclin D1b (activates cell cycle); ARID 1A-ex 18L (chromatin regulator). TK216 inhibited aptosis (programmed cell death; inhibits tumor growth), altered gene expression (↓ E2G2; ↓ VEGF-A), and variant isoforms (cyclin D1a (slows cell cycle); ARID 1A-ex 185 (non-oncogenic)).

TK216 treatment inhibited EWS-FLI1 protein interactions, leading to a decrease in transcription and proliferation.

Figure 2:
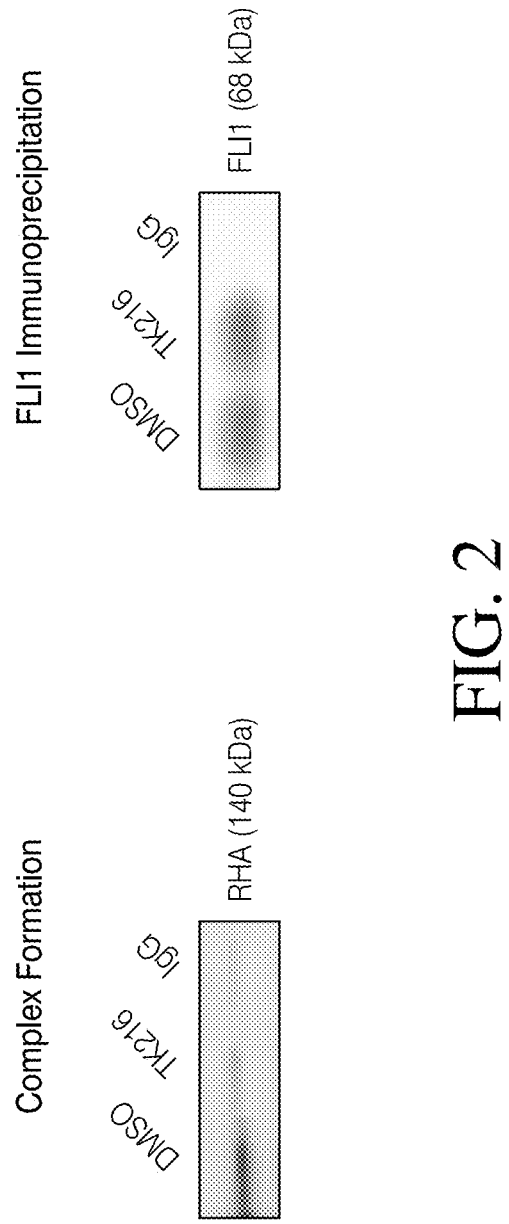
FIG. 2 shows TK216 treatment inhibited EWS-FLI1 protein interactions, leading to a decrease in transcription and proliferation.

FLI1 was immunoprecipitated following treatment with TK216 or DMSO control in A4573 (see FIG. 2).

Figure 3:
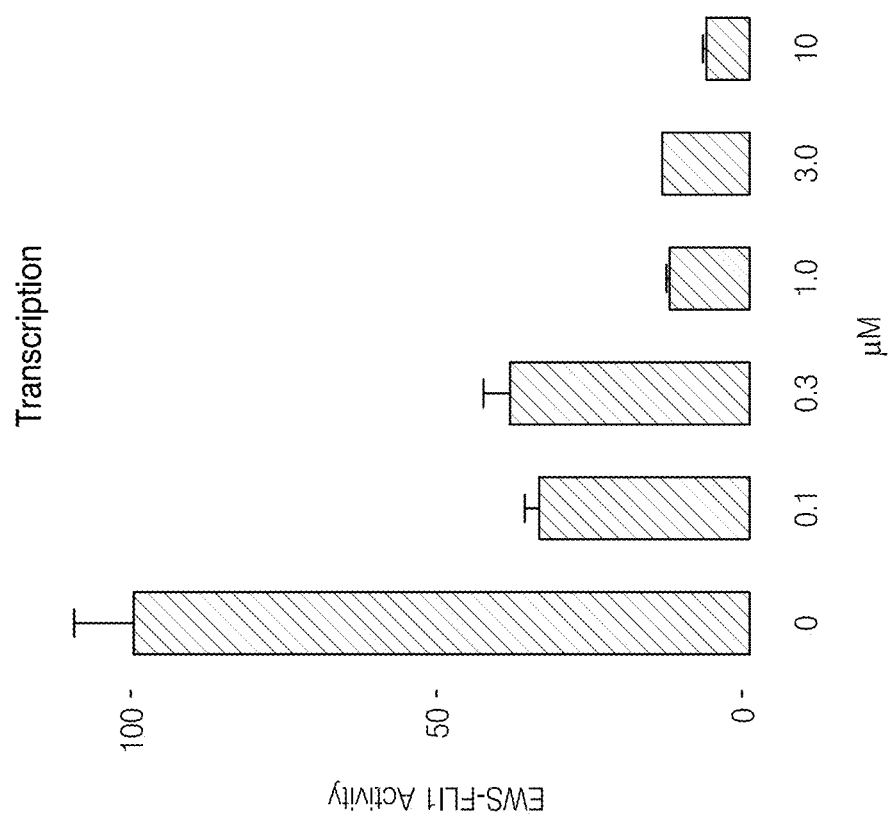
FIG. 3 shows TK216 reduced transcriptional activity in COS7 cells co-transfected with EWS-FLI1 and NROB1 reporter-luciferase plasmids which contain EWS-FLI1 DNA-binding sites.

TK216 reduced transcriptional activity in COS7 cells co-transfected with EWS-FLI1 and NROB1 reporter-luciferase plasmids which contain EWS-FLI1 DNA-binding sites, as shown in FIG. 3.

Figure 4:
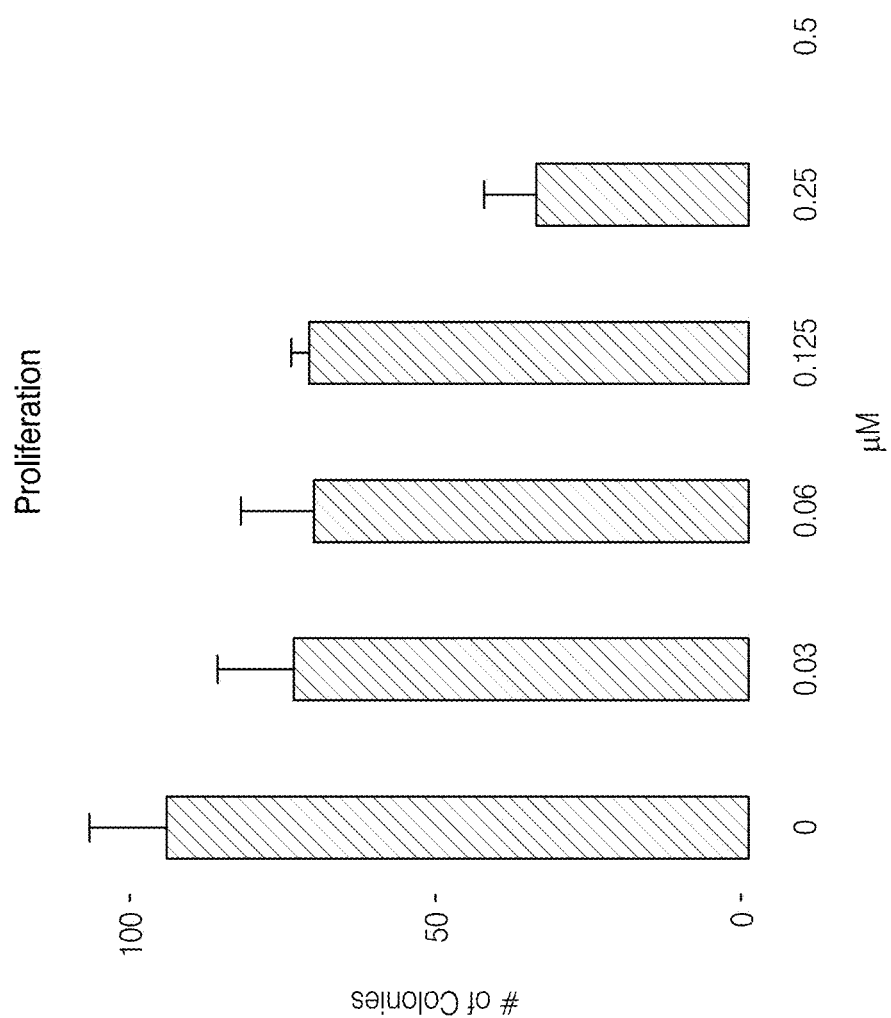
FIG. 4 shows treatment with TK216 resulted in a dose-dependent inhibition of proliferation in Ewing Sarcoma A4573 cell line.

Treatment with TK216 resulted in a dose-dependent inhibition of proliferation in Ewing Sarcoma A4573 cell line, as shown in FIG. 4.

Figure 5:
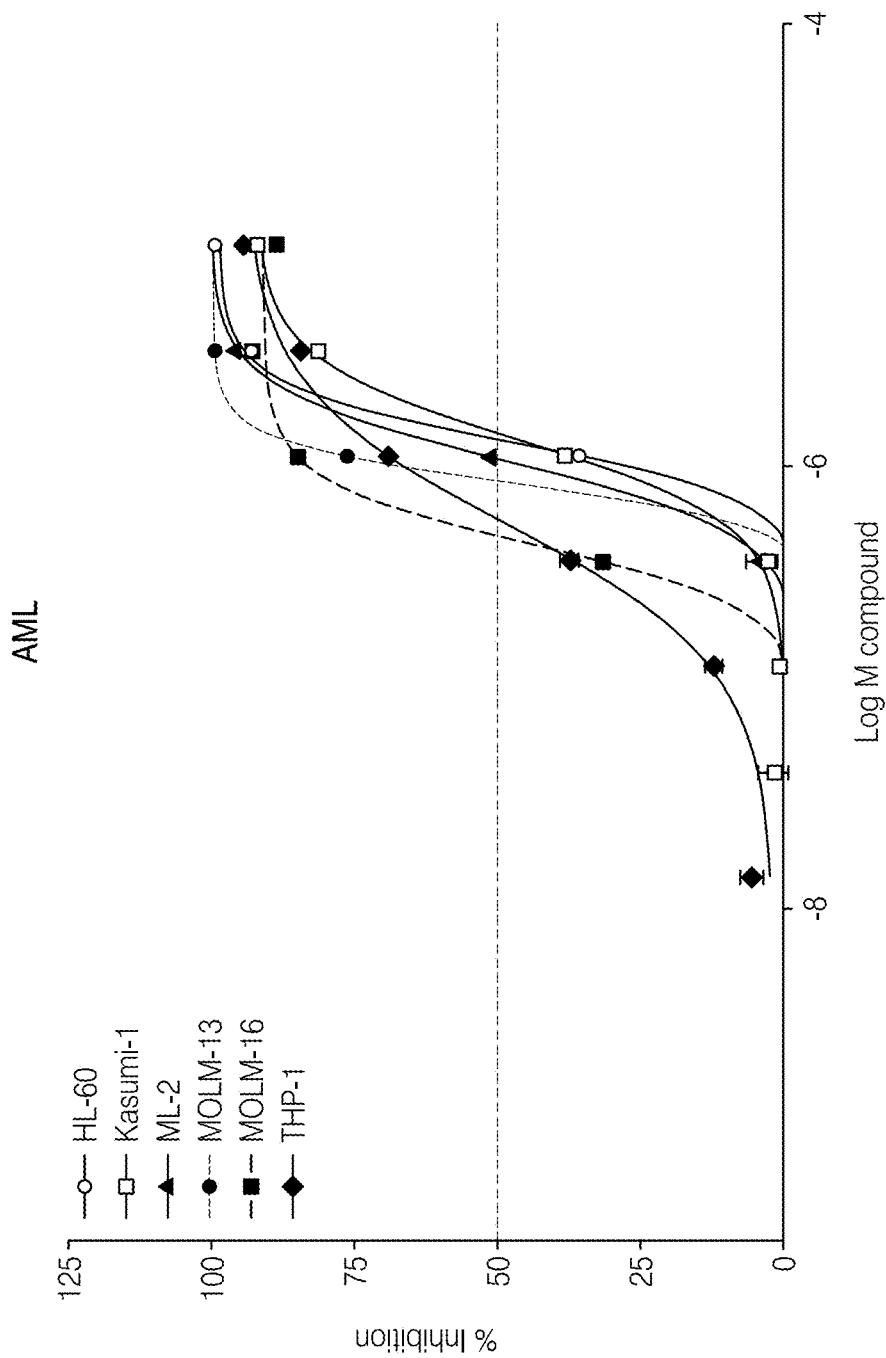
FIG. 5 shows TK216 displayed anti-proliferative activity in AML cell lines.

TK216 displayed anti-proliferative activity in AML cell lines. The IC50 of TK216 for each cell line was determined in a 72 hr CellTiter-Glo assay, as shown in FIG. 5 and TABLE 1.

TABLE 1

TK216 $IC_{50}$ in AML Cell Lines

| Cell line | TK216-2 $IC_{50}$ (µM) | Cisplatin $IC_{50}$ (µM) |
|---|---|---|
| HL-60 | 0.363 | 1.931 |
| Kasumi-1 | 0.393 | 4.560 |
| ML-2 | 0.291 | 1.395 |
| MOLM-13 | 0.228 | 0.798 |
| MOLM-16 | 0.129 | 2.190 |
| THP-1 | 0.152 | 1.359 |

Figure 6:
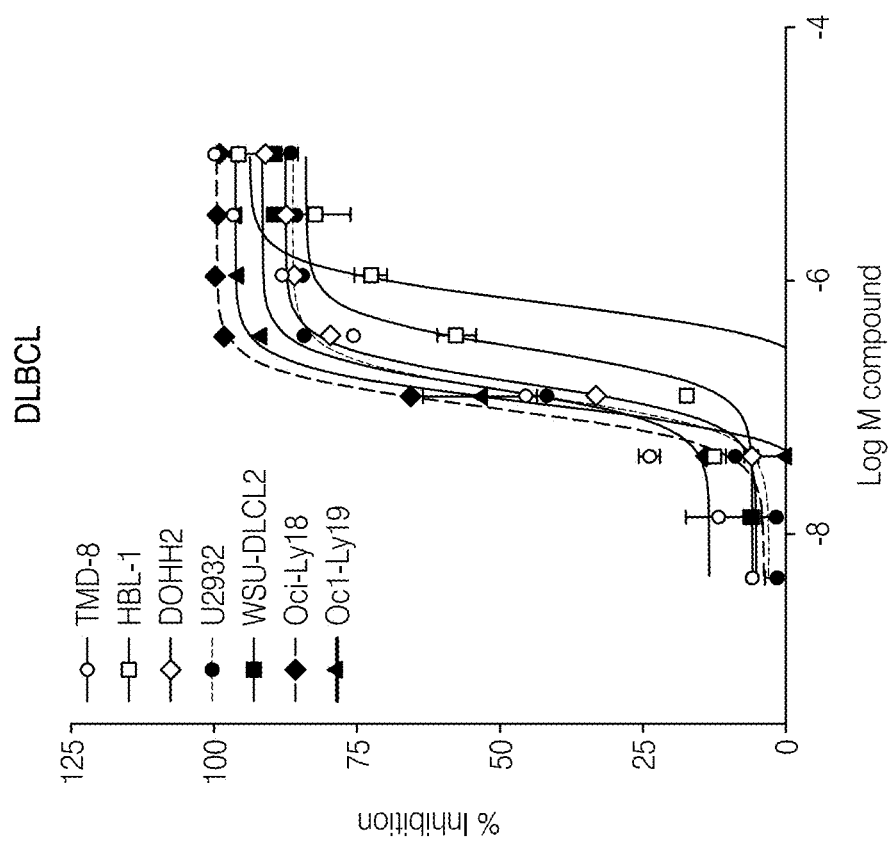
FIG. 6 shows TK216 displayed anti-proliferative activity in DLBCL cell lines.

TK216 displayed anti-proliferative activity in DLBCL cell lines. The $IC_{50}$ of TK216 for each cell line was determined in a 72 hr CellTiter-Glo assay, as shown in FIG. 6 and TABLE 2.

TABLE 2

TK216 $IC_{50}$ in DLBCL Cell Lines

| Cell line | TK216 $IC_{50}$ (µM) |
|---|---|
| TMD-8 | 0.152 |
| HBL-1 | 0.304 |
| DOHH2 | 0.160 |
| U2932 | 0.127 |
| WSU-DLCL2 | 0.897 |
| OCI-Ly18 | 0.095 |
| OCI-Ly19 | 0.106 |

Figure 7:
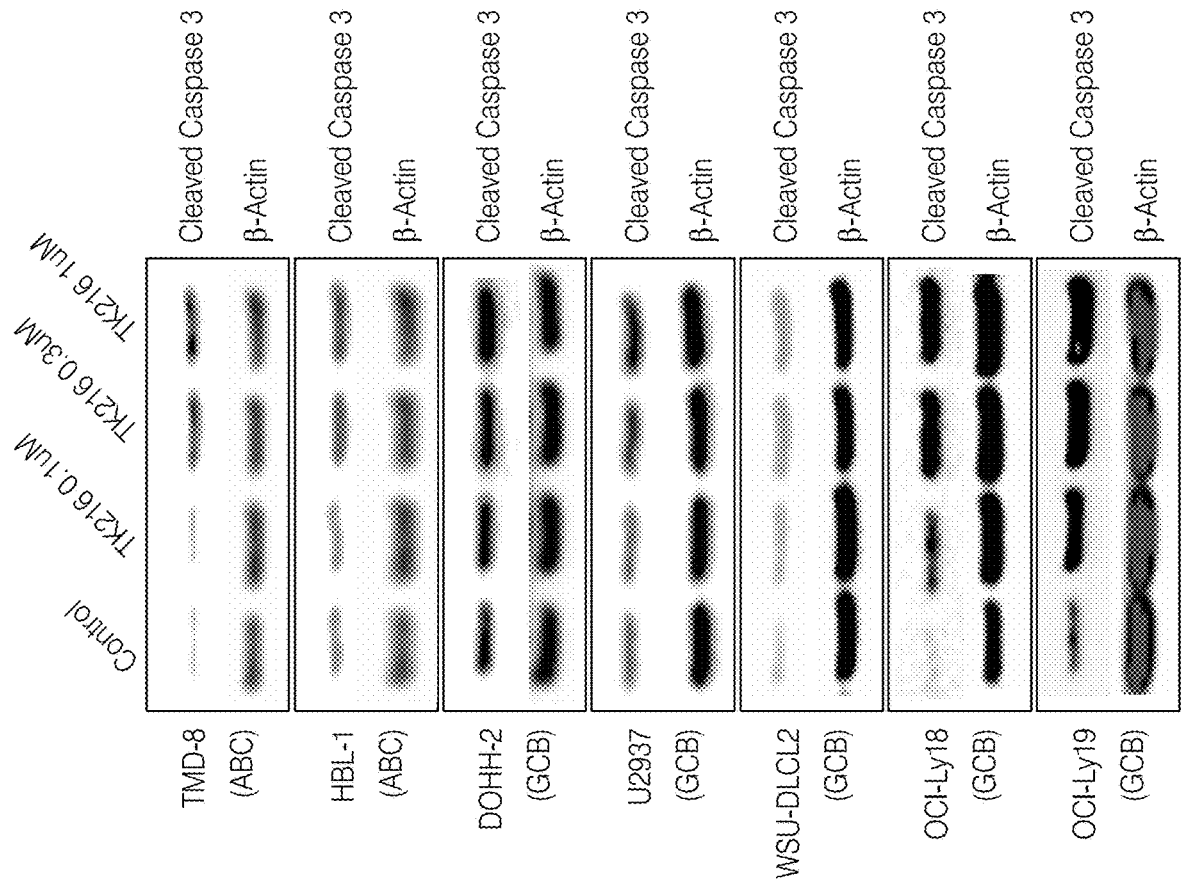
FIG. 7 and FIG. 8 show TK216 induced apoptosis in DLBCL cell lines, with the amount of cleaved-Caspase 3 normalized to b-actin and presented as fold over control.
Figure 8:
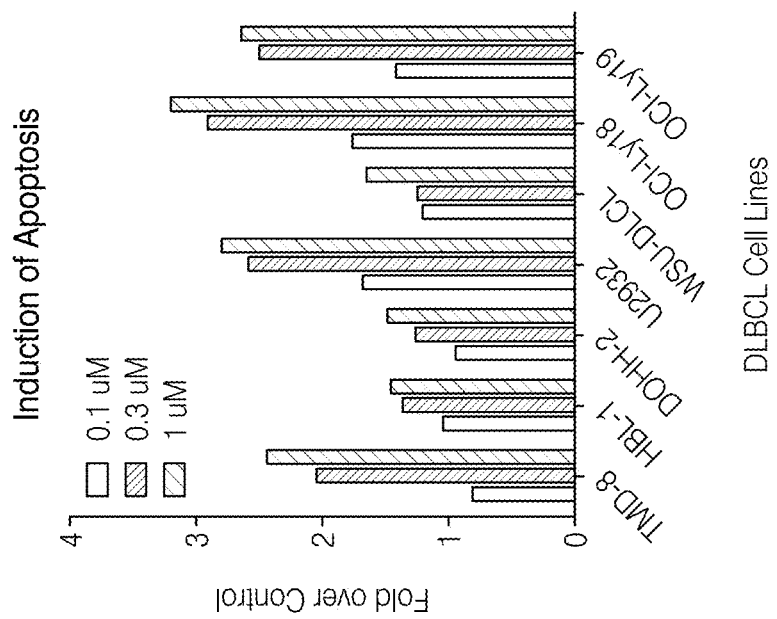

TK216 induced apoptosis in DLBCL cell lines. Cells were treated with various concentrations of TK216 for 18 h and apoptosis was assessed by detection of cleaved-Caspase 3. The amount of cleaved-Caspase 3 was normalized to b-actin and presented as fold over control, as shown in FIG. 7 and FIG. 8.

Figure 9:
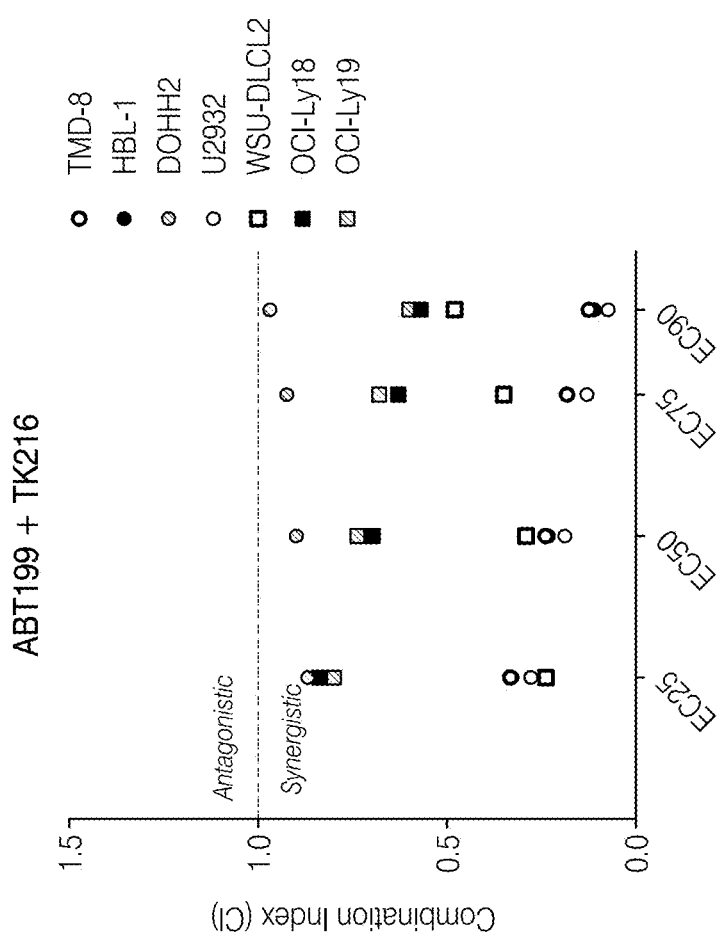
FIG. 9 shows TK216 displayed synergy when combined with BCL-2 (ABT199) inhibitors, wherein CalcuSyn software was used to determine the Combination Index (CI) using the Chou/Talalay equation.
Figure 10:
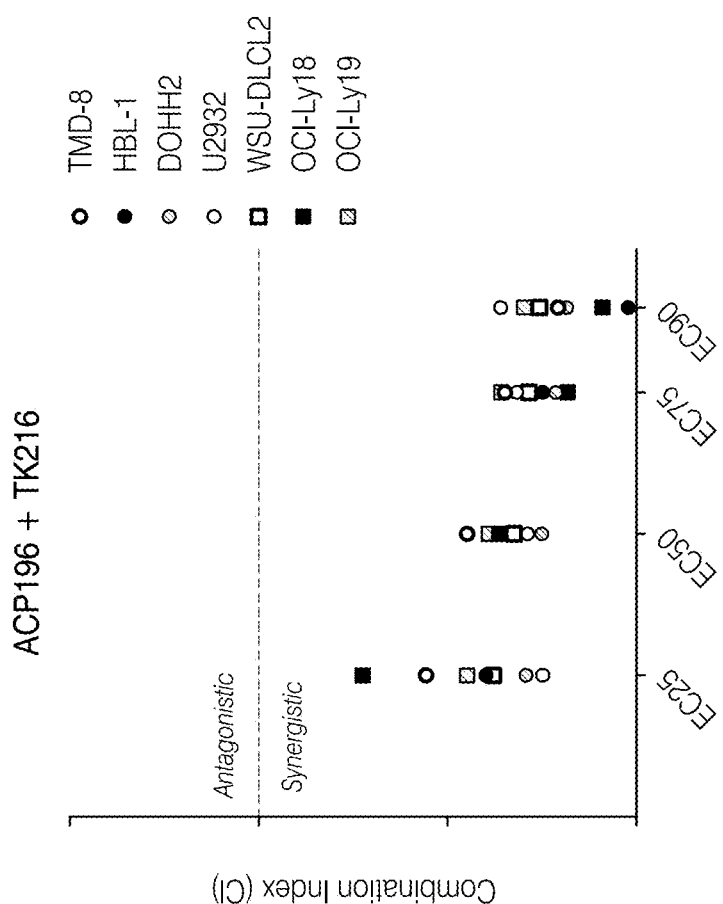
FIG. 10 show TK216 displayed synergy when combined with BTK (ACP196) inhibitors, wherein CalcuSyn software was used to determine the Combination Index (CI) using the Chou/Talalay equation.

TK216 displayed synergy when combined with BCL-2 (ABT199) and BTK (ACP196) inhibitors. The median-effect analysis was used to determine synergism, antagonism, or additivity of TK216 when combined with ABT199 (BCL-2i) and ACP196 (BTKi). CalcuSyn software was used to determine the Combination Index (CI) using the Chou/Talalay equation, as shown in FIG. 9 and FIG. 10.

Figure 11:
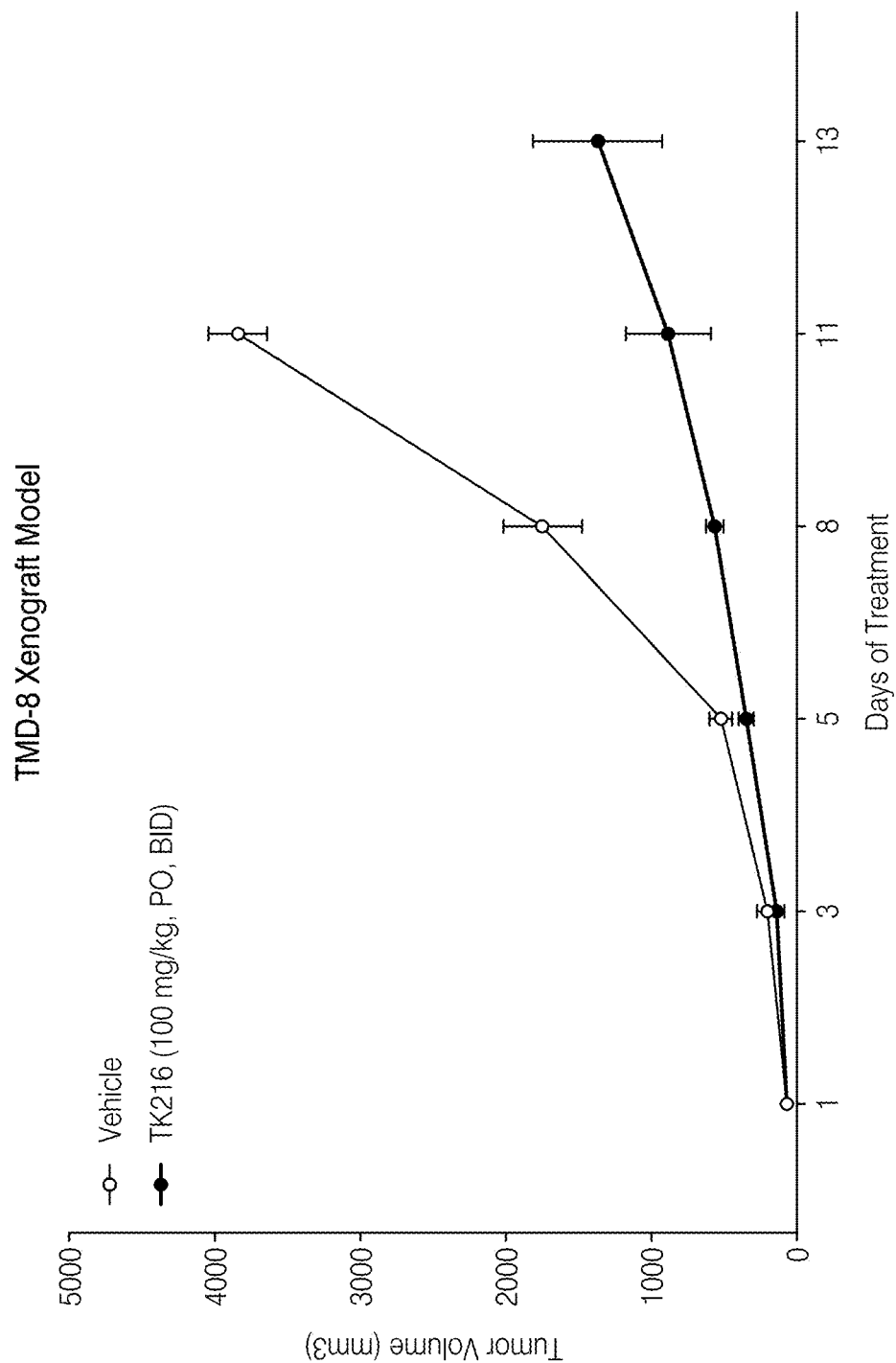
FIG. 11 shows TK216 displayed anti-tumor activity in a TMD8 xenograft model.

TK216 displayed anti-tumor activity in a DLBCL xenograft model. The anti-tumor activity of TK216 was assessed in nude mice harboring TMD-8 tumors, a DLBCL-ABC xenograft model. TK216 was administered orally as a solution at 100 mg/kg BID for 13 days. Results are shown in FIG. 11.

Figure 12:
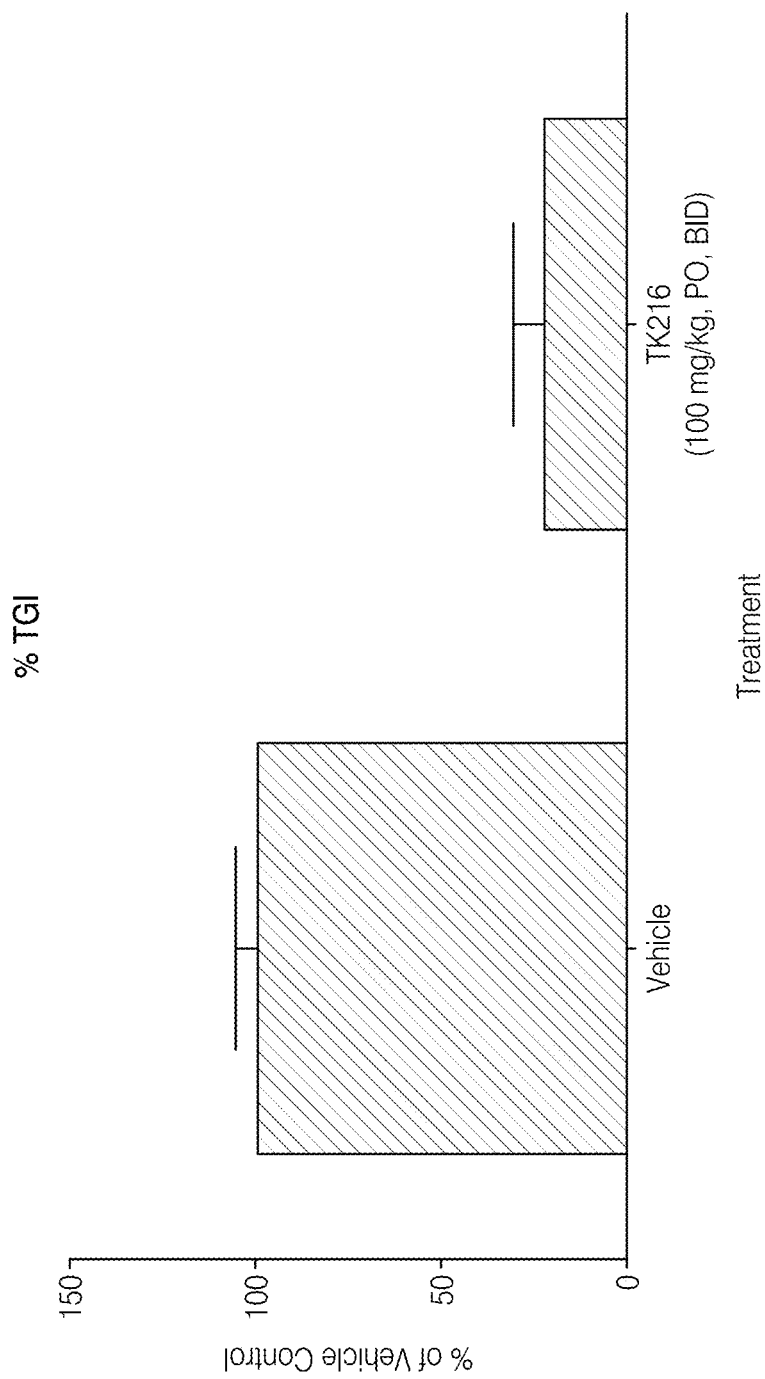
FIG. 12 shows treatment with TK216 results in tumor growth inhibition of the TMD-8 xenograft model when compared to vehicle control following 13 days of treatment.

Treatment with TK216 resulted in tumor growth inhibition. TK216 resulted in 77% tumor growth inhibition of the TMD-8 xenograft model when compared to vehicle control following 13 days of treatment, as shown in FIG. 12.

As the above data demonstrated, TK216 is a first in class, small molecule that directly binds EWS-FLI1 inhibiting the biological activity of ETS-family transcription factor. In AML and DLBCL cell lines with deregulated ETS-family members, treatment with TK216 resulted in potent inhibition of proliferation and the induction of apoptosis. Combination of TK216 with BCL-2 and BTK inhibitors in DLBCL cell lines lead to synergistic activity and allowed for a more effective inhibition of cell proliferation. Daily, oral administration of TK216 potently inhibited tumor growth in xenograft models of DLBCL with deregulated expression of ETS-family members, and is well-tolerated. The inhibition of the EWS-FLI1 oncogene offers a promising approach for the treatment of Ewing Sarcoma, e.g., relapsed/refractory Ewing Sarcoma.

Venetoclax (4-(4-{[2-(4-Chlorophenyl)-4,4-dimethyl-1-cyclohexen-1-yl]methyl}-1-piperazinyl)-N-({3-nitro-4-[(tetrahydro-2H-pyran-4-ylmethyl)amino]phenyl}sulfonyl)-2-1H-pyrrolo[2,3-b]pyridin-5-yloxy)benzamide) is used for the treatment of chronic lymphocytic leukemia, e.g., in patients who have relapsed or have been refractory to previous treatment and who have the 17p deletion genetic mutation.

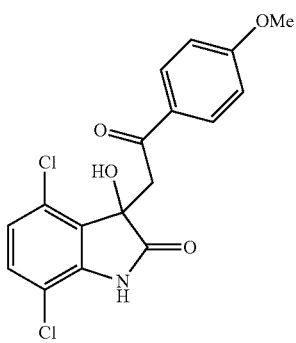

YK-4-279

4,7-dichloro-3-hydroxy-3-(2-(4-methoxyphenyl)-2-oxoethyl)indolin-2-one

TK-216 is a YK-4-279 clinical derivative that is in phase 1 for patients with relapsed or refractory Ewing sarcoma. Preclinical testing has been conducted for TK-216 in lymphoma models.

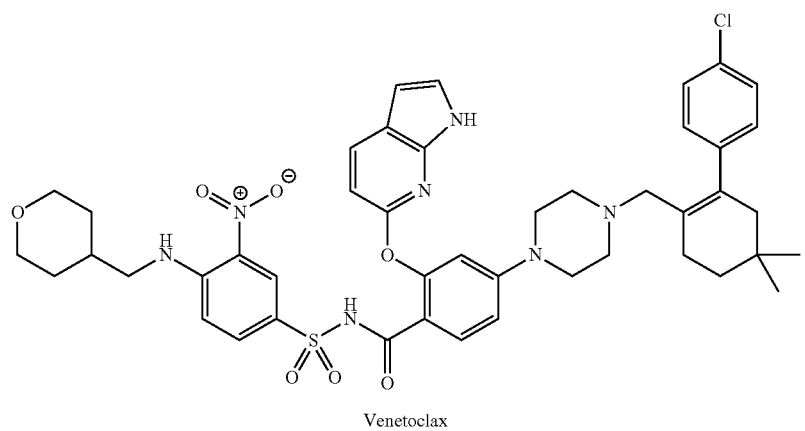 [SMILES: CC1(C)CCC(CN2CCN(c3ccc(C(=O)NS(=O)(=O)c4ccc(NCC5CCOCC5)c([N+](=O)[O-])c4)c(Oc4ccc5cc[nH]c5n4)c3)CC2)=C(c2ccc(Cl)cc2)C1]

Venetoclax

Figure 13:
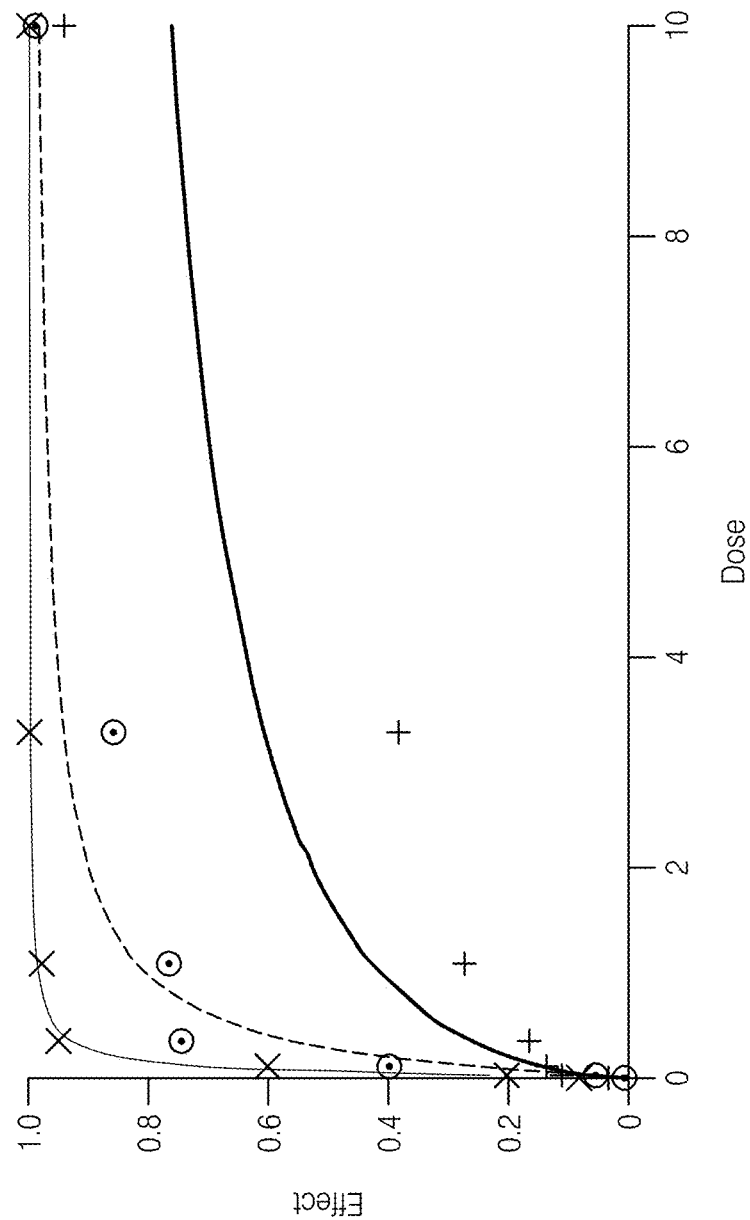
FIG. 13 is a dose-effect curve for TK216 in combination with venetoclax in the TMD8 cell line, wherein the top curve (x) was for the combination therapy, the middle curve (⊙) was for TK216, and the bottom curve (+) was for venetoclax.
Figure 14:
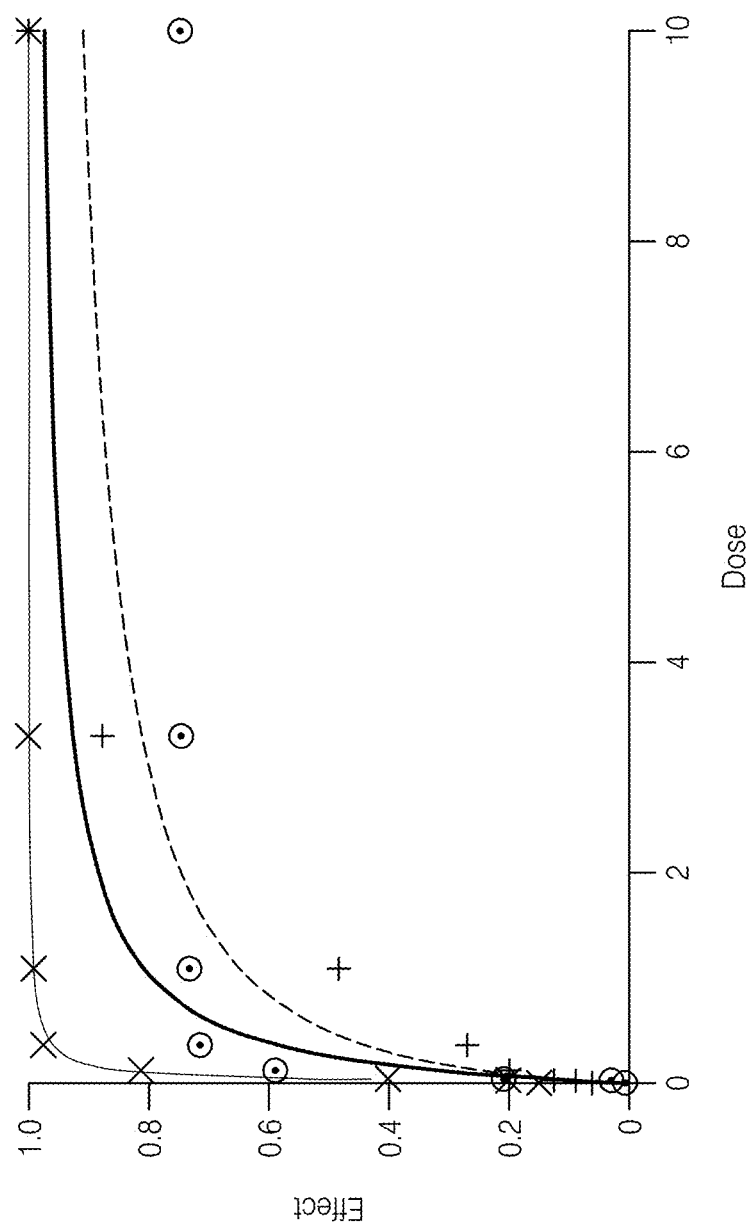
FIG. 14 is a dose-effect curve for TK216 in combination with venetoclax in the U2932 cell line, wherein the top curve (x) was for the combination therapy, the middle curve (⊙) was for TK216, and the bottom curve (+) was for venetoclax.
Figure 15:
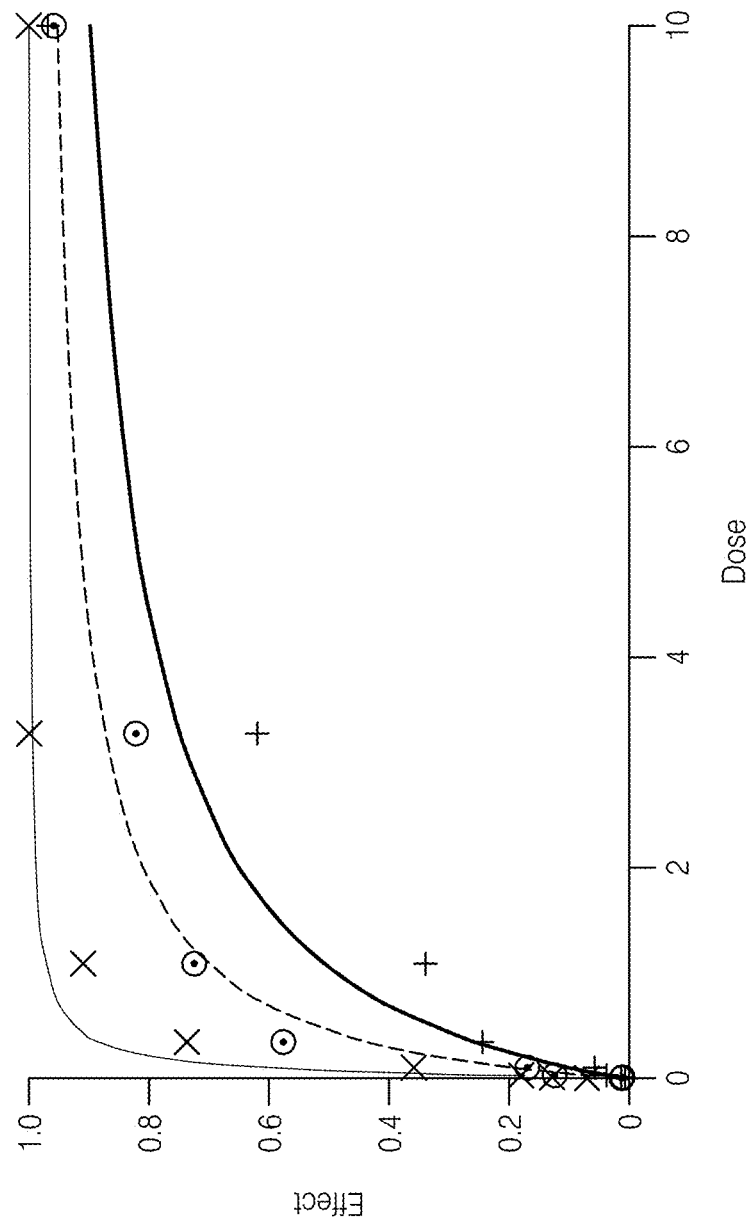
FIG. 15 is a dose-effect curve for TK216 in combination with venetoclax in the HLB1 cell line, wherein the top curve (x) was for the combination therapy, the middle curve (⊙) was for TK216, and the bottom curve (+) was for venetoclax.

TK216 was tested in combination with venetoclax and has been demonstrated to exhibit synergism in dose-effect in DLBCL cell lines. In each of FIGS. 13-15, the top curve (×) was for the combination therapy, the middle curve (○) was for TK216, and the bottom curve (+) was for venetoclax. FIG. 13 is a dose-effect curve for TK216 in combination with venetoclax in the TMD8 cell line. FIG. 14 is a dose-effect curve for TK216 in combination with venetoclax in the U2932 cell line. FIG. 15 is a dose-effect curve for TK216 in combination with venetoclax in the HLB1 cell line.

Figure 16:
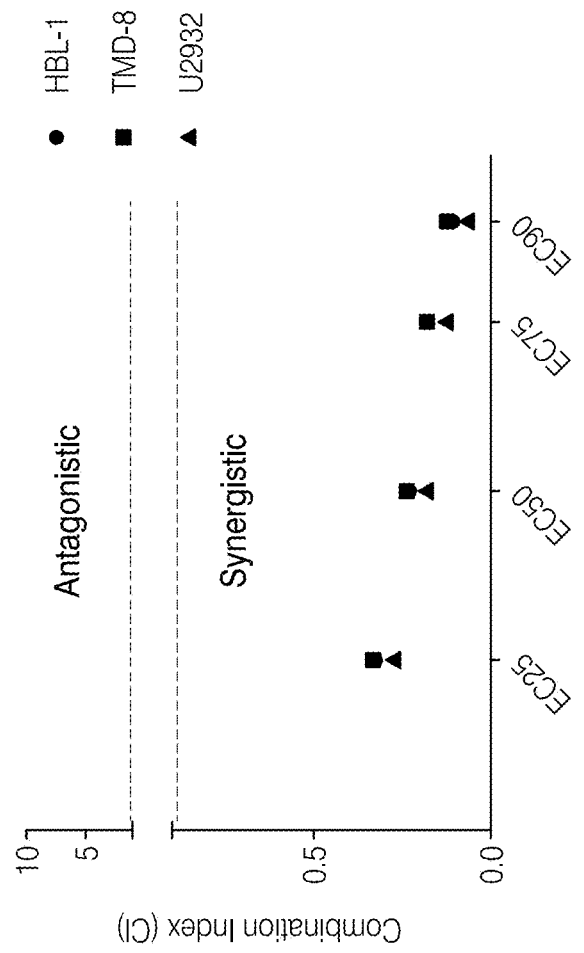
FIG. 16 shows the results of dose-effect testing conducted in DLBLC cell lines (TMD8, HBL1, U2932), indicating a synergistic effect across doses.
Figure 17:
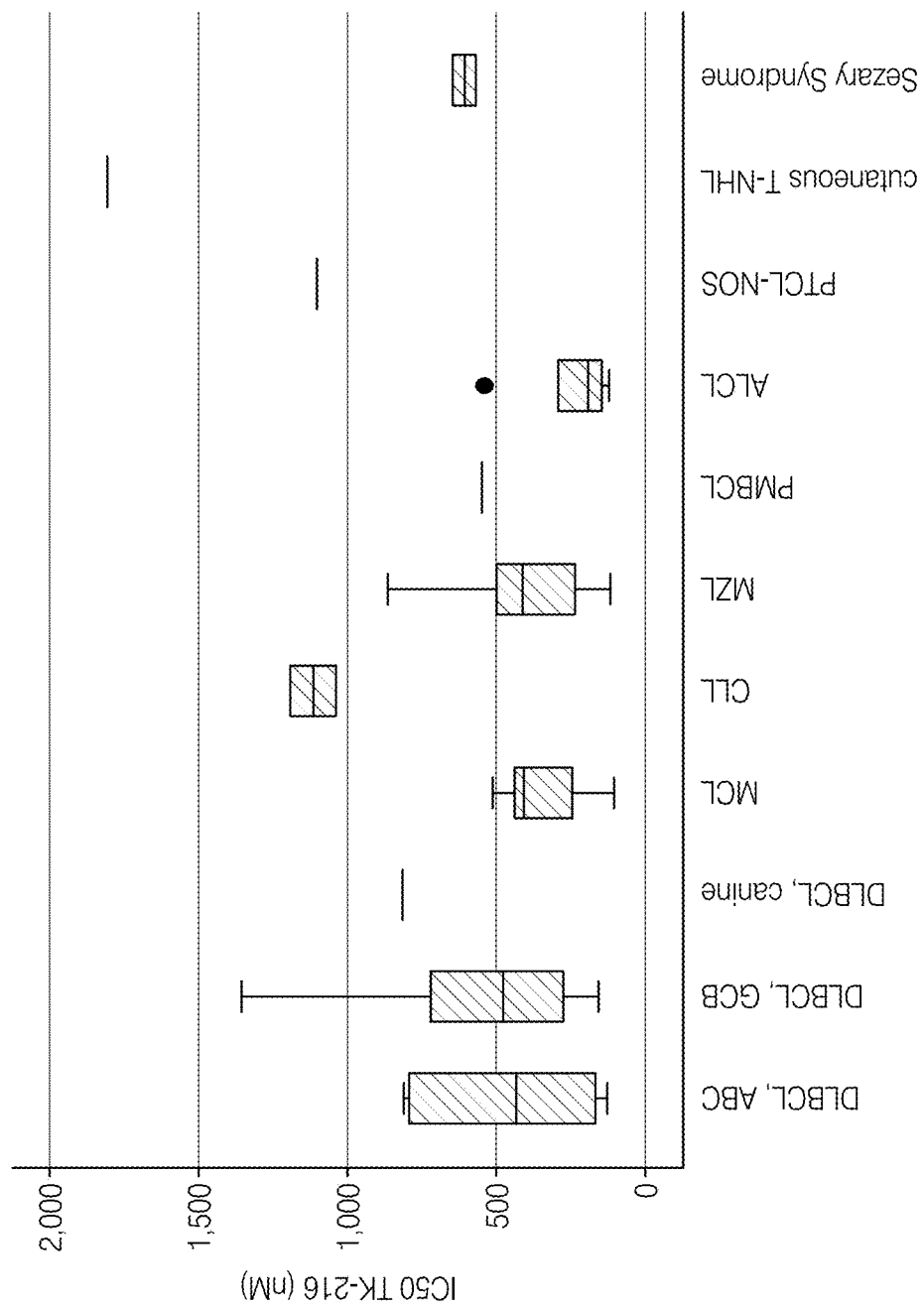
FIG. 17 shows the distribution of IC50 values for TK-216 in lymphoma cell lines by individual histologies. Y-axis: IC50 values. In each box-plot, the line in the middle of the box represents the median and the box extends from the 25th to the 75th percentile (interquartile range, IQ); the whiskers extend to the upper and lower adjacent values (i.e., ±1.5 IQ).
Figure 18A:
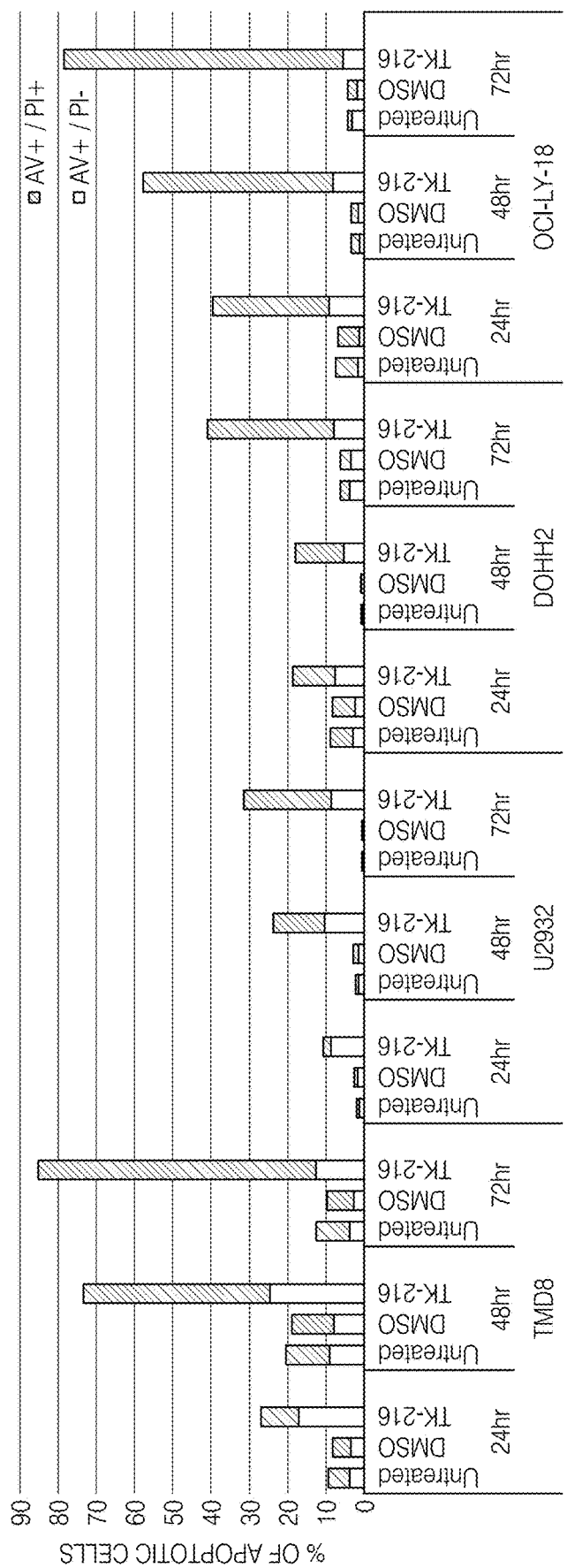
FIGS. 18A and 18B show apoptosis and cell cycle distribution of TK-216 in DLBCL cell lines.
Figure 18B:
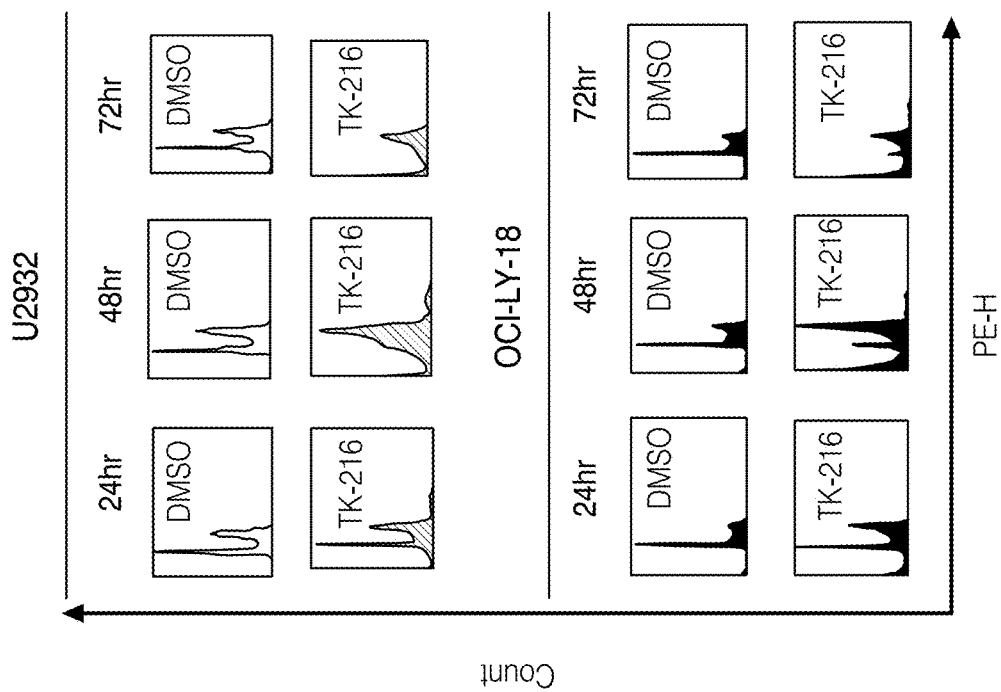
Figure 19:
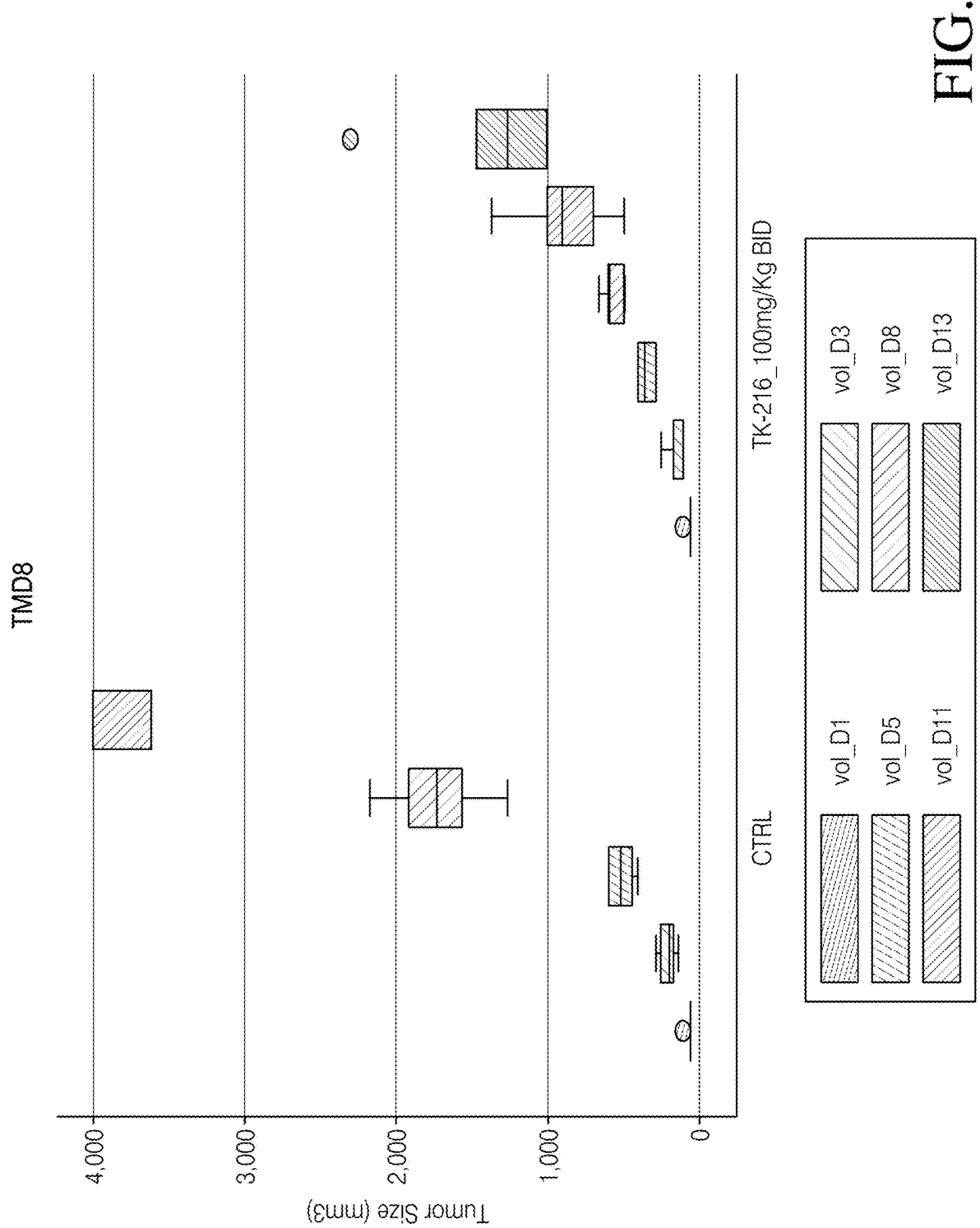
FIG. 19 shows the effects of TK-216 in a xenograft model of ABC-DLBCL. NOD-Scid mice subcutaneously inoculated with TMD8 cells ($15 \times 10^6$) were split in two groups respectively treated with TK-216 (100 mg/kg, BID, po, n=9) and control vehicle (n=10). In each box-plot, the line in the middle of the box represents the median and the box extends from the 25th to the 75th percentile (interquartile range, IQ); the whiskers extend to the upper and lower adjacent values (i.e., ±1.5 IQ).
Figure 20:
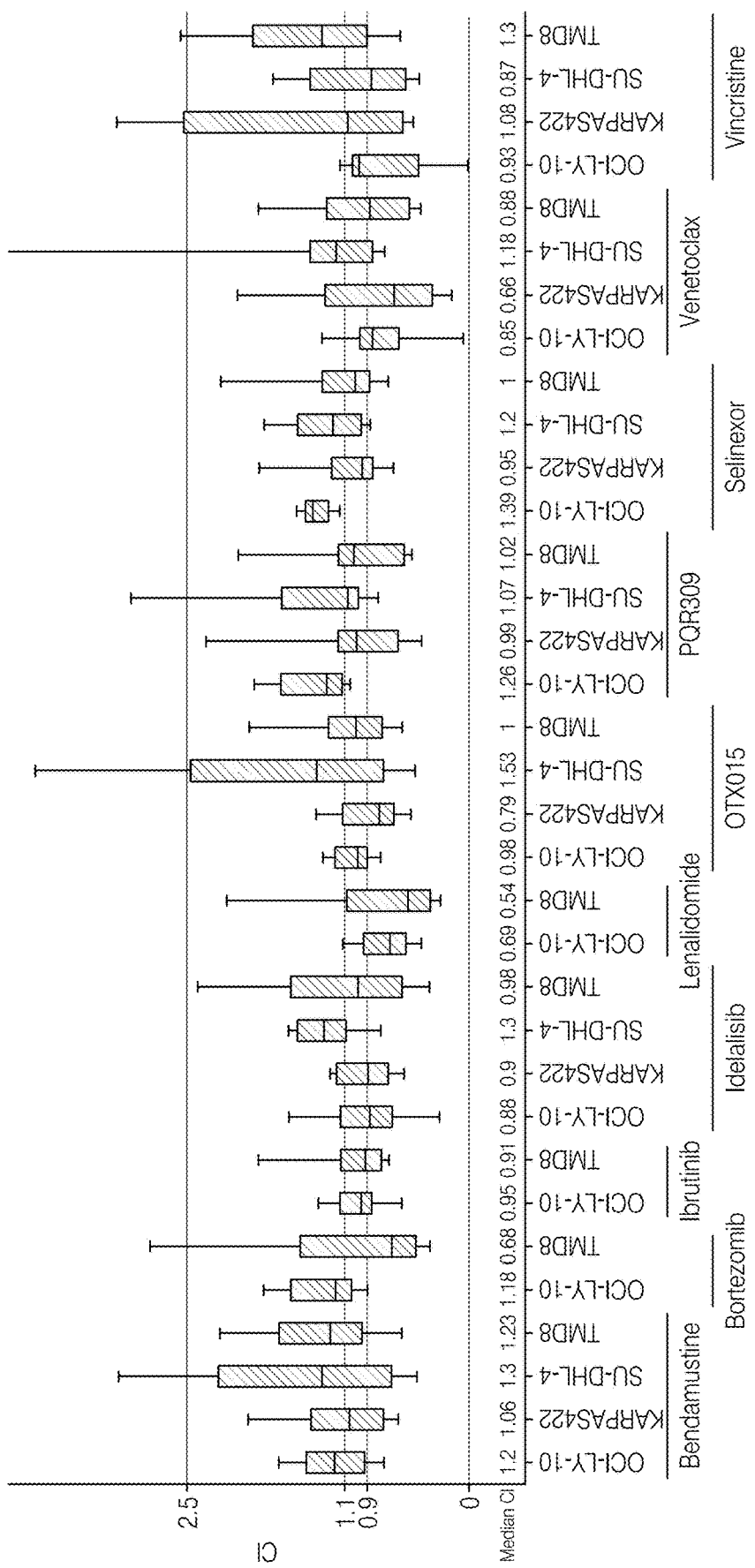
FIG. 20 shows TK216 combinations in DLBCL cell lines: box-plots of the CI values obtained in individual cell lines. Y-axis: CI values. In each box-plot, the line in the middle of the box represents the median and the box extends from the 25th to the 75th percentile (interquartile range, IQ); the whiskers extend to the upper and lower adjacent values (i.e., ±1.5 IQ); outside values have been omitted from the figure. CIs for TK-216/rituximab in TMD8, TK-216/rituximab in Karpas422, TK-216/rituximab in OCI-LY-10 are not plotted due to CI values >3. Combinations tested included bendamustine, bortezomib, ibrutinib, idelalisib, lenalidomide, OTX015 (birabresib, CAS No. 202590-98-5), PQR309 (bimiralisib, CAS No. 1225037-39-7 (free base)), selinexor, venetoclax, and vincristine. Synergism was observed for TK216 in combination with bortezomib (TMD8), idelalisib (OCI-LY-10, KARPAS422), lenalidomide (OCI-LY-10, TMD8), OTX015 (KARPAS422), venetoclax (OCI-LY-10, KARPAS422, TMD8), and vincristine (SU-DHL-4). An additive effect was observed for TK216 in combination with bendamustine (KARPAS422), ibrutinib (OCI-LY-10, TMD8), lidelalisib (TMD8), OTX015 (OCI-LY-10, TMD8), PQR309 (KARPAS422, SU-DHL-4, TMD8), selinexor (KARPAS422, TMD8), and vincristine (OCI-LY-10, KARPAS422). No benefit effects was observed for TK216 in combination with bendamustine (OCI-LY-10, SU-DHL-4, TMD8), bortezomib (OCI-LY-10), idelalisib (SU-DHL-4), OTX015 (SU-DHL-4), PQR309 (OCI-LY-10), selinexor (OCI-LY-10, SU-DHL-4), venetoclax (SU-DHL-4), and vincristine (TMD8).

Dose-effect testing was conducted in DLBLC cell lines (TMD8, HBL1, U2932) indicating a synergistic effect across doses, as shown in FIG. 16.

ETS transcription factors, such as FLI1 and SPIB, are recurrently deregulated in human lymphomas. The small molecule YK-4-279 (also referred to as YK-279 or YK279, is 4,7-dichloro-3-hydroxy-3-(2-(4-methoxyphenyl)-2-oxoethyl)indolin-2-one) inhibits binding of EWS1-FLI1 fusion protein to RHA with growth arrest and apoptosis in Ewing sarcoma cells, and exhibits in vitro anti-lymphoma activity.

56 lymphoma cell lines [27 diffuse large B cell lymphoma (DLBCL); 10 mantle cell lymphoma; 6 marginal zone lymphoma; 5 anaplastic large T-cell lymphoma; 8 others] were exposed to TK-216 increasing doses for 72 h using a Tecan D300e Digital Dispenser and 384 well plates. Cell proliferation was measured with MTT. In vivo study was done in NOD-SCID mice; treatments were started with approximately sc 60 mm3 tumor volumes. The study demonstrated TK-216 was very active, with a median IC50 of 449 nM (95% C.I.: 367-506), as shown in FIG. 1. Sensitivity was not affected by the lymphoma cell of origin (B vs T; activated B cell type DLBCL versus germinal center type DLBCL) or MYC and TP53 status. There was a non-statistically significant trend for lower sensitivity in cell lines bearing BCL2 chromosomal translocation (P=0.07, DLBCL only; P=0.06, all cell lines). The anti-tumor activity was mainly cytotoxic, as confirmed performing cell cycle analysis and Annexin V staining in 6 DLBCL cell lines (TMD8, U2932, HBL1, OCI-LY-18, WSU-DLCL2, DOHH2; TK-216 or DMSO for 24, 48, 72 h), in which a time-dependent apoptosis was preceded by a G2/M arrest, as shown in FIG. 2.

Antitumor activity was then tested using DLBCL TMD8 cells xenografts, as shown in FIG. 3. Compared with a control group (n=10), mice treated with TK-216 (100 mg/Kg, BID; n=9) clearly presented a reduction in tumor growth, already evident at day 3 and becoming much stronger with time (D3, D5, D8, D11: P<0.01; D13, P not available since control group had to be stopped due to tumor volume) and a four-times reduction in tumor volume at D11 (P<0.01). TK-216 was also tested in combination with other targeted agents in DLBCL cell lines, as shown in FIG. 4. A benefit was observed with the combination of TK-216 with the immunomodulator lenalidomide (synergism in 2/2 activated B cell type DLBCL), with the bromodomain and extra-terminal protein (BET) inhibitor OTX015 (MK-8628) (synergism in 2/4 cells and additive effect in 1/4 cells), with the anti-CD20 monoclonal antibody rituximab (synergism in 2/3 cells) and with the BCL2 inhibitor venetoclax (synergism in 3/4 cells). The latter synergism could be linked to the previously mentioned negative trend between TK-216 IC50 values and the presence of BCL2 translocation.

The test results demonstrated that TK-216 presented strong preclinical anti-lymphoma activity, both as a single agent and in combination with other therapeutic agents.

The two main DLBCL subtypes are the germinal center B cell (GCB) and the ABC types, characterized by individual biologic and clinical features. Since up to 40% DLBCL patients are still not cured with the standard treatments, there is the need for novel therapies. YK-4-279 is a small molecule that inhibits binding of the EWS1-FLI1 fusion protein to RHA, resulting in growth arrest and apoptosis in Ewing sarcoma cells. Its derivative, TK-216, is the first in class inhibitor of the ETS-family of transcription factors in phase I (NCT02657005 for relapsed or refractory Ewing sarcoma). Both compounds have shown promising preclinical anti-lymphoma activity. Data has been obtained on their mechanism of action in DLBCL.

Cell lines were exposed to YK-4-279 or TK-216, alone or in combination with other compounds, for 72 h using a Tecan D300e Digital Dispenser and 96 well plates. Cell proliferation was measured with MTT. Synergy was determined with the Chou-Talalay combination index. Gene expression profiling (GEP) was performed with the Illumina HumanHT 12 Expression BeadChips. In vivo studies were done in NOD-SCID mice and treatments started with 60 mm3 tumor volumes sc.

TK-216 showed strong in vitro and in vivo anti-lymphoma activity. Anti-tumor activity has been demonstrated for YK-4-279 in the same ABC DLBCL model (TMD8 xenograft) as for TK-216. Compared with a control group (n=10), mice treated with YK-4-279 (100 mg/Kg, BID; n=9) clearly presented a reduction in tumor growth at D8 and D11 (P<0.01) and D13 (P not available since the control group had to be stopped due to tumor volume). In accordance with combination data showing a specific synergism of TK-216 when combined with the immunomodulatory drug (IMID) lenalidomide in ABC DLBCL, when YK-4-279 was combined with the BTK-inhibitor ibrutinib, the PI3K-delta inhibitor idelalisib, the BET inhibitor OTX-015 and lenalidomide in four DLBCL cell lines (2 ABC, 2 GCB), the biggest benefit was achieved with the combination of YK-4-279 plus lenalidomide with synergism in both ABC DLBCL. Since lenalidomide is active in mantle cell lymphoma (MCL), the synergism of the combination of TK-216 and lenalidomide was confirmed also in two MCL cell lines.

With the aim to understand the mechanism of action of YK-4-279 and TK-216, the baseline RNA expression levels of the different ETS factors were correlated with sensitivity to the drugs. SPIB was the gene presenting the most significant negative correlation with both YK-4-279 and TK-216, especially among the ABC DLBCL cell lines (P<0.05). SPIB is a known oncogene for ABC DLBCL (Lenz et al, PNAS 2008) and is involved in the response to lenalidomide in ABC DLBCL (Yang et al, Cancer Cell 2012). YK-4-279 inhibits the binding of EWS1-FLI1 to the helicases RHA and DDX5 (Selvanathan et al, PNAS 2012). Thus, it was assessed whether YK-4-279 and TK-216 can have a similar effect on SPIB and whether they induce cellular effects similar to lenalidomide. Protein modelling demonstrated that the 3D structure of FLI1 and SPIB are highly overlapping. Co-IP experiments showed the binding of SPIB to RHA and DDX5 in two ABC DLBCL cell lines. The binding to RHA and, to a lesser extent, to DDX5 was decreased upon exposing the cells to TK216 or YK-4-279 (500 nM, 4-10 h). Similarly to lenalidomide (Yang et al, Cancer Cell 2012), TK-216 decreased IRF4 and upregulated IRF7 protein in cells. GEP of two ABC DLBCL cell lines exposed to the active (S)-enantiomer or to the inactive (R)-enantiomer (500 nM, 4-8 h) showed that (S)-YK-4-279 caused an important upregulation of multiple snoRNAs—an effect compatible with an interference of the compound on helicases and RNA editing. In ABC DLBCL, the ETS inhibitor YK-4-279 and its clinical derivative TK-216 interfere with SPIB and helicases involved in RNA editing. Moreover, both compounds act similarly to lenalidomide inhibiting IRF4 and upregulating IRF7 and synergize with the IMID in both ABC DLBCL and MCL.

Exemplary Methods and Compositions

Method 1: A method for inducing aptosis in a cell comprising a myeloblast produced in acute myeloid leukemia or a lymphocyte produced in diffuse large B cell lymphoma, comprising contacting the cell with an effective amount of a combination of:

at least one therapeutic agent selected from the group consisting of an immunomodulator, a bromodomain, an extra-terminal protein inhibitor, an anti-CD20 monoclonal antibody, and a BCL2 inhibitor; and a compound having a structure of Formula (I):

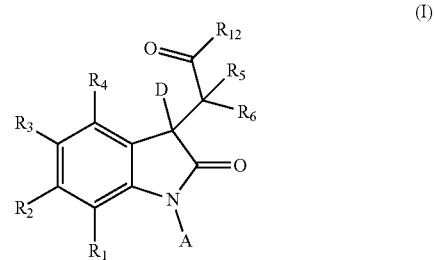

or a stereoisomer, a pharmaceutically acceptable salt, or solvate thereof, wherein $R_1$, $R_2$, $R_3$, and $R_4$ are independently selected from the group consisting of H, Cl, —CN and —CF$_3$; wherein A is selected from the group consisting of H and $C_{1-6}$ alkyl; wherein D is selected from the group consisting of —OH and —O($C_{1-6}$ alkyl); wherein $R_5$ and $R_6$ are independently selected from the group consisting of H, F, and $C_{1-6}$ alkyl, or wherein $R_5$ and $R_6$ taken together form a substituted or unsubstituted cycloalkyl ring; wherein $R_{12}$ is independently selected from the group consisting of substituted or unsubstituted $C_{3-8}$ cycloalkyl, substituted or unsubstituted $C_{3-8}$ heterocycloalkyl,

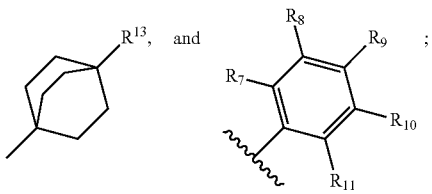

wherein $R_7$, $R_8$, $R_9$, $R_{10}$ and $R_{11}$ are independently selected from the group consisting of H, halogen, CN, $CF_3$, $C_{1-6}$ alkyl, aryl, heteroaryl, —O($C_{1-6}$ alkyl), —O(aryl), —O(heteroaryl), —$CO_2H$, —$CO_2(C_{1-6}$ alkyl), —$NHSO_2(C_{1-6}$ alkyl), —$NHSO_2$(aryl), —NHCONH($C_{1-6}$ alkyl), —NHCON($C_{1-6}$ alkyl)$_2$, —N($C_{1-6}$ alkyl)CONH$_2$, —N($C_{1-6}$ alkyl)CONH($C_{1-6}$ alkyl), —N($C_{1-6}$ alkyl)CON($C_{1-6}$ alkyl)$_2$, —$SO_2(C_{1-6}$ alkyl), —$SO_2NH_2$, —$SO_2NH(C_{1-6}$ alkyl), —$SO_2N$ ($C_{1-6}$ alkyl)$_2$; and wherein $R^{13}$ selected from the group consisting of —O($C_{1-6}$ alkyl) and —N($C_{1-6}$ alkyl)$_2$.

Method 2: A method of treating acute myeloid leukemia or diffuse large B cell lymphoma, comprising administering to a patient in need thereof an anti-proliferative amount of a combination of:
at least one therapeutic agent selected from the group consisting of an immunomodulator, a bromodomain, an extra-terminal protein inhibitor, an anti-CD20 monoclonal antibody, and a BCL2 inhibitor; and
a compound having a structure of Formula (I):

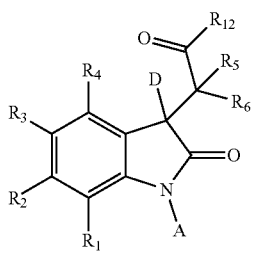

(I)

or a stereoisomer, a pharmaceutically acceptable salt, or solvate thereof, wherein $R_1$, $R_2$, $R_3$, and $R_4$ are independently selected from the group consisting of H, Cl, —CN and —$CF_3$; wherein A is selected from the group consisting of H and $C_{1-6}$ alkyl; wherein D is selected from the group consisting of —OH and —O($C_{1-6}$ alkyl); wherein $R_5$ and $R_6$ are independently selected from the group consisting of H, F, and $C_{1-6}$ alkyl, or wherein $R_5$ and $R_6$ taken together form a substituted or unsubstituted cycloalkyl ring; wherein $R_{12}$ is independently selected from the group consisting of substituted or unsubstituted $C_{3-8}$ cycloalkyl, substituted or unsubstituted $C_{3-8}$ heterocycloalkyl,

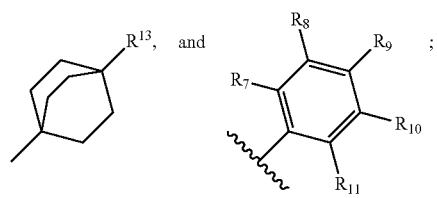

wherein $R_7$, $R_8$, $R_9$, $R_{10}$ and $R_{11}$ are independently selected from the group consisting of H, halogen, CN, $CF_3$, $C_{1-6}$ alkyl, aryl, heteroaryl, —O($C_{1-6}$ alkyl), —O(aryl), —O(heteroaryl), —$CO_2H$, —$CO_2(C_{1-6}$ alkyl), —$NHSO_2(C_{1-6}$ alkyl), —$NHSO_2$(aryl), —NHCONH($C_{1-6}$ alkyl), —NHCON($C_{1-6}$ alkyl)$_2$, —N($C_{1-6}$ alkyl)CONH$_2$, —N($C_{1-6}$ alkyl)CONH($C_{1-6}$ alkyl), —N($C_{1-6}$ alkyl)CON($C_{1-6}$ alkyl)$_2$, —$SO_2(C_{1-6}$ alkyl), —$SO_2NH_2$, —$SO_2NH(C_{1-6}$ alkyl), —$SO_2N$(Cl-alkyl)$_2$; and wherein $R^{13}$ selected from the group consisting of —O($C_{1-6}$ alkyl) and —N($C_{1-6}$ alkyl)$_2$.

Method 3: The method of any one of Methods 1 through 2, wherein $R_9$ is selected from the group consisting of H, halogen, CN, $CF_3$, $C_{1-6}$ alkyl, aryl, heteroaryl, —O(aryl), —O(heteroaryl), —$CO_2H$, —$CO_2(C_{1-6}$ alkyl), —$NHSO_2$ ($C_{1-6}$ alkyl), —$NHSO_2$(aryl), —NHCONH($C_{1-6}$ alkyl), —NHCON($C_{1-6}$ alkyl)$_2$, —N($C_{1-6}$ alkyl)CONH$_2$, —N($C_{1-6}$ alkyl)CONH($C_{1-6}$ alkyl), —N($C_{1-6}$ alkyl)CON($C_{1-6}$ alkyl)$_2$, —$SO_2(C_{1-6}$ alkyl), —$SO_2NH_2$, —$SO_2NH(C_{1-6}$ alkyl), —$SO_2N(C_{1-6}$ alkyl)$_2$; and wherein $R^{13}$ selected from the group consisting of —O($C_{1-6}$ alkyl) and —N($C_{1-6}$ alkyl)$_2$.

Method 4: The method of any one of Methods 1 through 3, wherein the cell is mammalian.

Method 5: The method of any one of Methods 1 through 4, wherein the cell is human.

Method 6: The method of any one of Methods 1 through 5, wherein the cell is in vitro.

Method 7: The method of any one of Methods 1 through 6, wherein the cell is in vivo.

Method 8: The method of any one of Methods 1 through 7, wherein the therapeutic agent is an immunomodulator.

Method 9: The method of any one of Methods 1 through 7, wherein the immunomodulator is lenalidomide.

Method 10: The method of any one of Methods 1 through 7, wherein the therapeutic agent is a bromodomain and extra-terminal protein inhibitor.

Method 11: The method of any one of Methods 1 through 7, wherein the bromodomain and extra-terminal protein inhibitor is OTX015.

Method 12: The method of any one of Methods 1 through 7, wherein the therapeutic agent is an anti-CD20 monoclonal antibody Method 13: The method of any one of Methods 1 through 7, wherein the anti-CD20 monoclonal antibody is rituximab.

Method 14: The method of any one of Methods 1 through 7, wherein the therapeutic agent is a BCL2 inhibitor.

Method 15: The method of any one of Methods 1 through 7, wherein the BCL2 inhibitor is venetoclax.

Method 16: The method of any one of Methods 1 through 15, wherein $R_9$ is selected from the group consisting of aziridinyl, azetidinyl, pyrrolidinyl, and morpholinolyl.

Method 17: The method of any one of Methods 1 through 15, wherein $R_9$ is selected from the group consisting of isopropyl and cyclopropyl.

Method 18: The method of any one of Methods 1 through 15, wherein the compound has a structure of Formula (Ia):

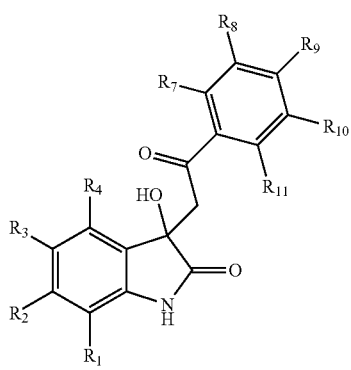

(Ia)

or a stereoisomer, a pharmaceutically acceptable salt, or solvate thereof, wherein $R_1$, $R_2$, $R_3$, and $R_4$ are independently selected from the group consisting of H and Cl; wherein $R_7$, $R_8$, $R_{10}$ and $R_{11}$ are independently selected from the group consisting of H and halogen; and wherein $R_9$ is independently selected from the group consisting $C_{3-8}$ cycloalkyl and $C_{3-8}$ heterocycloalkyl.

Method 19: The method of any one of Methods 1 through 15, wherein $R_1$ and $R_4$ are Cl and $R_2$ and $R_3$ are H.

Method 20: The method of any one of Methods 1 through 15, wherein the compound has a structure selected from the group consisting of:

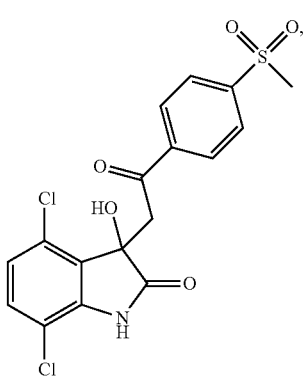

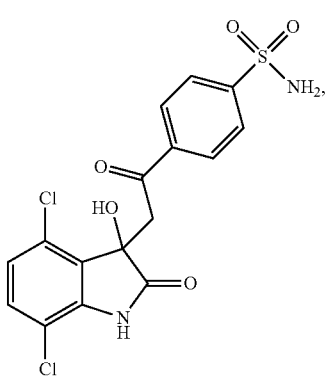

-continued

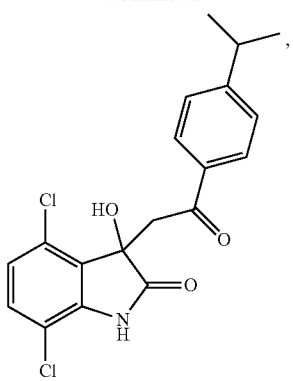

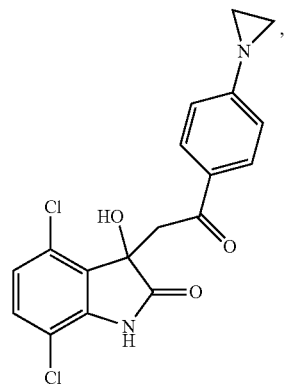

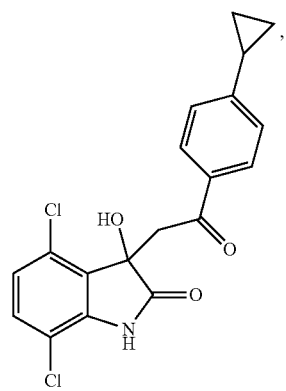

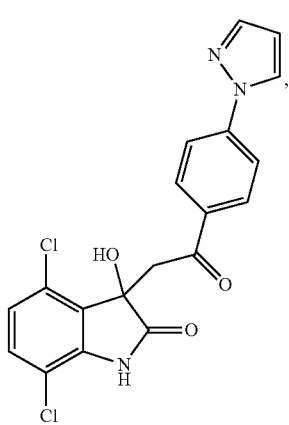

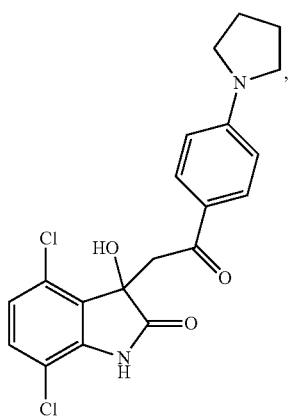
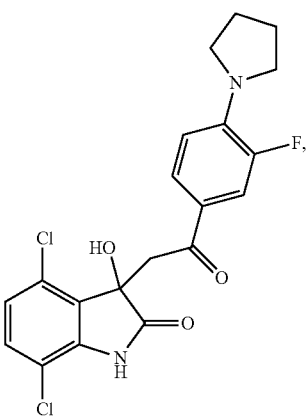
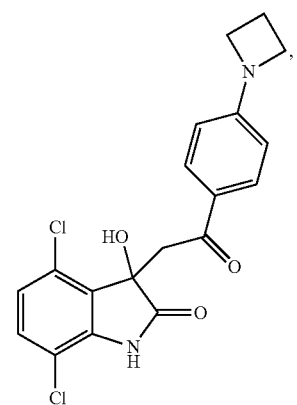
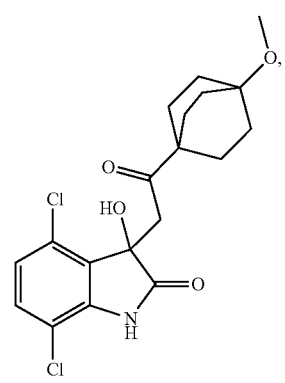
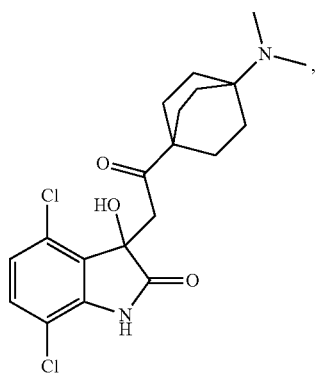
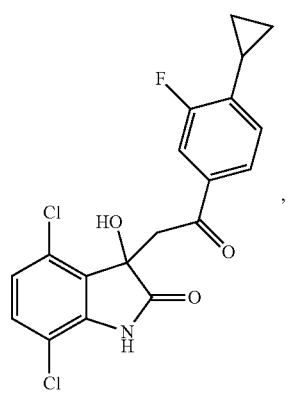
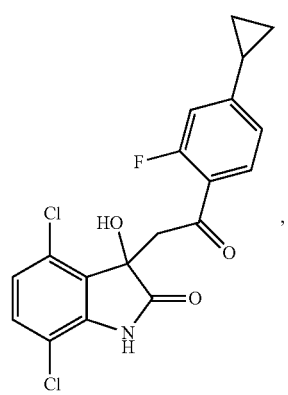
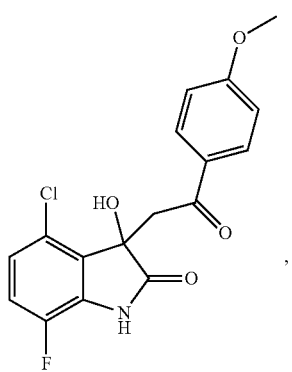

-continued

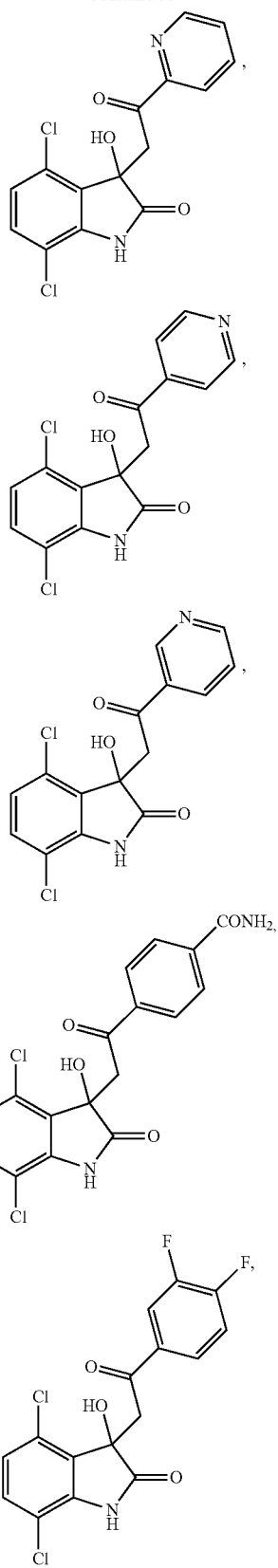

or a stereoisomer, a pharmaceutically acceptable salt, ester, or solvate thereof.

Method 21: The method of any one of Methods 1 through 15, wherein the compound has a structure selected from the group consisting of:

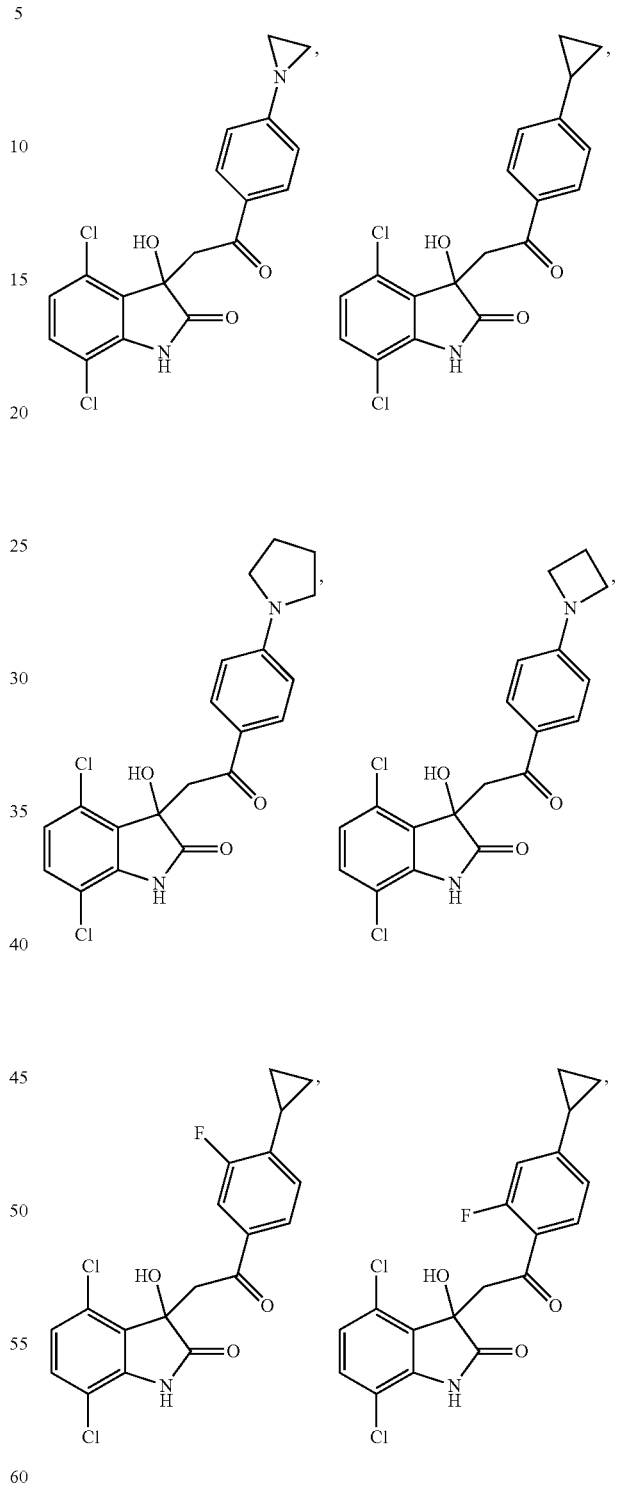

or a stereoisomer, a pharmaceutically acceptable salt, ester, or solvate thereof.

Method 22: The method of any one of Methods 1 through 15, wherein the compound has a structure selected from the group consisting of:

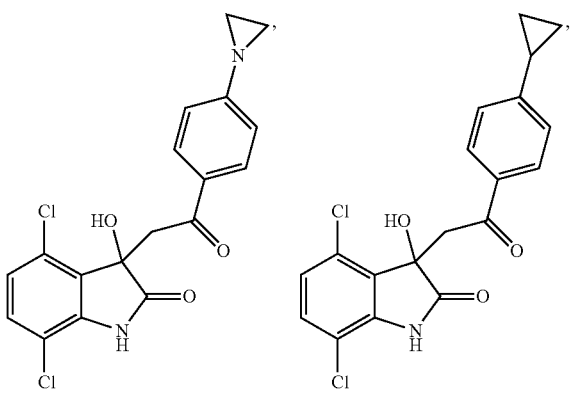

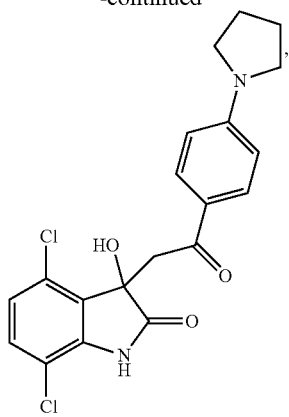

or a stereoisomer, a pharmaceutically acceptable salt, ester, or solvate thereof.

Method 24: The method of any one of Methods 1 through 15, wherein the compound has a structure:

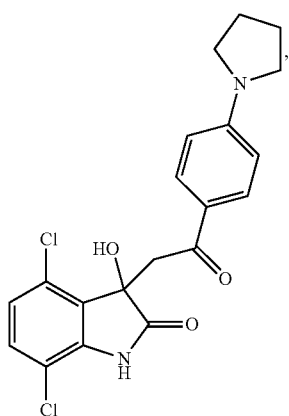 [SMILES: O=C(CC1(O)C(=O)Nc2c(Cl)ccc(Cl)c21)c1ccc(N2CCCC2)cc1]

or a stereoisomer, a pharmaceutically acceptable salt, ester, or solvate thereof.

Method 23: The method of any one of Methods 1 through 15, wherein the compound has a structure selected from the group consisting of:

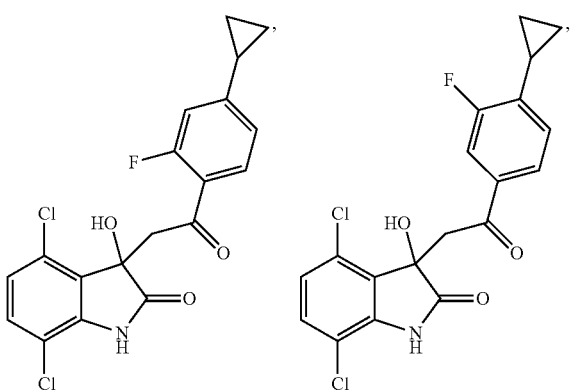

or a stereoisomer, a pharmaceutically acceptable salt, ester, or solvate thereof.

Method 25: The method of any one of Methods 1 through 15, wherein the compound has a structure:

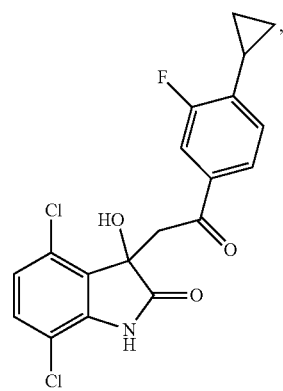 [SMILES: O=C(CC1(O)C(=O)Nc2c(Cl)ccc(Cl)c21)c1ccc(C2CC2)c(F)c1]

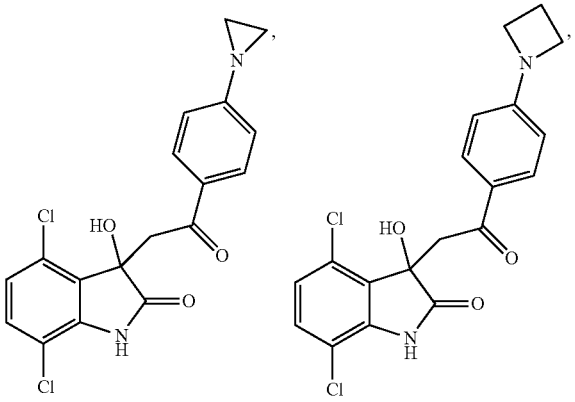

or a stereoisomer, a pharmaceutically acceptable salt, ester, or solvate thereof.

Method 26: The method of any one of Methods 1 through 15, wherein the compound has a structure:

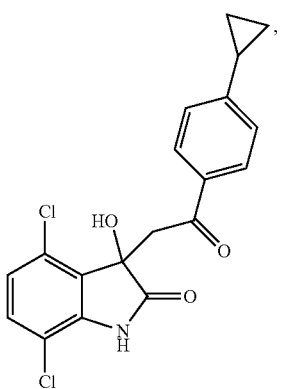

or a stereoisomer, a pharmaceutically acceptable salt, ester, or solvate thereof.

Composition 27: A pharmaceutical composition, comprising:
 at least one therapeutic agent selected from the group consisting of an immunomodulator, a bromodomain, an extra-terminal protein inhibitor, an anti-CD20 monoclonal antibody, and a BCL2 inhibitor; and
 a compound having a structure of Formula (I):

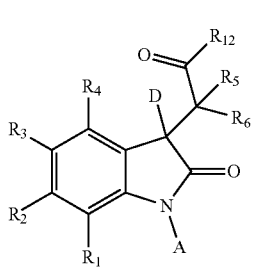

or a stereoisomer, a pharmaceutically acceptable salt, or solvate thereof, wherein $R_1$, $R_2$, $R_3$, and $R_4$ are independently selected from the group consisting of H, Cl, —CN and —$CF_3$; wherein A is selected from the group consisting of H and $C_{1-6}$ alkyl; wherein D is selected from the group consisting of —OH and —O($C_{1-6}$ alkyl); wherein $R_5$ and $R_6$ are independently selected from the group consisting of H, F, and $C_{1-6}$ alkyl, or wherein $R_5$ and $R_6$ taken together form a substituted or unsubstituted cycloalkyl ring; wherein $R_{12}$ is independently selected from the group consisting of substituted or unsubstituted $C_{3-8}$ cycloalkyl, substituted or unsubstituted $C_{3-8}$ heterocycloalkyl,

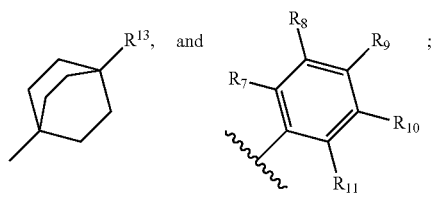

wherein $R_7$, $R_8$, $R_9$, $R_{10}$ and $R_{11}$ are independently selected from the group consisting of H, halogen, CN, $CF_3$, $C_{1-6}$ alkyl, aryl, heteroaryl, —O($C_{1-6}$ alkyl), —O(aryl), —O(heteroaryl), —$CO_2$H, —$CO_2$($C_{1-6}$ alkyl), —$NHSO_2$($C_{1-6}$ alkyl), —$NHSO_2$(aryl), —NHCONH($C_{1-6}$ alkyl), —NHCON($C_{1-6}$ alkyl)$_2$, —N($C_{1-6}$ alkyl)$CONH_2$, —N($C_{1-6}$ alkyl)CONH($C_{1-6}$ alkyl), —N($C_{1-6}$ alkyl)CON($C_{1-6}$ alkyl)$_2$, —$SO_2$($C_{1-6}$ alkyl), —$SO_2NH_2$, —$SO_2$NH($C_{1-6}$ alkyl), —$SO_2$N(Cl-alkyl)$_2$; and wherein $R^{13}$ selected from the group consisting of —O($C_{1-6}$ alkyl) and —N($C_{1-6}$ alkyl)$_2$.

Composition 28: The composition of Composition 1, wherein $R_9$ is selected from the group consisting of H, halogen, CN, $CF_3$, $C_{1-6}$ alkyl, aryl, heteroaryl, —O(aryl), —O(heteroaryl), —$CO_2$H, —$CO_2$($C_{1-6}$ alkyl), —$NHSO_2$($C_{1-6}$ alkyl), —$NHSO_2$(aryl), —NHCONH($C_{1-6}$ alkyl), —NHCON($C_{1-6}$ alkyl)$_2$, —N($C_{1-6}$ alkyl)$CONH_2$, —N($C_{1-6}$ alkyl)CONH($C_{1-6}$ alkyl), —N($C_{1-6}$ alkyl)CON($C_{1-6}$ alkyl)$_2$, —$SO_2$($C_{1-6}$ alkyl), —$SO_2NH_2$, —$SO_2$NH($C_{1-6}$ alkyl), —$SO_2$N($C_{1-6}$ alkyl)$_2$; and wherein $R^{13}$ selected from the group consisting of —O($C_{1-6}$ alkyl) and —N($C_{1-6}$ alkyl)$_2$.

Composition 29: The composition of any one of Compositions 27 through 28, wherein the therapeutic agent is an immunomodulator.

Composition 30: The composition of any one of Compositions 27 through 28, wherein the immunomodulator is lenalidomide.

Composition 31: The composition of any one of Compositions 27 through 28, wherein the therapeutic agent is a bromodomain and extra-terminal protein inhibitor.

Composition 32: The composition of any one of Compositions 27 through 28, wherein the bromodomain and extra-terminal protein inhibitor is OTX015.

Composition 33: The composition of any one of Compositions 27 through 28, wherein the therapeutic agent is an anti-CD20 monoclonal antibody Composition 34: The composition of any one of Compositions 27 through 28, wherein the anti-CD20 monoclonal antibody is rituximab.

Composition 35: The composition of any one of Compositions 27 through 28, wherein the therapeutic agent is a BCL2 inhibitor.

Composition 36: The composition of any one of Compositions 27 through 28, wherein the BCL2 inhibitor is venetoclax.

Composition 37: The composition of any one of Compositions 27 through 37, wherein $R_9$ is selected from the group consisting of aziridinyl, azetidinyl, pyrrolidinyl, and morpholinolyl.

Composition 38: The composition of any one of Compositions 27 through 37, wherein $R_9$ is selected from the group consisting of isopropyl and cyclopropyl.

Composition 39: The composition of any one of Compositions 27 through 37, wherein the compound has a structure of Formula (Ia):

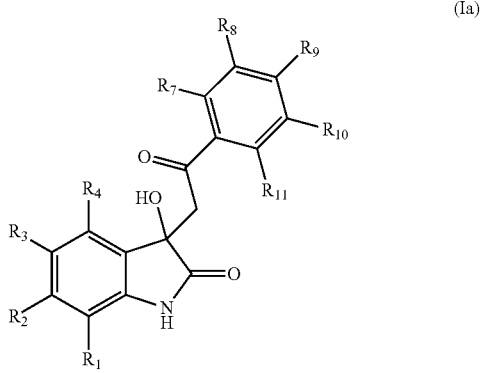

or a stereoisomer, a pharmaceutically acceptable salt, or solvate thereof, wherein $R_1$, $R_2$, $R_3$, and $R_4$ are independently selected from the group consisting of H and Cl; wherein $R_7$, $R_8$, $R_{10}$ and $R_{11}$ are independently selected from the group consisting of H and halogen; and wherein $R_9$ is independently selected from the group consisting $C_{3-8}$ cycloalkyl and $C_{3-8}$ heterocycloalkyl.

Composition 40: The composition of any one of Compositions 27 through 37, wherein $R_1$ and $R_4$ are Cl and $R_2$ and $R_3$ are H.

Composition 41: The composition of any one of Compositions 27 through 37, wherein the compound has a structure selected from the group consisting of:

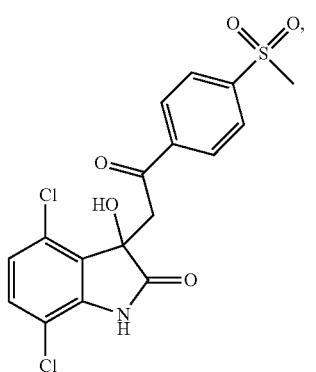

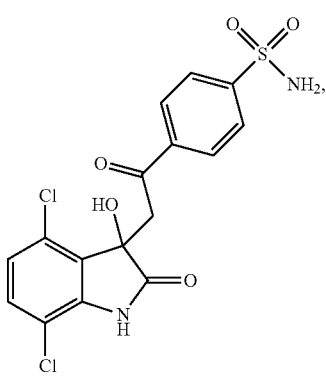

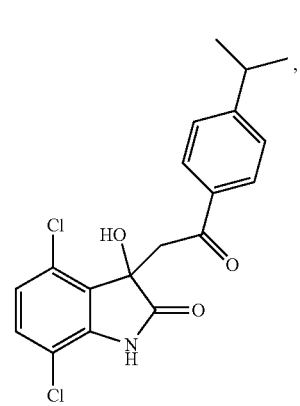

-continued

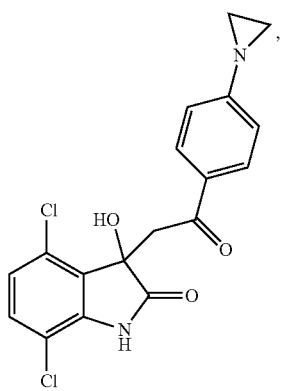

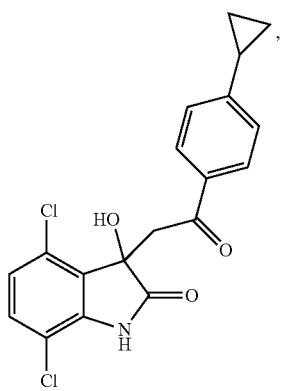 [SMILES: O=C(CC1(O)C(=O)Nc2c(Cl)ccc(Cl)c21)c1ccc(C2CC2)cc1]

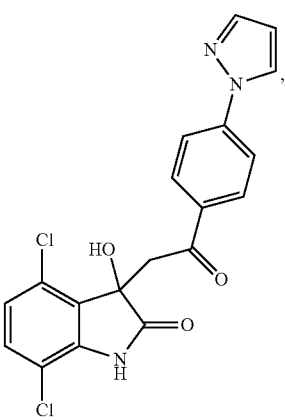

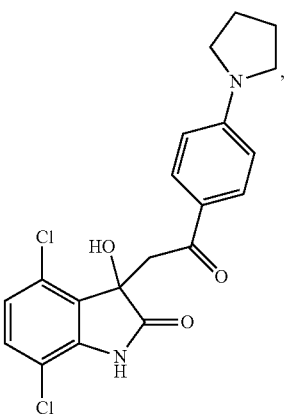

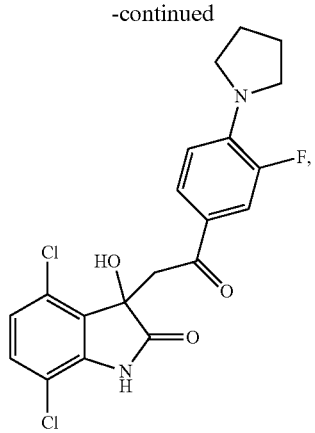
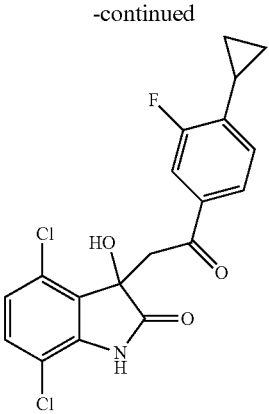

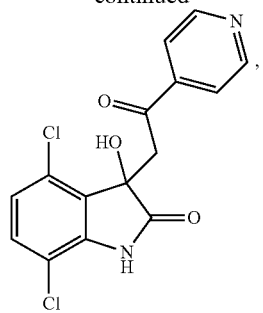
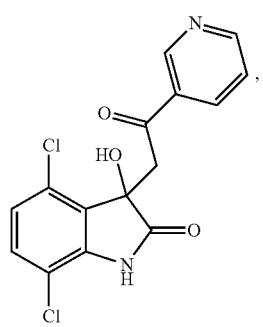
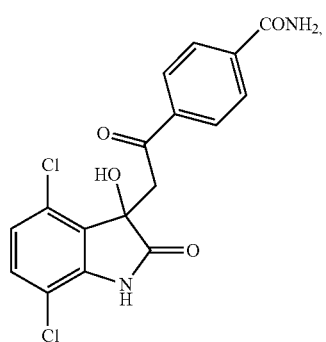
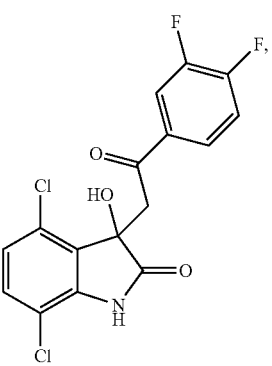
or a stereoisomer, a pharmaceutically acceptable salt, ester, or solvate thereof.
Composition 42: The composition of any one of Compositions 27 through 37, wherein the compound has a structure selected from the group consisting of:
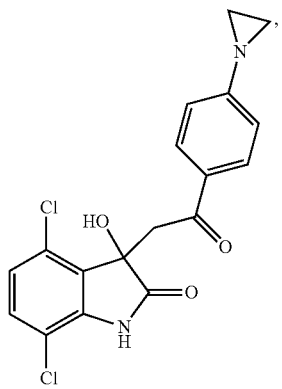
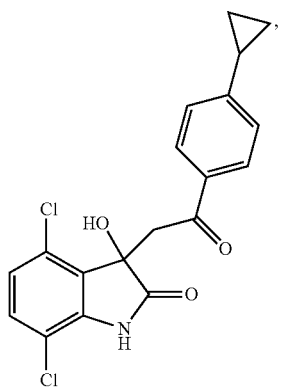
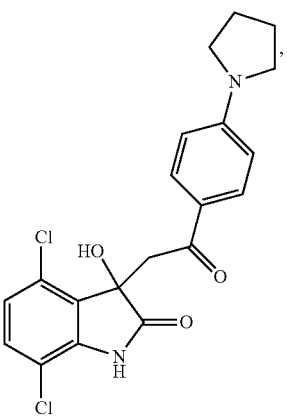 [SMILES: O=C(CC1(O)C(=O)Nc2c(Cl)ccc(Cl)c21)c1ccc(N2CCCC2)cc1]
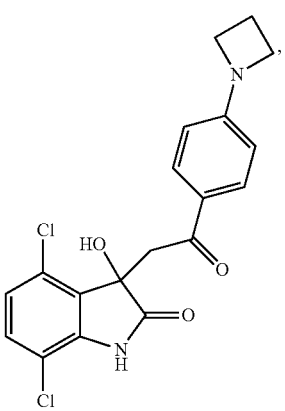

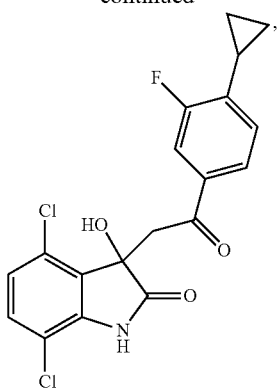

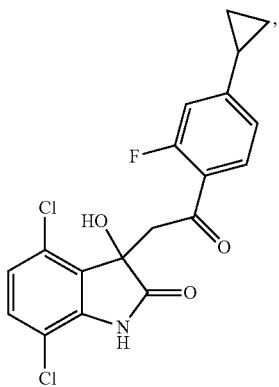

or a stereoisomer, a pharmaceutically acceptable salt, ester, or solvate thereof.

Composition 43: The composition of any one of Compositions 27 through 37, wherein the compound has a structure selected from the group consisting of:

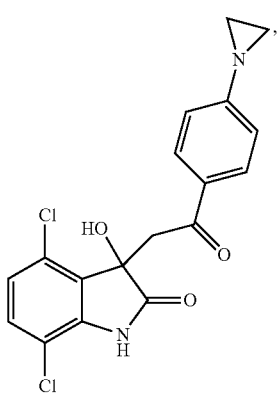 [SMILES: O=C(CC1(O)C(=O)Nc2c(Cl)ccc(Cl)c21)c1ccc(C2CC2)cc1]

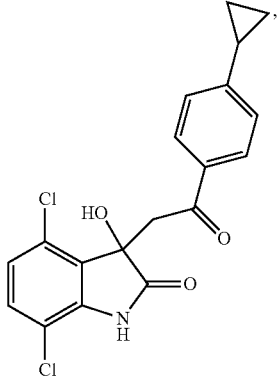

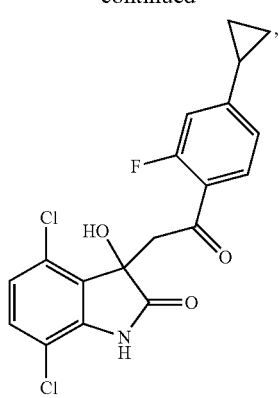

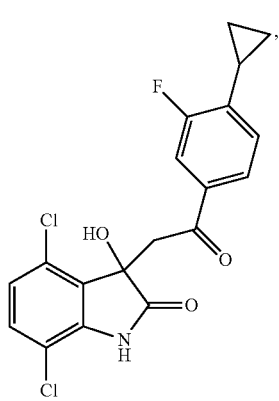

or a stereoisomer, a pharmaceutically acceptable salt, ester, or solvate thereof.

Composition 44: The composition of any one of Compositions 27 through 37, wherein the compound has a structure selected from the group consisting of:

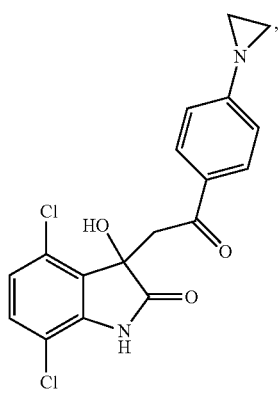

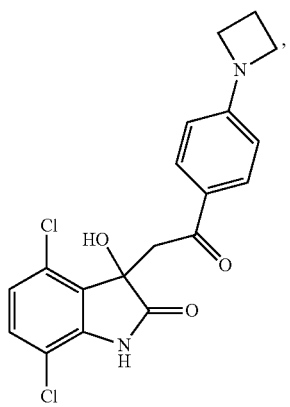

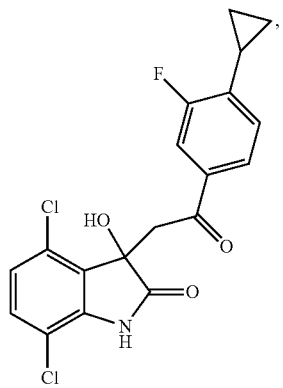

or a stereoisomer, a pharmaceutically acceptable salt, ester, or solvate thereof.

Composition 47, wherein the compound has a structure:

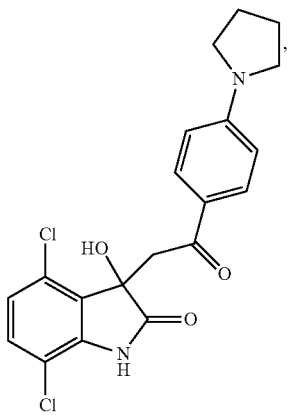

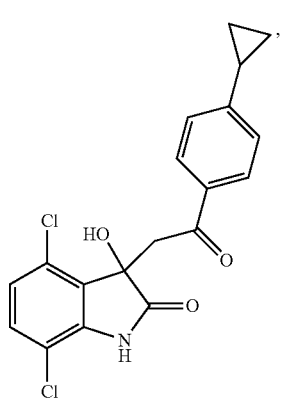

or a stereoisomer, a pharmaceutically acceptable salt, ester, or solvate thereof.

Composition 45: The composition of any one of Compositions 27 through 37, wherein the compound has a structure:

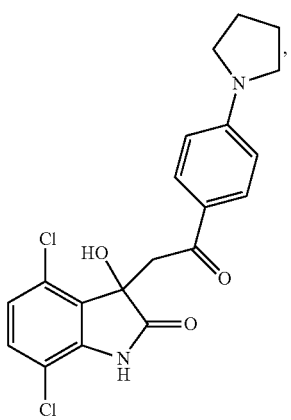

or a stereoisomer, a pharmaceutically acceptable salt, ester, or solvate thereof.

Composition 46: The composition of any one of Compositions 27 through 37, wherein the compound has a structure:

or a stereoisomer, a pharmaceutically acceptable salt, ester, or solvate thereof.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for inducing apoptosis in a lymphocyte produced in mantle cell lymphoma or diffuse large B cell lymphoma, comprising contacting the cell with an effective amount of:

lenalidomide; and
a compound having a structure:

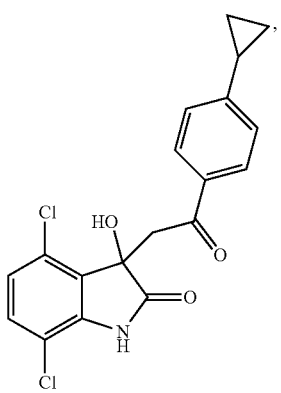 [SMILES: O=C(CC1(O)C(=O)Nc2c(Cl)ccc(Cl)c21)c1ccc(C2CC2)cc1]

or a stereoisomer, a pharmaceutically acceptable salt, or solvate thereof.

2. The method of claim 1, wherein the compound has a structure:

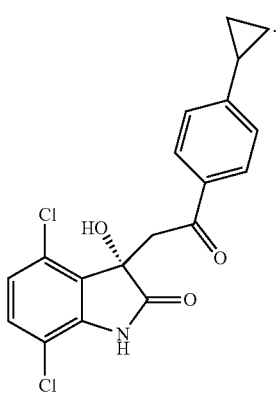 [SMILES: O=C(C[C@@]1(O)C(=O)Nc2c(Cl)ccc(Cl)c21)c1ccc(C2CC2)cc1]

3. The method of claim 1, wherein the compound has a structure:

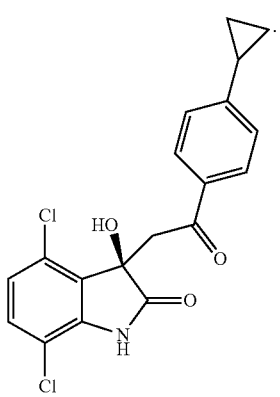 [SMILES: O=C(C[C@]1(O)C(=O)Nc2c(Cl)ccc(Cl)c21)c1ccc(C2CC2)cc1]

4. The method of claim 1, wherein the lymphocyte is produced in mantle cell lymphoma.

5. The method of claim 1, wherein the lymphocyte is produced in diffuse large B cell lymphoma.

6. A pharmaceutical composition, comprising:
lenalidomide; and
a compound having a structure:

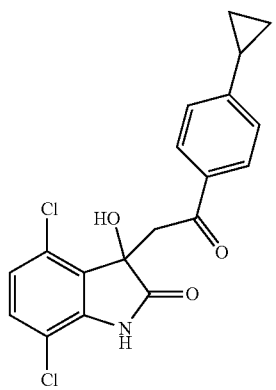 [SMILES: O=C(CC1(O)C(=O)Nc2c(Cl)ccc(Cl)c21)c1ccc(C2CC2)cc1]

or a stereoisomer, a pharmaceutically acceptable salt, or solvate thereof.

7. The pharmaceutical composition of claim 6, wherein the compound has a structure:

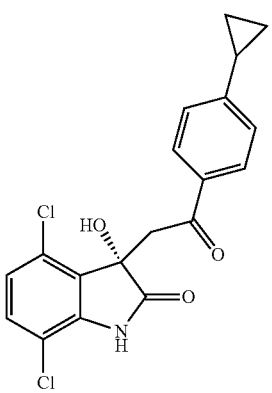

8. The pharmaceutical composition of claim 6, wherein the compound has a structure:

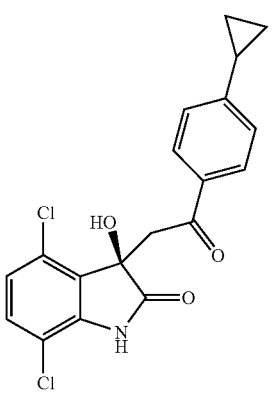

* * * * *